US012570948B2

(12) United States Patent
    Thakkar et al.

(10) Patent No.: US 12,570,948 B2
(45) Date of Patent: Mar. 10, 2026

(54) SYSTEMS, DEVICES, AND METHODS FOR FLUID TRANSFER WITHIN AN AUTOMATED CELL PROCESSING SYSTEM

(71) Applicant: Cellares Corporation, South San Francisco, CA (US)

(72) Inventors: Bharat S. Thakkar, Campbell, CA (US); Matthias Weber, South San Francisco, CA (US)

(73) Assignee: Cellares Corporation, South San Francisco, CA (US)

( * ) Notice: Subject to any disclaimer, the term of this patent is extended or adjusted under 35 U.S.C. 154(b) by 0 days.

(21) Appl. No.: 18/759,602

(22) Filed: Jun. 28, 2024

(65) Prior Publication Data

US 2025/0002837 A1     Jan. 2, 2025

Related U.S. Application Data

(60) Provisional application No. 63/524,596, filed on Jun. 30, 2023.

(51) Int. Cl.
    C12M 1/00        (2006.01)
    B01L 3/00        (2006.01)
    (Continued)

(52) U.S. Cl.
    CPC ............ C12M 41/48 (2013.01); C12M 23/40 (2013.01); C12M 23/42 (2013.01); C12M 29/06 (2013.01); C12M 37/02 (2013.01); C12M 41/30 (2013.01)

(58) Field of Classification Search
    CPC .............................. C12M 23/40; C12M 23/42
    See application file for complete search history.

(56) References Cited

U.S. PATENT DOCUMENTS 3,728,227 A     4/1973  Elson et al.
4,234,023 A    11/1980  Sogi et al.
           (Continued)

FOREIGN PATENT DOCUMENTS

CN       104203333 A      12/2014
CN       108660060 A      10/2018
           (Continued)

OTHER PUBLICATIONS

Final Office Action for U.S. Appl. No. 17/331,554 mailed Aug. 29, 2024, 18 pages.
           (Continued)

*Primary Examiner* — Nathan A Bowers
(74) *Attorney, Agent, or Firm* — Cooley LLP

(57)                ABSTRACT

The present disclosure relates to systems, devices, and methods for automated fluid transfer. In an embodiment, the present disclosure relates to a system for fluid transfer between a fluid device and a cartridge for cell processing. The system comprises a first portion comprising an instrument head coupled to a gantry, the instrument head comprising a pneumatic actuator, a peristaltic pump, and a gripping feature for receiving the fluid device. The peristaltic pump may be configured to engage compressible fluidic tubing of a fluid pump module of the fluid device to transfer the fluid between the fluid device and the cartridge. The system further comprises a second portion comprising a docking station for receiving the cartridge. In some variations, movement of the pneumatic actuator relative to the fluid pump module causes occlusion of the compressible fluidic tubing of the fluid pump module by the peristaltic pump.

20 Claims, 36 Drawing Sheets

(51) Int. Cl.

| | |
|---|---|
| *C12M 1/12* | (2006.01) |
| *C12M 1/34* | (2006.01) |
| *C12M 1/36* | (2006.01) |
| *C12M 3/00* | (2006.01) |

(56) References Cited

U.S. PATENT DOCUMENTS

| | | | |
|---|---|---|---|
| 4,696,902 A | 9/1987 | Bisconte | |
| 4,839,292 A | 6/1989 | Cremonese | |
| 4,911,833 A | 3/1990 | Schoendorfer et al. | |
| 5,058,619 A | 10/1991 | Zheng | |
| 5,656,491 A | 8/1997 | Cassani et al. | |
| 6,102,678 A | 8/2000 | Peclat | |
| 6,267,559 B1 | 7/2001 | Mossman et al. | |
| 6,649,419 B1 | 11/2003 | Anderson | |
| 6,891,182 B2 | 5/2005 | Watari et al. | |
| 7,550,287 B2 | 6/2009 | Hibino et al. | |
| 7,745,209 B2 | 6/2010 | Martin et al. | |
| 7,816,128 B2 | 10/2010 | Nakashima et al. | |
| 8,158,426 B2 | 4/2012 | Wilson et al. | |
| 8,158,427 B2 | 4/2012 | Wilson et al. | |
| 8,168,432 B2 | 5/2012 | Wilson et al. | |
| 8,273,572 B2 | 9/2012 | Martin et al. | |
| 8,415,144 B2 | 4/2013 | Wilson et al. | |
| 8,440,458 B2 | 5/2013 | Zijlstra et al. | |
| 8,470,589 B2 | 6/2013 | Martin et al. | |
| 8,492,140 B2 | 7/2013 | Smith et al. | |
| 8,546,142 B2 | 10/2013 | Martin et al. | |
| 8,697,443 B2 | 4/2014 | Wilson et al. | |
| 8,727,132 B2 | 5/2014 | Miltenyi et al. | |
| 8,809,044 B2 | 8/2014 | Wilson | |
| 8,846,399 B2 | 9/2014 | Martin et al. | |
| 8,956,860 B2 | 2/2015 | Vera et al. | |
| 9,040,290 B2 | 5/2015 | Martin et al. | |
| 9,045,721 B2 | 6/2015 | Martin et al. | |
| 9,080,149 B2 | 7/2015 | Bosio et al. | |
| 9,255,243 B2 | 2/2016 | Wilson et al. | |
| 9,279,099 B2 | 3/2016 | Okano et al. | |
| 9,290,730 B2 | 3/2016 | Martin et al. | |
| 9,410,114 B2 | 8/2016 | Wilson et al. | |
| 9,441,192 B2 | 9/2016 | Wilson et al. | |
| 9,499,780 B2 | 11/2016 | Smith et al. | |
| 9,534,195 B2 | 1/2017 | Smith et al. | |
| 9,556,485 B2 | 1/2017 | Lin et al. | |
| 9,567,565 B2 | 2/2017 | Vera et al. | |
| 9,597,355 B2 | 3/2017 | Magnant | |
| 9,625,463 B2 | 4/2017 | Miltenyi et al. | |
| 9,701,932 B2 | 7/2017 | Smith et al. | |
| 9,732,317 B2 | 8/2017 | Wilson | |
| 9,783,768 B2 | 10/2017 | Larcher et al. | |
| 9,845,451 B2 | 12/2017 | Martin et al. | |
| 10,047,342 B2 | 8/2018 | Eibl et al. | |
| 10,053,663 B2 | 8/2018 | Kabaha et al. | |
| 10,119,970 B2 | 11/2018 | Miltenyi et al. | |
| 10,131,876 B2 | 11/2018 | Kaiser et al. | |
| 10,253,316 B2 | 4/2019 | Masquelier et al. | |
| 10,294,658 B2 | 5/2019 | Scannon et al. | |
| 10,323,258 B2 | 6/2019 | Bernate et al. | |
| 10,329,559 B1 | 6/2019 | Masquelier et al. | |
| 10,385,307 B2 | 8/2019 | Rowley et al. | |
| 10,421,959 B1 | 9/2019 | Masquelier et al. | |
| 10,508,288 B1 | 12/2019 | Bernate et al. | |
| 10,519,437 B1 | 12/2019 | Masquelier et al. | |
| 10,533,156 B2 | 1/2020 | Vera et al. | |
| 10,584,333 B1 | 3/2020 | Masquelier et al. | |
| 10,584,334 B1 | 3/2020 | Masquelier et al. | |
| 10,588,994 B2 | 3/2020 | Kawamura et al. | |
| 10,620,212 B2 | 4/2020 | Miltenyi et al. | |
| 10,689,669 B1 | 6/2020 | Feldman et al. | |
| 10,705,090 B2 | 7/2020 | Miltenyi et al. | |
| 10,705,091 B2 | 7/2020 | Miltenyi et al. | |
| 10,723,986 B2 | 7/2020 | Smith et al. | |
| 10,724,043 B2 | 7/2020 | Sixto et al. | |
| 10,844,338 B1 | 11/2020 | Smith et al. | |
| 11,161,111 B2 | 11/2021 | Kabaha et al. | |
| 11,198,845 B2 | 12/2021 | Parietti et al. | |
| 11,371,018 B2 | 6/2022 | Shi et al. | |
| 11,376,587 B2 | 7/2022 | Thakkar et al. | |
| 11,447,745 B2 | 9/2022 | Shi et al. | |
| 11,701,654 B2 | 7/2023 | Azersky et al. | |
| 11,786,896 B2 | 10/2023 | Thakkar et al. | |
| 11,826,756 B2 | 11/2023 | Azersky et al. | |
| 11,872,557 B2 | 1/2024 | Biz et al. | |
| 12,157,119 B2 | 12/2024 | Gerlinghaus et al. | |
| 12,180,453 B2 | 12/2024 | Chang et al. | |
| 12,305,156 B2 | 5/2025 | Burkeen et al. | |
| 12,337,321 B2 | 6/2025 | Malleo et al. | |
| 12,350,664 B2 | 7/2025 | Pesch et al. | |
| 12,350,667 B2 | 7/2025 | Azersky et al. | |
| 12,350,668 B2 | 7/2025 | Azersky et al. | |
| 2003/0030272 A1 | 2/2003 | Johnson et al. | |
| 2005/0070018 A1 | 3/2005 | Johnson et al. | |
| 2005/0186671 A1 | 8/2005 | Cannon et al. | |
| 2005/0260743 A1 | 11/2005 | Drake et al. | |
| 2006/0194193 A1 | 8/2006 | Tsuruta et al. | |
| 2006/0257999 A1 | 11/2006 | Chang et al. | |
| 2007/0185472 A1 | 8/2007 | Baumfalk et al. | |
| 2008/0057568 A1 | 3/2008 | Kan et al. | |
| 2008/0176318 A1 | 7/2008 | Wilson et al. | |
| 2009/0042281 A1 | 2/2009 | Chang et al. | |
| 2009/0247417 A1 | 10/2009 | Haas et al. | |
| 2010/0130732 A1 | 5/2010 | Chung et al. | |
| 2010/0301071 A1 | 12/2010 | Alstad et al. | |
| 2011/0003380 A1 | 1/2011 | Miltenyi et al. | |
| 2011/0223064 A1 | 9/2011 | Katsumi et al. | |
| 2012/0138156 A1 | 6/2012 | Hofman et al. | |
| 2012/0148415 A1* | 6/2012 | Brueckner | F04B 43/1253 |
| | | | 417/1 |
| 2012/0293338 A1 | 11/2012 | Chaffey et al. | |
| 2013/0078624 A1 | 3/2013 | Holmes et al. | |
| 2013/0115617 A1 | 5/2013 | Wilson | |
| 2013/0189120 A1 | 7/2013 | Nelson et al. | |
| 2014/0309795 A1 | 10/2014 | Norton et al. | |
| 2015/0307829 A1 | 10/2015 | Dedry et al. | |
| 2016/0208216 A1 | 7/2016 | Vera et al. | |
| 2016/0303563 A1 | 10/2016 | Granier et al. | |
| 2016/0320381 A1 | 11/2016 | Holmes et al. | |
| 2016/0320422 A1 | 11/2016 | Fritchie et al. | |
| 2017/0014149 A1* | 1/2017 | Nakayashiki | A61B 17/3203 |
| 2017/0058527 A1 | 3/2017 | Williams et al. | |
| 2017/0239420 A1 | 8/2017 | Wells | |
| 2017/0248697 A1* | 8/2017 | Lo | G01S 7/497 |
| 2017/0307502 A1 | 10/2017 | Mason et al. | |
| 2017/0313977 A1 | 11/2017 | Wilson | |
| 2017/0321226 A1 | 11/2017 | Gill et al. | |
| 2017/0348525 A1 | 12/2017 | Sano et al. | |
| 2017/0362554 A1 | 12/2017 | Martin et al. | |
| 2018/0031592 A1 | 2/2018 | Dority | |
| 2018/0051243 A1 | 2/2018 | Hogan et al. | |
| 2018/0078935 A1 | 3/2018 | Hung et al. | |
| 2018/0185849 A1* | 7/2018 | Kaplan | B01L 3/502715 |
| 2018/0196918 A1 | 7/2018 | Sadowski et al. | |
| 2019/0212233 A1 | 7/2019 | Jovanovich et al. | |
| 2019/0275519 A1 | 9/2019 | Castillo et al. | |
| 2019/0292510 A1 | 9/2019 | Tandon et al. | |
| 2019/0316120 A1 | 10/2019 | Masquelier et al. | |
| 2019/0330579 A1 | 10/2019 | Guenat et al. | |
| 2020/0009557 A1 | 1/2020 | Frigard et al. | |
| 2020/0025782 A1 | 1/2020 | Ahlfors | |
| 2020/0048599 A1 | 2/2020 | Firouzi et al. | |
| 2020/0095550 A1 | 3/2020 | Vera et al. | |
| 2020/0132534 A1* | 4/2020 | Luedemann | B01L 3/0217 |
| 2020/0159198 A1 | 5/2020 | Kapre et al. | |
| 2020/0283713 A1 | 9/2020 | Ball et al. | |
| 2020/0292552 A1 | 9/2020 | Miltenyi et al. | |
| 2020/0353004 A1 | 11/2020 | Nowak et al. | |
| 2020/0368411 A1 | 11/2020 | Camisani et al. | |
| 2020/0399578 A1 | 12/2020 | Corso et al. | |
| 2020/0406221 A1 | 12/2020 | Dabrowski et al. | |
| 2021/0032583 A1 | 2/2021 | Smith et al. | |
| 2021/0035655 A1 | 2/2021 | Tanouchi et al. | |
| 2021/0047668 A1 | 2/2021 | Dabrowski et al. | |
| 2021/0079344 A1 | 3/2021 | Bosio et al. | |
| 2021/0147807 A1 | 5/2021 | Lickert et al. | |

(56) References Cited

U.S. PATENT DOCUMENTS

| | | |
|---|---|---|
| 2021/0253997 A1 | 8/2021 | Wilson |
| 2021/0269755 A1 | 9/2021 | Smith et al. |
| 2021/0283565 A1 | 9/2021 | Gerlinghaus et al. |
| 2021/0301239 A1 | 9/2021 | Natsume et al. |
| 2021/0324318 A1 | 10/2021 | Parietti et al. |
| 2021/0354104 A1 | 11/2021 | Pesch et al. |
| 2022/0002652 A1 | 1/2022 | Patrick et al. |
| 2022/0003796 A1 | 1/2022 | Ahlfors |
| 2022/0047862 A1 | 2/2022 | Chang et al. |
| 2022/0121181 A1 | 4/2022 | Sobalvarro et al. |
| 2022/0127558 A1 | 4/2022 | Sowwan et al. |
| 2022/0143610 A1 | 5/2022 | Biz et al. |
| 2022/0150650 A1 | 5/2022 | Rucker |
| 2022/0163438 A1* | 5/2022 | Klas .................. G01N 15/1404 |
| 2022/0259546 A1 | 8/2022 | Blanchard |
| 2022/0282199 A1 | 9/2022 | Vann |
| 2022/0284574 A1 | 9/2022 | Wagner et al. |
| 2022/0325219 A1 | 10/2022 | Parietti et al. |
| 2022/0347683 A1 | 11/2022 | Thakkar et al. |
| 2023/0044320 A1* | 2/2023 | Chalony .............. A61L 26/008 |
| 2023/0149922 A1 | 5/2023 | Thakkar et al. |
| 2023/0159917 A1 | 5/2023 | Handique et al. |
| 2023/0321650 A1 | 10/2023 | Azersky et al. |
| 2023/0415154 A1 | 12/2023 | Pesch et al. |
| 2023/0415155 A1 | 12/2023 | Biz et al. |
| 2024/0018955 A1 | 1/2024 | Hannah et al. |
| 2024/0165613 A1 | 5/2024 | Azersky et al. |
| 2024/0167466 A1 | 5/2024 | Paraluppi |
| 2024/0240764 A1 | 7/2024 | Gabrielli et al. |
| 2024/0254426 A1 | 8/2024 | Elpel et al. |
| 2024/0255537 A1 | 8/2024 | Malleo et al. |
| 2024/0279585 A1* | 8/2024 | Griffin ................... C12M 33/14 |
| 2024/0279588 A1 | 8/2024 | Malleo et al. |
| 2024/0318116 A1 | 9/2024 | Chang et al. |
| 2024/0326043 A1 | 10/2024 | Gerlinghaus et al. |
| 2024/0369586 A1 | 11/2024 | Tian et al. |
| 2024/0377420 A1 | 11/2024 | Cesarek |
| 2024/0390897 A1 | 11/2024 | Azersky et al. |
| 2024/0390898 A1 | 11/2024 | Azersky et al. |
| 2024/0399365 A1 | 12/2024 | Biz et al. |
| 2024/0402206 A1 | 12/2024 | Boppart et al. |
| 2025/0059492 A1 | 2/2025 | Beban et al. |
| 2025/0065331 A1 | 2/2025 | Malleo et al. |
| 2025/0066708 A1 | 2/2025 | Burkeen et al. |
| 2025/0066709 A1 | 2/2025 | Grout et al. |
| 2025/0129321 A1 | 4/2025 | Malleo et al. |
| 2025/0207076 A1 | 6/2025 | Marchiando et al. |
| 2025/0236832 A1 | 7/2025 | Chang et al. |

FOREIGN PATENT DOCUMENTS

| | | |
|---|---|---|
| EP | 0246912 A2 | 11/1987 |
| EP | 0991389 A1 | 4/2000 |
| EP | 0824380 B1 | 1/2002 |
| EP | 3134512 B1 | 1/2019 |
| EP | 2809449 B1 | 10/2019 |
| EP | 3359294 B1 | 5/2020 |
| EP | 3928867 A1 | 12/2021 |
| GB | 2268187 A | 1/1994 |
| JP | 2007325586 A | 12/2007 |
| KR | 20130018286 A | 2/2013 |
| WO | WO-9320440 A1 | 10/1993 |
| WO | WO-2006102416 A2 | 9/2006 |
| WO | WO-2006112870 A1 | 10/2006 |
| WO | WO-2006118282 A1 | 11/2006 |
| WO | WO-2007139742 A1 | 12/2007 |
| WO | WO-2009072003 A2 | 6/2009 |
| WO | WO-2017041051 A1 | 3/2017 |
| WO | WO-2017123663 A1 | 7/2017 |
| WO | WO-2018015561 A1 | 1/2018 |
| WO | WO-2018102471 A1 | 6/2018 |
| WO | WO-2019232504 A2 | 12/2019 |
| WO | WO-2020009700 A1 | 1/2020 |
| WO | WO-2020014264 A1 | 1/2020 |
| WO | WO-2021168368 A1 | 8/2021 |
| WO | WO-2021183687 A2 | 9/2021 |
| WO | WO-2021212124 A1 | 10/2021 |
| WO | WO-2024112702 A1 | 5/2024 |
| WO | WO-2024152008 A1 | 7/2024 |
| WO | WO-2024206703 A1 | 10/2024 |
| WO | WO-2025007051 A2 | 1/2025 |
| WO | WO-2025038974 A1 | 2/2025 |
| WO | WO-2025041046 A1 | 2/2025 |

OTHER PUBLICATIONS

Non-Final Office Action for U.S. Appl. No. 18/244,051 mailed Oct. 9, 2024, 10 pages.

Non-Final Office Action for U.S. Appl. No. 18/799,963 mailed Sep. 30, 2024, 9 pages.

Notice of Allowance for U.S. Appl. No. 18/810,388 mailed on Oct. 9, 2024, 9 pages.

U.S. Appl. No. 18/807,699, filed Aug. 16, 2024, by Beban et al.

U.S. Appl. No. 18/611,632, filed Mar. 20, 2024, by Chang et al.

U.S. Appl. No. 18/652,602, filed May 1, 2024, by Tian et al.

U.S. Appl. No. 18/731,095, filed May 31, 2024, by Boppart et al.

ChargePoint (2021). Aseptic split butterfly valve 10-6 sterility assurance, located at https://www.thechargepoint.com/products/aseptic-split-butterfly-valve-10-6-sterility-assurance/, 2 total pages.

CPC (2014). "6 traits of non-spill: How quick disconnect couplings evolved for low-pressure fluid handling," White Paper 8004, 4 total pages.

CPC (2014). "How single-use connections advance aseptic processing: Increased process flexibility and reliability, reduced costs," White Paper 7004, 6 total pages.

CPC (2018). Comparison Guide: Tube Welders and Aseptic Connectors, Technical Guide 7009, 3 total pages.

EMD Millipore (2015). "Lynx® S2S Connector—Low temperature compatibility (–80"C)," 4 total pages.

Final Office Action mailed on Apr. 28, 2022, for U.S. Appl. No. 17/198,134, filed Mar. 10, 2021, 11 pages.

Final Office Action mailed on Apr. 28, 2022, for U.S. Appl. No. 17/331,554, filed May 26, 2021, 16 pages.

Final Office Action mailed on Jul. 31, 2023, for U.S. Appl. No. 17/331,554, filed May 26, 2021, 19 pages.

Final Office Action mailed on Mar. 31, 2023, for U.S. Appl. No. 17/579,478, filed Jan. 19, 2022, 8 pages.

Garcia et al., "Microfluidic Screening of Electric Fields for Electroporation" Sci Rep. Feb. 19, 2016; 6:21238. pp. 1-11.

Genetic Engineering & Biotechnology News (2006). "Thermal welding for sterile connections," located at https://www.genengnews.com/magazine/47/thermal-welding-for-sterile-connections/, 5 total pages.

International Search Report and Written Opinion for International Application No. PCT/US2023/080593 dated Mar. 21, 2024, 12 pages.

International Search Report and Written Opinion for PCT Application No. PCT/US2024/011486 dated May 24, 2024, 12 pages.

International Search Report mailed on Oct. 13, 2021, for PCT Application No. PCT/US2021/021773, filed on Mar. 10, 2021, 13 pages.

Invitation to Pay Additional Fees for International Application No. PCT/US2024/022079 dated Jul. 17, 2024, 19 pages.

Invitation to Pay Additional fees for International Application No. PCT/US2024/025064, mailed Jul. 16, 2024, 12 pages.

Jain, S. et al. (2011). "The complete automation of cell culture: improvements for high-throughput and high-content screening," J. Biomol. Screen 16:932-939.

Kato, R. et al. (2010). "A Compact, Automated Cell Culture System for Clinical Scale Cell Expansion from Primary Tissues," Tissue Engineering: Part C 16:947-956.

Kempner, M.E. and Felder, R.A., "A review of cell culture automation". JALA: Journal of the Association for Laboratory Automation (Apr. 2002); 7(2): 56-62.

Kino-Oka, M. et al. (2005). "Bioreactor Design for Successive Culture of Anchorage-Dependent Cells Operated in an Automated Manner," Tissue Engineering 11:535-545.

(56) References Cited

OTHER PUBLICATIONS

Knoll, A. et al. (2004). "Flexible automation of cell culture and tissue engineering tasks," Biotechnol. Prog. 20:1825-1835.

Lutkemeyer, D. et al. (2000). "First steps in robot automation of sampling and sample management during cultivation of mammalian cells in pilot scale," Biotechnol. Prog. 16:822-828.

MEDInstill (2021). INTACT™ Connectors, located at https://www.medinstill.com/intactconnectors.php, 1 total page.

Millipore® (2020). "Technical Brief—Choosing the right sterile connector based on design and sterility test results," 4 total pages.

Millipore Sigma (2020). "Lynx® CDR Connectors," Datasheet, 4 total pages.

Millipore Sigma (2021). Lynx® CDR Connectors, located at https://www.emdmillipore.com/US/en/product/Lynx-CDR-Connectors,MM_NF-C188801, 2 total pages.

Non-Final Office Action for U.S. Appl. No. 18/652,602 mailed Jul. 17, 2024, 30 pages.

Non-Final Office Action for U.S. Appl. No. 18/731,095 mailed Aug. 8, 2024, 24 pages.

Non-Final Office Action mailed on Apr. 24, 2024, for U.S. Appl. No. 17/331,554, filed May 26, 2021, 17 pages.

Non-Final Office Action mailed on Dec. 22, 2022, for U.S. Appl. No. 17/579,478, filed Jan. 19, 2022, 8 pages.

Non-Final Office Action mailed on Dec. 3, 2021, for U.S. Appl. No. 17/331,556, filed May 26, 2021, 9 pages.

Non-Final Office Action mailed on Feb. 3, 2022, for U.S. Appl. No. 17/198,134, filed Mar. 10, 2021, 5 pages.

Non-Final Office Action mailed on Jun. 26, 2023, for U.S. Appl. No. 17/198,134, filed Mar. 10, 2021, 15 pages.

Non-Final Office Action mailed on Mar. 16, 2023, for U.S. Appl. No. 17/331,554, filed May 26, 2021, 16 pages.

Non-Final Office Action mailed on May 14, 2024, for U.S. Appl. No. 18/611,632, filed Mar. 20, 2024, 13 pages.

Non-Final Office Action mailed on Oct. 28, 2021, for U.S. Appl. No. 17/331,554, filed May 26, 2021, 11 pages.

Non-Final Office Action mailed on Oct. 6, 2021, for U.S. Appl. No. 17/198,134, filed Mar. 10, 2021, 7 pages.

Non-Final Office Action mailed on Sep. 13, 2023, for U.S. Appl. No. 18/141,329, filed Apr. 28, 2023, 7 pages.

Notice of Allowance mailed on Apr. 11, 2024, for U.S. Appl. No. 17/198,134, filed Mar. 10, 2021, 9 pages.

Notice of Allowance mailed on Jul. 18, 2023, for U.S. Appl. No. 17/849,422, filed Jun. 24, 2022, 8 pages.

Notice of Allowance mailed on Jul. 25, 2023, for U.S. Appl. No. 17/579,478, filed Jan. 19, 2022, 8 pages.

Notice of Allowance mailed on Jun. 8, 2023, for U.S. Appl. No. 17/849,422, filed Jun. 24, 2022, 8 pages.

Notice of Allowance mailed on Mar. 1, 2022, for U.S. Appl. No. 17/331,556, filed May 26, 2021, 8 pages.

Notice of Allowance mailed on Mar. 22, 2023, for U.S. Appl. No. 17/992,784, filed Nov. 22, 2022, 8 pages.

Notice of Allowance mailed on Oct. 4, 2023, for U.S. Appl. No. 18/141,329, filed Apr. 28, 2023, 8 pages.

Pharma Japan, "Astellas Set to Cut Development Time with Cell Culture Robot, Eyes 4 Billion Yen Profit per Product" Aug. 9, 2023, 3 pages.

Qu, B., et al., "Droplet Electroporation in Microfluidics for Efficient Cell Transformation with or without Cell Wall Removal," Lab Chip, 2012, vol. 12, pp. 4483-4488.

Saint Gobain (2017). "Pure-Fit® SC—Secure aseptic connections," Brochure, 5 total pages.

Sartorius Stedim Biotech (2011). "Opta® SFT," 4 total pages.

Schwartz C., "Optimizing Cell Separation with Beckman Coulter's Centrifugal Elutriation System," Beckmann Coulter Life Sciences (2014) 6 total pages.

SeriesLock™ (2021). Features and Specifications, located at https://serieslock.com/, 5 total pages.

Shi, Y. et al. (1992). "Performance of Mammalian Cell Culture Bioreactor with a New Impeller Design," Biotechnology and Bioengineering 40:260-270.

Steris (2018). "A compilation of material compatibilities with vaporized hydrogen peroxide," 2 total pages.

Steris (2018). "Sterility assurance levels (SALS): Irradiation," 3 total pages.

Steris (2020). "Overview of sterilization technology comparison," 1 total page.

Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.

Written Opinion of the International Searching Authority mailed on Oct. 13, 2021, for PCT Application No. PCT/US2021/021773, filed on Mar. 10, 2021, 20 pages.

Final Office Action for U.S. Appl. No. 18/799,963 mailed Jan. 30, 2025, 10 pages.

International Search Report and Written Opinion for PCT Application No. PCT/IB2024/058105 mailed Dec. 16, 2024, 12 pages.

International Search Report and Written Opinion for PCT Application No. PCT/US2024/022079 mailed Sep. 12, 2024, 25 pages.

International Search Report and Written Opinion for PCT Application No. PCT/US2024/042795 mailed Dec. 16, 2024, 11 pages.

Non-Final Office Action for U.S. Appl. No. 18/792,358 mailed on Nov. 6, 2024, 5 pages.

Notice of Allowance for U.S. Appl. No. 18/792,360 mailed on Jan. 29, 2025, 9 pages.

Notice of Allowance for U.S. Appl. No. 18/810,388 mailed Jan. 21, 2025, 8 pages.

U.S. Appl. No. 29/898,923, filed Aug. 2, 2023, by Gerlinghaus et al.

Final Office Action for U.S. Appl. No. 18/244,051 mailed Apr. 4, 2025, 11 pages.

Non-Final Office Action for U.S. Appl. No. 18/807,699 mailed Apr. 29, 2025, 19 pages.

Non-Final Office Action for U.S. Appl. No. 18/920,607 mailed Feb. 28, 2025, 10 pages.

Notice of Allowance for U.S. Appl. No. 17/331,554 mailed Apr. 10, 2025, 6 pages.

Notice of Allowance for U.S. Appl. No. 17/331,554 mailed Mar. 5, 2025, 8 pages.

Notice of Allowance for U.S. Appl. No. 18/487,884 mailed Feb. 26, 2025, 8 pages.

Notice of Allowance for U.S. Appl. No. 18/487,884 mailed on Apr. 3, 2025, 8 pages.

Notice of Allowance for U.S. Appl. No. 18/792,358 mailed on Mar. 3, 2025, 8 pages.

Notice of Allowance for U.S. Appl. No. 18/792,360 mailed Mar. 4, 2025, 9 pages.

Notice of Allowance for U.S. Appl. No. 18/810,388 mailed Apr. 30, 2025, 5 pages.

U.S. Appl. No. 18/988,628, filed Dec. 19, 2024, by Marchiando et al.

Final Office Action for U.S. Appl. No. 18/807,699 mailed on Aug. 20, 2025, 22 pages.

Final Office Action for U.S. Appl. No. 18/920,607 mailed Jun. 4, 2025, 10 pages.

International Search Report and Written Opinion for PCT Application No. PCT/US2024/036245 mailed Jun. 11, 2025, 13 pages.

Non-Final Office Action for U.S. Appl. No. 19/091,700 mailed Jul. 7, 2025, 13 pages.

Notice of Allowance for U.S. Appl. No. 18/799,963 mailed Jul. 1, 2025, 7 pages.

Notice of Allowance for U.S. Appl. No. 19/075,709 mailed Jul. 29, 2025, 10 pages.

Shabalina et al., "ARTag, AprilTag and CALTag Fiducial Systems Comparison in a Presence of Partial Rotation: Manual and Automated Approaches" in ICINCO (2017) LNEE 495:536-558.

* cited by examiner

100

250

Workcell 205

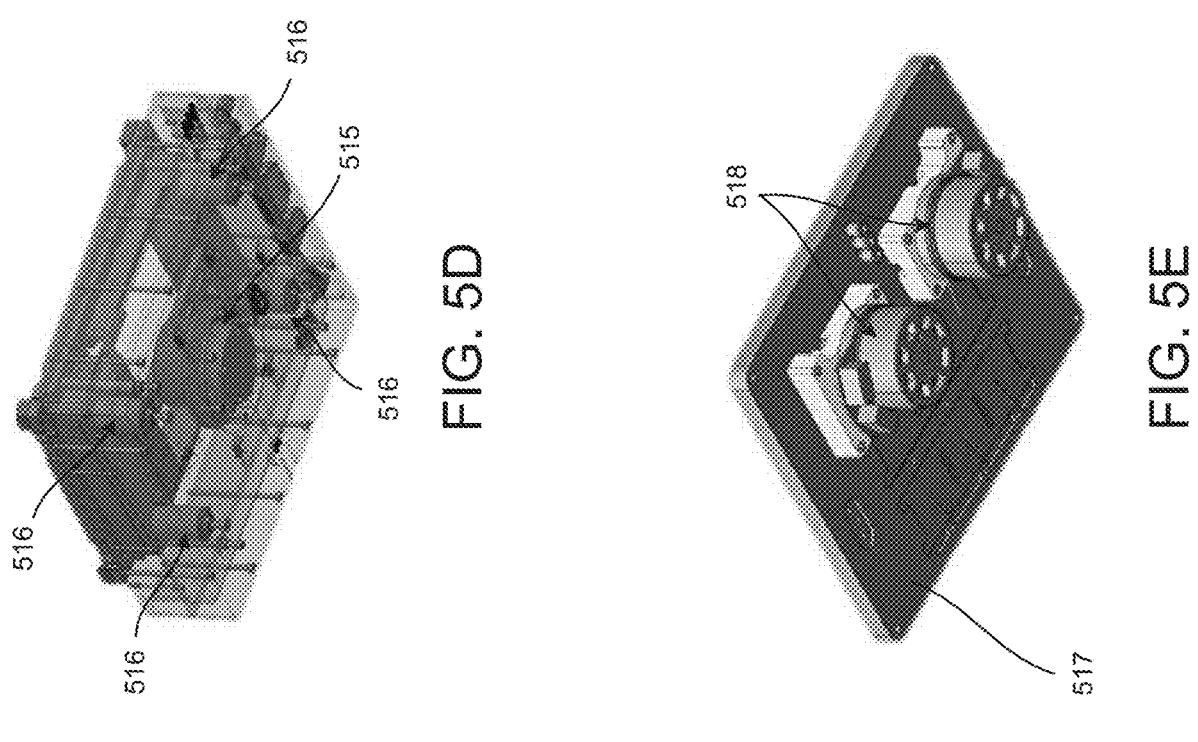
FIG. 5D
FIG. 5E
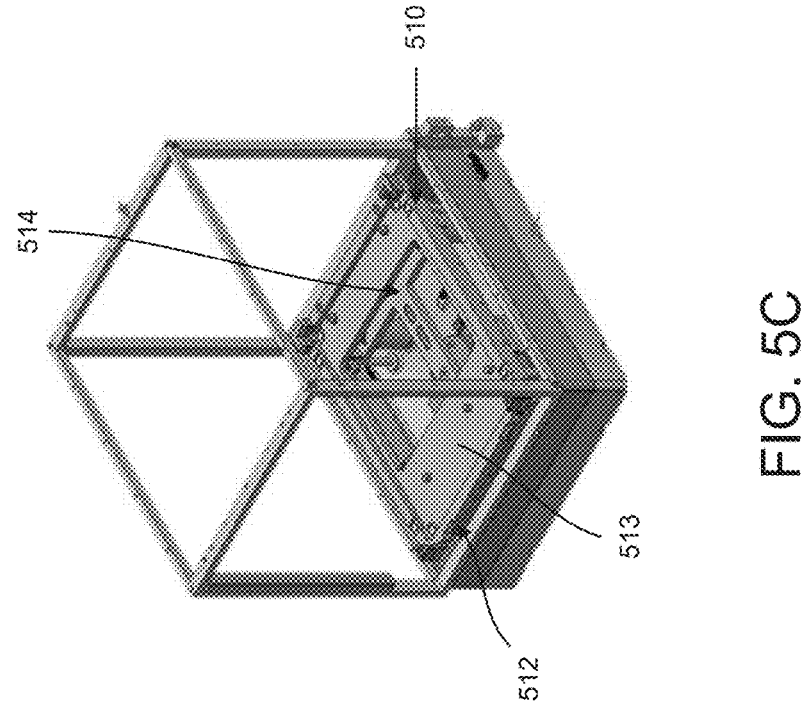
FIG. 5C

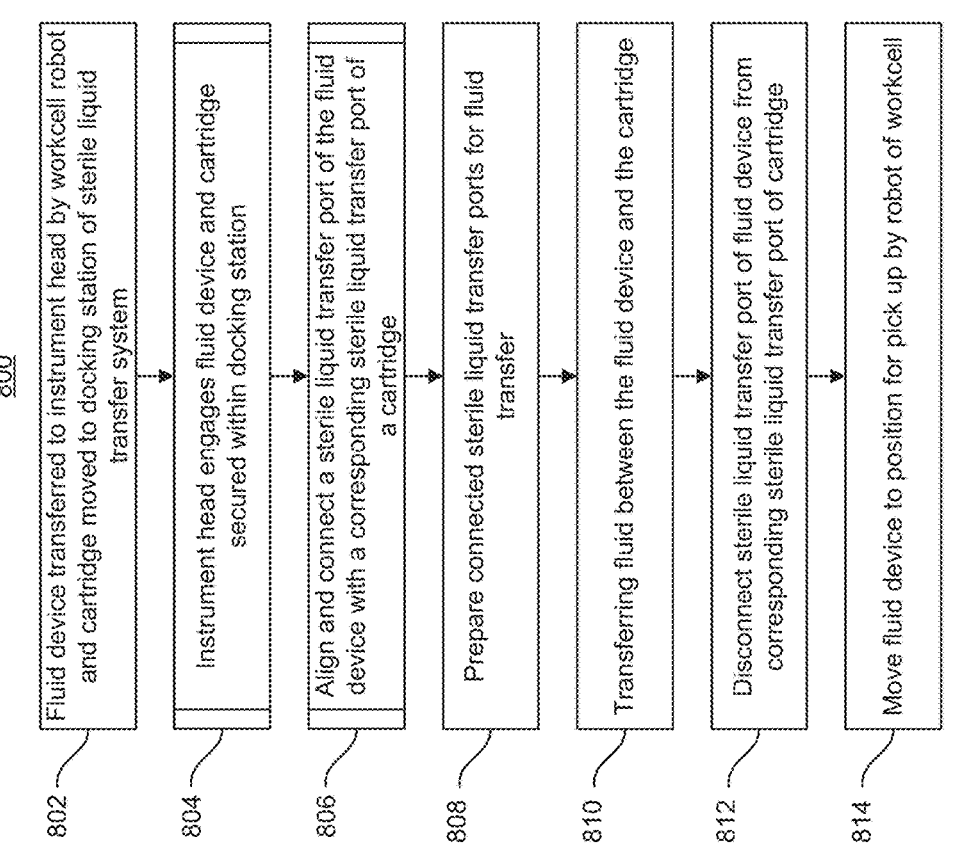

800

802 — Fluid device transferred to instrument head by workcell robot and cartridge moved to docking station of sterile liquid transfer system 804 — Instrument head engages fluid device and cartridge secured within docking station 806 — Align and connect a sterile liquid transfer port of the fluid device with a corresponding sterile liquid transfer port of a cartridge 808 — Prepare connected sterile liquid transfer ports for fluid transfer 810 — Transferring fluid between the fluid device and the cartridge 812 — Disconnect sterile liquid transfer port of fluid device from corresponding sterile liquid transfer port of cartridge 814 — Move fluid device to position for pick up by robot of workcell

FIG. 8

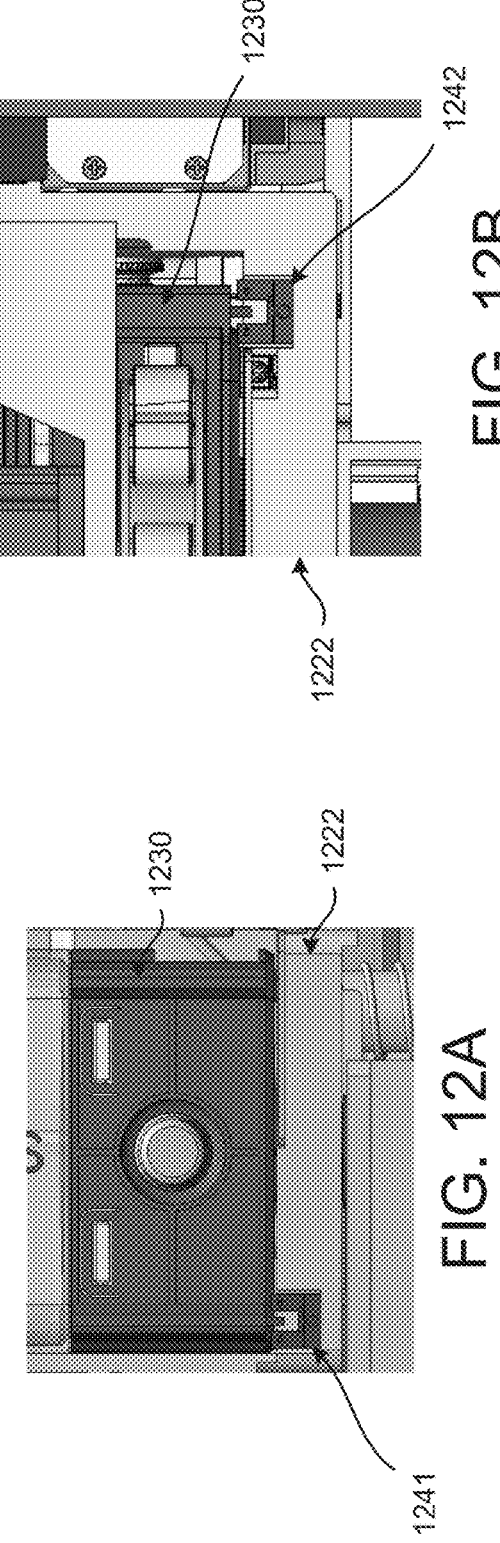
FIG. 12A
FIG. 12B
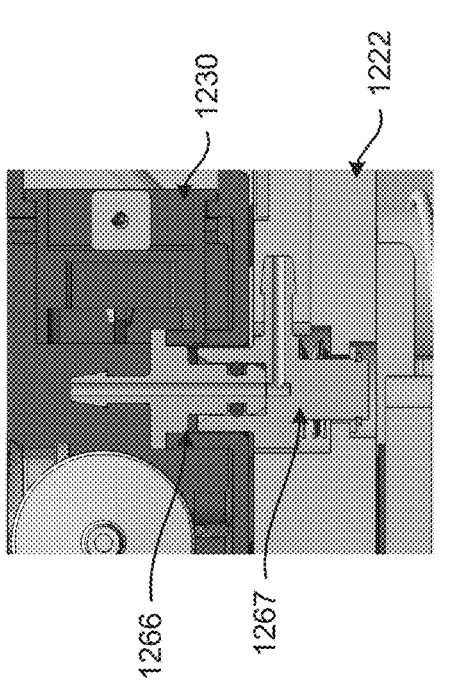
FIG. 12C

SYSTEMS, DEVICES, AND METHODS FOR FLUID TRANSFER WITHIN AN AUTOMATED CELL PROCESSING SYSTEM

CROSS REFERENCE TO RELATED APPLICATIONS

This application claims priority to U.S. Provisional Patent Application Ser. No. 63/524,596 filed Jun. 30, 2023, the contents of which are incorporated herein by reference in their entirety for all purposes.

TECHNICAL FIELD

The present disclosure relates to fluid transfer within a cell processing system.

BACKGROUND

Cell therapy, where cells from a patient or donor are collected, processed ex vivo, and then returned to the same or different patient, has been revolutionary. However, cell therapy manufacturing is a complex, often labor-intensive process that is difficult to "scale-up" and is prone to human error and contamination. Recent efforts have been made toward automating manufacturing of cell therapies. While advances have been made regarding, for example, the ability to automate movements of cells between manufacturing steps, there remain numerous inefficiencies throughout cell therapy manufacturing. For example, the transfer of fluids between cell therapy steps and reagent storage devices continues to be a human touch point and an entryway for error and contamination. Given the importance of sterility in the transferring of fluids to collect samples, replenish culture media, and the like, additional systems, devices, and methods for fluid transfer within a cell processing system are desirable.

SUMMARY

The present disclosure relates generally to systems, devices, and methods for fluid transfer between a fluid device and a cartridge for cell processing. In general, the systems disclosed herein for fluid transfer between the fluid device and the cartridge for cell processing may include a first portion including an instrument head coupled to a gantry and a second portion including a docking station for receiving the cartridge. The instrument head may be movable via the gantry in at least two directions and may include an actuator, a pump, and a gripping feature for receiving the fluid device, wherein the pump may be configured to engage compressible fluidic tubing of a fluid pump module of the fluid device to transfer the fluid between the fluid device and the cartridge. In some variation, the actuator may be a pneumatic actuator and the pump may be a peristaltic pump. In some variations, the instrument head may further include a cap actuator. In some variations, each of the cartridge and the fluid device may further include a sterile liquid transfer port or one or more sterile liquid transfer ports. In some variations, the instrument head may further include sensors, such as cameras, for locating the sterile liquid transfer port of the cartridge. In some variations, the instrument head may further include one or more sensors for controlling a fluid transfer flow rate. Movement of the pneumatic actuator relative to the fluid pump module may cause occlusion of the compressible fluidic tubing of the fluid pump module by the peristaltic pump. In some variations, movement of the pneumatic actuator may include translation of the peristaltic pump relative to the compressible fluidic tubing of the fluid pump module, thereby adjusting the amount of occlusion of the compressible fluidic tubing. The translation of the peristaltic pump relative to the compressible fluidic tubing may modify a distance between bearings of the peristaltic pump and a track of the fluid pump module. In this way, movement of the pneumatic actuator towards the fluid pump module may increase the amount of occlusion of the compressible fluidic tubing. In some variations, the pneumatic actuator may be coupled to the peristaltic pump via a bracket. In some variations, the peristaltic pump may include multiple rollers for engaging the compressible fluidic tubing of the fluid pump module. In some variations, the instrument head may be movable via the gantry in at least two dimensions. In some variations, the docking station may further include a platform. In some variations, the platform of the docking station may include a bioreactor module engagement feature configured to engage with a corresponding bioreactor module of the cartridge. The platform may be a floating platform configured to raise the cartridge into contact with a clamping surface of the docking station, thereby securing the cartridge. In some variations, the platform of the docking station further includes a load cell for measuring a mass of a transferred fluid.

Systems for fluid as described herein may include one or more sensors and a gripping feature for receiving the fluid device, and the fluid device may include a sterile liquid transfer port for transferring the fluid. Likewise, the cartridge may include at least one sterile liquid transfer port. The sterile liquid transfer port of the fluid device may be aligned with a corresponding one of the at least one sterile liquid transfer port of the cartridge using the one or more sensors of the instrument head. In some variations, the one or more sensors may be optical sensors. In some variations, the alignment may be performed via edge detection using data acquired by the one or more sensors. In some variations, the alignment may include detecting a plurality of points on the corresponding one of the at least one sterile liquid transfer port. The plurality of points may include two locations each along three edges of the corresponding one of the at least one sterile liquid transfer port.

A method for sterile fluid transfer between a fluid device and a cartridge for cell processing is also disclosed herein. Generally, the method may include receiving, by a system, a fluid device including a sterile liquid transfer port, aligning the sterile liquid transfer port with one of a plurality of sterile liquid transfer ports of a cartridge, connecting the sterile liquid transfer port to the one of the plurality of sterile liquid transfer ports of the cartridge, and transferring, via the connected sterile liquid transfer ports, fluid between the fluid device and the cartridge. In some variations, the method may further include sterilizing internal surfaces of the connected sterile liquid transfer ports prior to transferring the fluid. In some variations, the method may further include actuating a cap actuator configured to translate caps of each of the connected sterile liquid transfer ports to open a flow path at an interface of the connected sterile liquid transfer ports. In some variations, the method may further include engaging a peristaltic pump of a first portion of the system with a compressible fluidic tubing of a fluid pump module of the fluid device. The engaging may include moving a pneumatic actuator of the first portion of the system to translate the peristaltic pump relative to the compressible fluidic tubing of the fluid pump module, thereby adjusting an amount of occlusion of the compressible fluidic tubing. Movement of the pneumatic actuator may be performed until a predetermined pressure of fluid within the compressible fluidic tubing or a predetermined amount of occlusion of the compressible fluidic tubing is achieved. In some variations, the aligning may be based on data acquired by one or more sensors of the instrument head. In some variations, the aligning may include detecting at least one edge of the one of the plurality of sterile liquid transfer ports of the cartridge using data acquired by the one or more sensors. The detection of the at least one edge may include detecting a plurality of points on the one of the plurality of sterile liquid transfer ports of the cartridge. The plurality of points may include two locations each along three edges of the one of the plurality of sterile liquid transfer ports of the cartridge. In some variations, the method may further include receiving a cartridge into a docking station of a second portion of the system. In some variations, the method may further include securing a position of the cartridge within the docking station. The securing the position of the cartridge within the docking station may include raising a floating platform on which the cartridge is seated to bring the cartridge into contact with a clamping surface of the docking station. In some variations, the method may further include performing flow fidelity testing prior to transferring the fluid. In some variations, the method may further include estimating, based on data acquired by one or more sensors of the instrument head, a flow rate of fluid transfer. The estimating the flow rate of fluid transfer may be used to calibrate a volumetric flow rate based on a revolution of a peristaltic pump of the system. In some variations, the method may further include estimating a rate of fluid flow within the fluid device based on data from a first sensor of the instrument head and a second sensor of the instrument head, wherein each of the first sensor and the second sensor are configured to view a respective portion of a fluid conduit of the fluid device. The estimating may further include receiving data from the first sensor indicating an air to liquid transition within a first portion of the fluid conduit, receiving data from the second sensor indicating an air to liquid transition within a second portion of the fluid conduit, and calculating the estimated rate of fluid flow based on a diameter of the fluid conduit between the first sensor and the second sensor, a length of the fluid conduit between the first sensor and the second sensor, and an elapsed time between when the air to liquid transition was indicated at the first sensor and when the air to liquid transition was indicated at the second sensor. In some variations, the method may further include calibrating the peristaltic pump based on the estimated rate of fluid flow. The engaging may include moving a pneumatic actuator of the first portion of the system to translate the peristaltic pump relative to the compressible fluidic tubing of the fluid pump module, thereby adjusting an amount of occlusion of the compressible fluidic tubing, and the method may further include adjusting, based on the estimated rate of fluid flow, a position of the peristaltic pump of the first portion of the system to adjust the amount of occlusion of the compressible fluidic tubing. In some variations, the method may further include adjusting a rate of rotation of a rotor of the peristaltic pump based on the estimated rate of fluid flow.

In other variations, methods for fluid transfer between the fluid device and the cartridge for cell processing may include receiving, by an instrument head of a first portion of a system, a fluid device including a sterile liquid transfer port, receiving, by a second portion of the system, a cartridge within a docking station, the cartridge including a plurality of sterile liquid transfer ports, connecting the sterile liquid transfer port of the fluid device to one of the plurality of sterile liquid transfer ports of the cartridge, adjusting a position of a pneumatic actuator of the instrument head relative to a fluid pump module of the fluid device, thereby modifying a distance between a peristaltic pump of the instrument head and compressible fluidic tubing of the fluid pump module, and transferring, via the connected sterile liquid transfer ports and after a predetermined fluid pressure is achieved within the compressible fluidic tubing, fluid between the fluid device and the cartridge.

In other variations, methods for fluid transfer between the fluid device and the cartridge for cell processing may include receiving, by an instrument head of a first portion of a system, a fluid device including a sterile liquid transfer port, receiving, by a second portion of the system, a cartridge within a docking station, the cartridge including a plurality of sterile liquid transfer ports, connecting the sterile liquid transfer port of the fluid device to one of the plurality of sterile liquid transfer ports of the cartridge, adjusting a position of a pneumatic actuator of the instrument head relative to a fluid pump module of the fluid device, thereby modifying a distance between a peristaltic pump of the instrument head and compressible fluidic tubing of the fluid pump module, and transferring, via the connected sterile liquid transfer ports and after a predetermined occlusion is achieved within the compressible fluidic tubing, fluid between the fluid device and the cartridge.

Additional variations, features, and advantages of the invention will be apparent from the following detailed description and through practice of the invention.

BRIEF DESCRIPTION OF THE DRAWINGS

FIG. 5C is a rendering of an illustrative variation of a second portion of a sterile liquid transfer system. FIG. 5D is a rendering of an illustrative variation of an aspect of a second portion of a sterile liquid transfer system. FIG. 5E is a rendering of an illustrative variation of an aspect of a second portion of a sterile liquid transfer system.

FIG. 8 is a flow diagram of an illustrative method for automated fluid transfer within a sterile liquid transfer system.

FIGS. 12A-12C are renderings of aspects of a first portion of a sterile liquid transfer system of an illustrative variation of a sterile liquid transfer system during a step of an illustrative method for automated fluid transfer within a sterile liquid transfer system.

DETAILED DESCRIPTION

A limiting factor in cell therapy manufacturing is the absence of automated systems, devices, and methods for performing fluid transfer without contamination and/or introducing human error.

Accordingly, the present disclosure provides systems, devices, and methods for automated fluid transfer within an automated cell processing system in an effort to maximize sterility and enable the availability of manufactured cell therapies at scale.

Figure 2A:
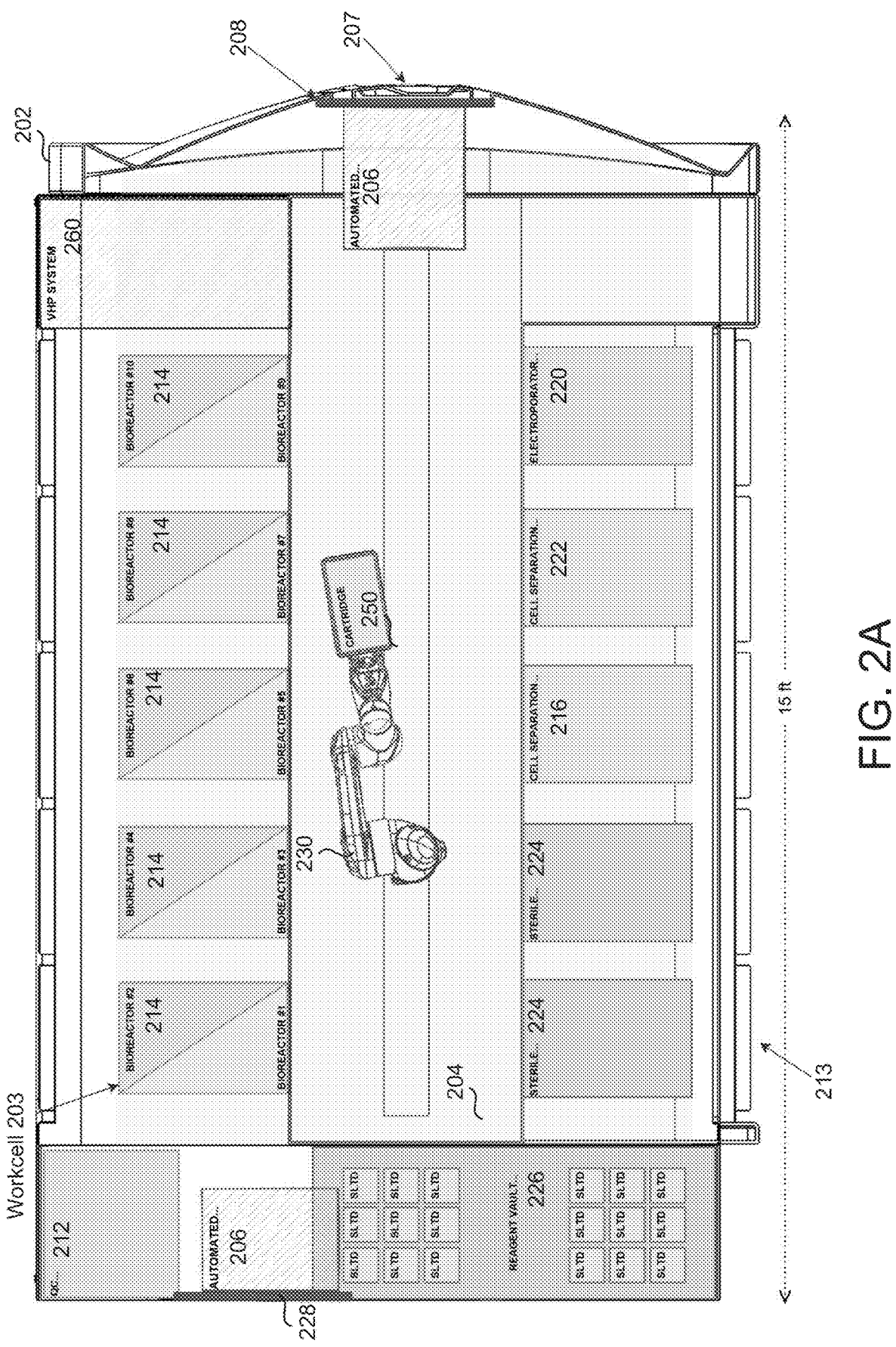
FIG. 2A is a block diagram of an illustrative variation of a cell processing system.
Figure 2B:
FIG. 2B is a perspective view of an illustrative variation of a workcell of a cell processing system.

The systems, devices, and methods for performing fluid transfer described herein are for use with a cell therapy manufacturing system, or cell processing system, an exemplary illustration of which is shown in FIG. 2B. As shown in FIG. 2B, cell processing may involve moving a cartridge 250 containing a cell product between a plurality of instruments, such as instruments 211, 216, 220, 222, inside a workcell 202. One or more of the instruments may be configured to couple, engage, or interface with the cartridge 250 to perform cell processing steps on cells within the cartridge 250. In some variations, a plurality of cell processing steps may be performed within the cartridge 250. For example, a robotic arm 230 may be configured to move the cartridge 250 between instruments, each instrument configured to perform a different cell processing step when coupled to a corresponding module within the cartridge 250. In some variations, the cartridge 250 may include any number of modules, such as a bioreactor module, a counterflow centrifugal elutriation (CCE) module, a magnetic cell sorter module, an electroporation module, a sorting module (e.g., fluorescence activated cell sorting (FACS) module), an acoustic flow cell module, a microfluidic enrichment module, a spinoculation module, and/or combinations thereof, and the like. In some variations, the workcell 202 may process two or more cartridges in parallel. For example, the workcell 202 may include a plurality of instruments, such as instruments 211, 216, 220, 222, having receiving bays. Each instrument may be configured to interface with a cartridge, such as cartridge 250, received within a respective receiving bay, such that multiple instruments within the workcell 202 may be in use at any given time.

Further to and enabling the above cell processing steps, the automated cell processing system may facilitate automated fluid transfers (which may or may not be sterile fluid transfers) between the cartridge and instruments or other components of the system, such as other cartridges and/or sample collection vessels, reagent vessels, waste vessels, other fluid devices, and the like. For example, as will be described below, the systems, devices, and methods of the present disclosure may facilitate fluid transfer between the cartridge and a fluid device, which may be a reagent vessel, a sample collection vessel, a waste vessel, and the like.

1. Cell Processing System

Figure 1A:
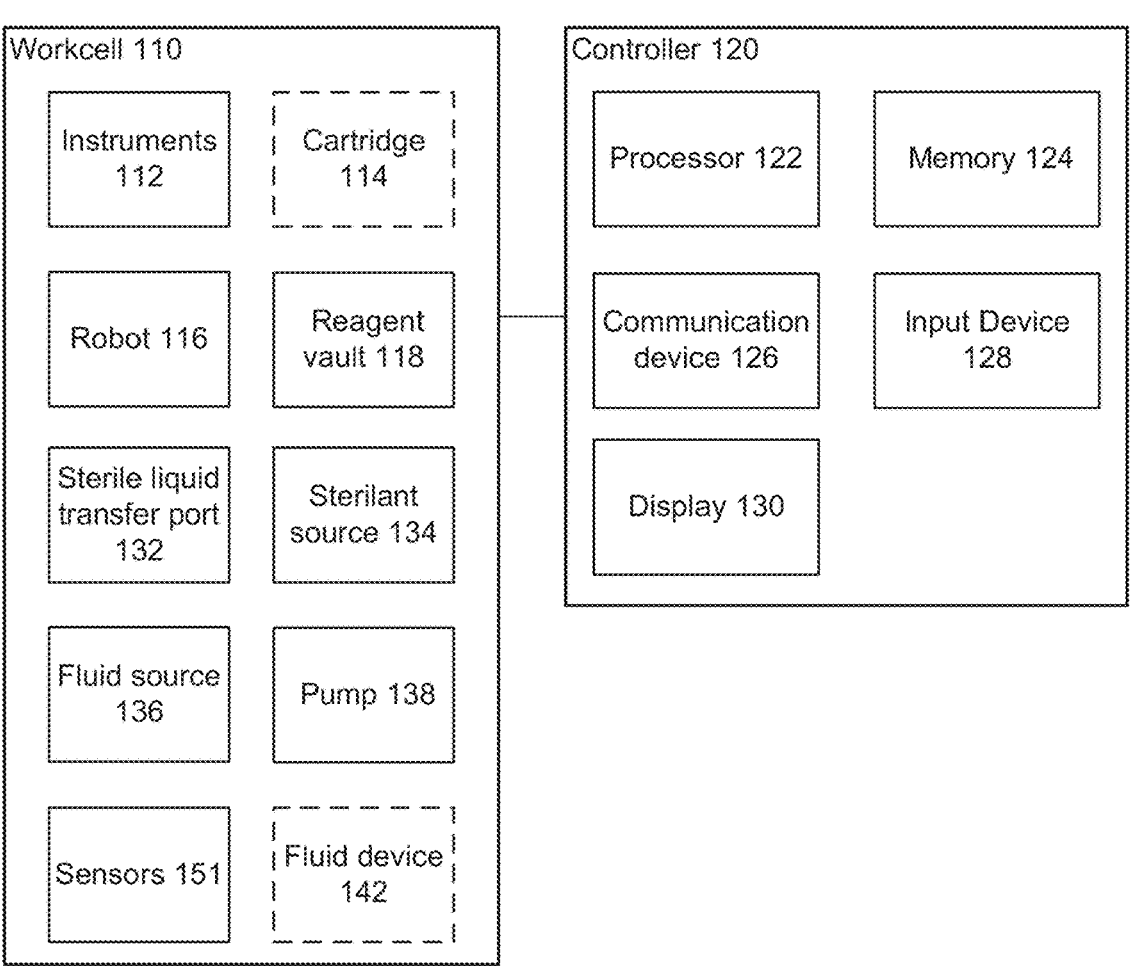
FIG. 1A is a block diagram of an illustrative variation of a cell processing system.

An illustrative cell processing system for use with the automated fluid transfer devices, systems, and methods is shown in FIG. 1A. Shown there is a block diagram of a cell processing system 100 comprising a workcell 110 and controller 120. The workcell 110 may comprise one or more of an instrument 112, a robot 116 (e.g., robotic arm), a reagent vault 118, a sterile liquid transfer port 132, a sterilant source 129, a fluid source 136, a pump 138, and a sensor(s) 151. A cartridge 114 and a fluid device 142, which may be provided outside of the workcell 110 and used within used within the workcell 110, are illustrated in dashed lines. In some variations, the fluid device 142 is a sterile liquid transfer device (SLTD). However, it should be appreciated that the fluid device 142 may be configured to transfer any fluid (which includes liquids), whether sterile or not. The controller 120 may comprise one or more of a processor 122, a memory 124, a communication device 126, an input device 128, and a display 130.

The workcell 110 may comprise a fully, or at least partially, enclosed housing inside which one or more cell processing steps are performed in a fully, or at least partially, automated process. In some variations, the workcell may be an open system lacking an enclosure, which may be configured for use in a clean room, a biosafety cabinet, or other sterile location. The cartridge 114 may be moved using the robot 116 to reduce manual labor in the cell processing steps, and fluid transfers into and out of the cartridge may also be performed in a fully or partially automated process, as will be described in detail herein. For example, one or more fluids may be stored in a fluid device 142. In some variations, the fluid device is able to be moved within the system 100 by the robot 116. The fluid devices and sterile liquid transfer ports described herein advantageously enable the transfer of fluids in an automated and metered manner for automating cell therapy manufacturing.

In some variations, the robot 116 is configured to move cartridges 114 between different instruments to perform a predetermined sequence of cell processing steps. In this way, multiple cartridges 114 may be processed in parallel, as different steps of the cell processing sequence may be performed at the same time on different cartridges.

A sterile liquid transfer port 132 may be coupled between two or more cartridges 114 to transfer a cell product and/or fluid between the cartridges 114. Furthermore, a sterile liquid transfer port 132 may be coupled between any set of fluid-carrying components of the system 100 (e.g., cartridge 114, reagent vault 118, fluid source 136, fluid device 142, etc.). For example, a first sterile liquid transfer port may be coupled between a first cartridge and a corresponding sterile liquid transfer port of a fluid device.

In some variations, a reagent vault 118 (or reagent vaults) is used to store reagents, including but not limited to cell culture media, buffer, cytokines, proteins, enzymes, polynucleotides, transfection reagents, non-viral vectors, viral vectors, antibiotics, nutrients, cryoprotectants, solvents, cellular materials, and pharmaceutically acceptable excipients. Additionally, or alternatively, waste may be stored in the reagent vault, or within a fluid device within the reagent vault. In some variations, in-process samples extracted from one or more cartridges may be stored in the reagent vault, or in a fluid device within the reagent vault. The reagent vault may comprise one or more controlled temperature compartments (e.g., freezers, coolers, water baths, warming chambers, or others, at e.g., about −80° C., about −20° C., about 4° C., about 25° C., about 30° C., about 37° C., and about 42° C.). Temperatures in these compartments may be varied during the cell manufacturing process to heat or cool reagents.

In some variations, the reagents, waste, and/or extracted in-process samples, among others, may be stored within fluid devices 142 within the reagent vault 118. To this end, the fluid devices 142 may be transferred to a cartridge within the workcell or a cartridge may be moved by the robot 116 (or manually by an operator) to the reagent vault 118. The reagent vault 118 can interface with one or more sterile liquid transfer ports on the cartridge, and the reagent or material may be transferred from a fluid device 142 within the reagent vault into the cartridge. Optionally, fluid is added or removed from the cartridge before, during, or after addition or removal of the reagent or material. In some variations, the instruments 112 of the workcell 110 comprise a sterile liquid transfer system, which may also be referred to herein as a sterile liquid transfer instrument, similarly configured to transfer fluid into or out of the cartridge in an automated fashion. The sterile liquid transfer instrument may be stocked with reagents by, for example, a robot 116 that moves fluid devices 142 comprising the reagents from a workcell feedthrough or other location to the sterile liquid transfer instrument. In some variations, the robot 116 moves a fluid device(s) 142 from the reagent vault 118 to the sterile liquid transfer instrument. The reagent vault 118 may have automated doors to permit access by the robot 116 to a fluid device(s) 142 stored therein. The fluid device(s) 142 may be configured for pick-and-place movement by the robot 116. In some variations, the reagent vault 118 may comprise one or more sample pickup areas. For example, the robot 116 may be configured to move one or more fluid devices 142 comprising reagents to and from one or more of the sample pickup areas.

In some variations, the sensor(s) 151 of the workcell 110 comprise optical sensors proximate to aspects of a sterile liquid transfer instrument. The sensor(s) 151 may be used during an automated fluid transfer procedure to aid in the controlled flow of fluids from the fluid device to another fluid device or to a cartridge. In particular, the optical sensors can be arranged with a view to windows of the fluid device to detect the presence or absence of fluid within fluid conduits of the fluid device. In this way, the controller 120 can deliver metered amounts of fluid from the fluid device to an adjoined fluid device or cartridge.

Figure 1B:
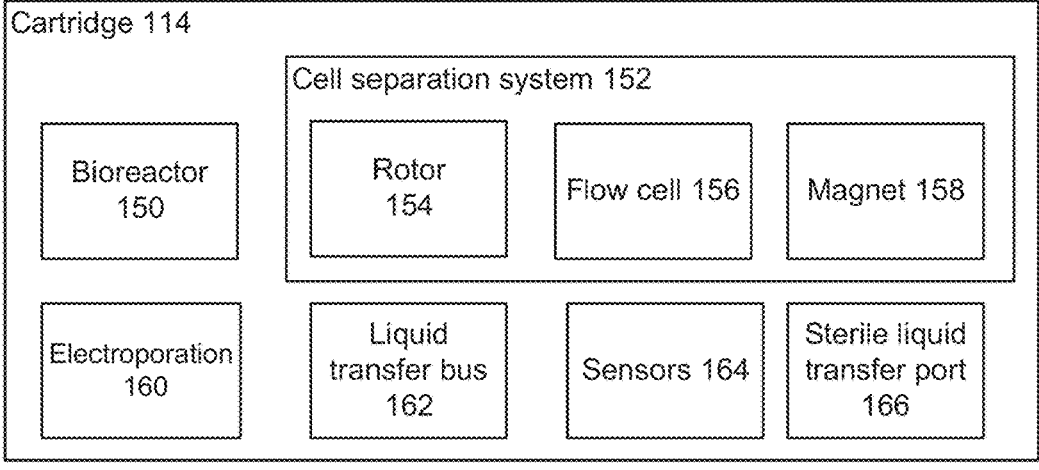
FIG. 1B is a block diagram of an illustrative variation of a cartridge.

As illustrated in FIG. 1B, a cartridge 114 may comprise one or more of a bioreactor 150, a cell separation system 152, an electroporation module 160, a fluid transfer bus 162, a sensor(s) 164, and a sterile liquid transfer port 166, as described in more detail herein. A cell separation system 152 may comprise one or more of a rotor 154, flow cell 156, and magnet 158. In some variations, the magnet 158 may comprise one or more magnets and/or magnet arrays. For example, the cell separation system 152 may comprise a first magnet configured to magnetically rotate a rotor 154 and a second magnet (e.g., magnet array) configured to magnetically separate cells in flow cell 156.

Any suitable cell processing may be performed using the systems and devices described herein, and may include steps such as growing, enriching, selecting, sorting, expanding, activating, transducing, electroporating, washing, and the like. In some variations, a method of processing a solution containing a cell product includes the steps of digesting tissue using an enzyme reagent to release a select cell population into solution, enriching cells using a CCE instrument, washing cells using the CCE instrument, selecting cells in the solution using a selection instrument, sorting cells in the solution using a sorting instrument, differentiating or expanding the cells in a bioreactor, activating cells using an activating reagent, electroporating cells, transducing cells using a vector, and finishing a cell product.

Figure 2C:
FIG. 2C is a perspective view of an illustrative variation of a workcell and cartridge of a cell processing system.

FIG. 2A shows an illustrative cell processing system for use with the devices, systems, and methods described herein. Shown there is workcell 203. The workcell may be divided into an interior zone 204 with a feedthrough 206 access, and quality control (QC) instrumentation 212. An air filtration inlet (not shown) may provide high-efficiency particulate air (HEPA) filtration to provide ISO7 or better air quality in the interior zone 204. In some embodiments, this air filtration may maintain sterile cell processing in an ISO8 or ISO9 manufacturing environment. The workcell 203 may also have an air filter on the air outlet to preserve the ISO rating of the room. Similar to the workcell described above in reference to FIG. 1A, the workcell 203 may further comprise, inside the interior zone 104, a bioreactor instrument 214, a cell selection instrument 216 (e.g., a magnetic separation instrument), an electroporation instrument 220, a counterflow centrifugation elutriation (CCE) instrument 222, a sterile liquid transfer instrument 224 (e.g., for facilitating automated fluid transfers), a reagent vault 226, and a sterilization system 260. The reagent vault 226 may be accessible by a user through a sample pickup port 228. A robot 230 (e.g., support arm, robotic arm, etc.) may be configured to move one or more cartridges 250 from any instrument to any other instrument, move one or more cartridges 250 to and from the reagent vault 226, and/or move one or more fluid devices between the reagent vault 226 and the sterile liquid transfer instrument 224. In some variations, the workcell 203 may comprise one or more moveable barriers 213 (e.g., access, door) configured to facilitate access to one or more of the instruments in the workcell 203. FIG. 2B is a perspective view of a workcell 205 of a cell processing system. FIG. 2C is a perspective view of a cell processing system depicting a cartridge 250 introduced into a workcell 205. A plurality of cartridges may be inserted into the workcell 205 and undergo one or more cell processing operations in parallel.

Figure 2D:
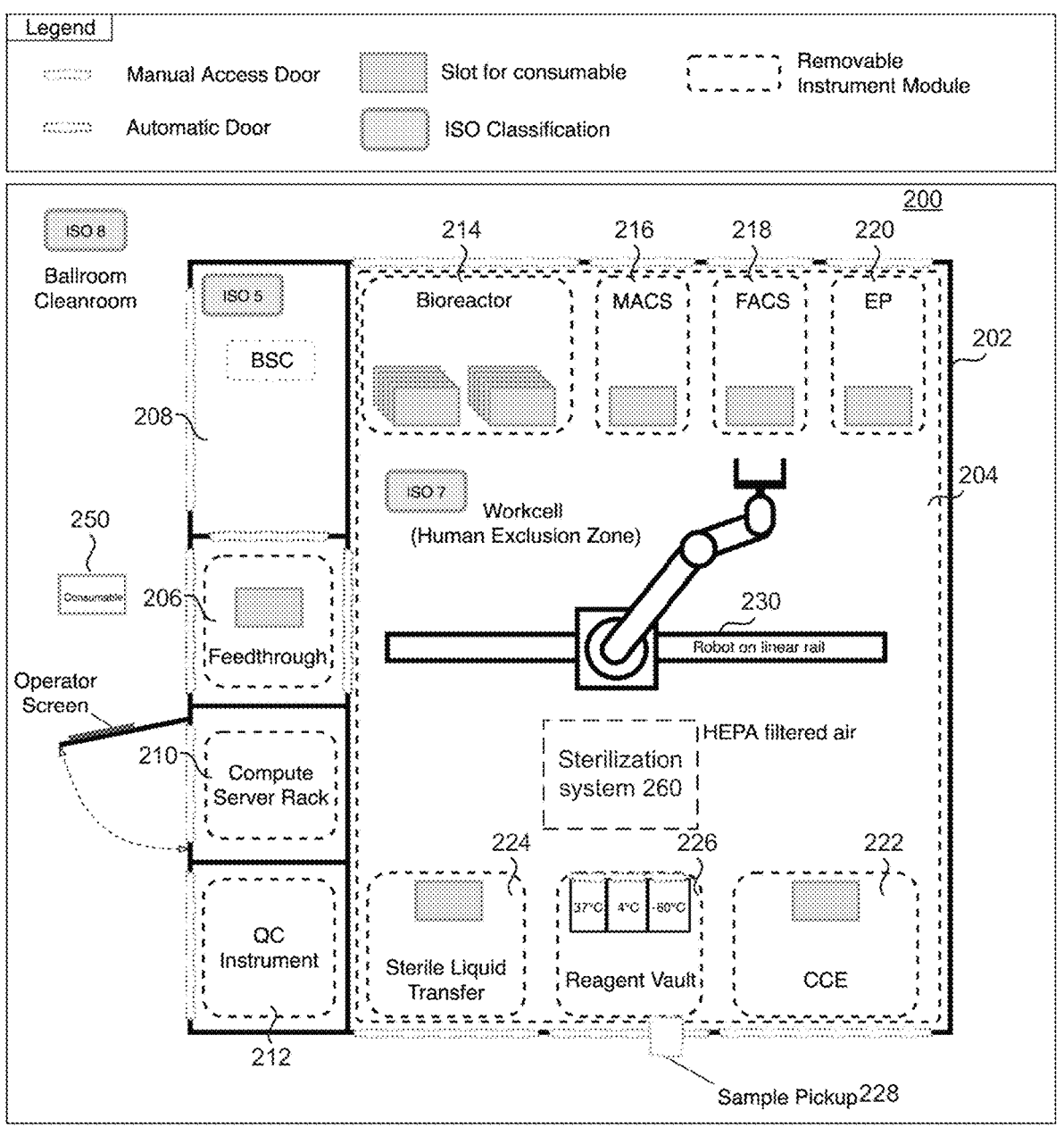
FIG. 2D is a block diagram of an illustrative variation of a cell processing system.

FIG. 2D is a schematic illustration of an embodiment of a workcell 200. Workcell 200 may comprise an enclosure 202 having four walls, a base, and a roof. The workcell 200 may be divided into an interior zone 204 with a feedthrough 206 access, a biosafety cabinet (BSC) 208, compute server rack 210 (e.g., controller 120), and quality control (QC) instrumentation 212. An air filtration inlet (not shown) may provide high-efficiency particulate air (HEPA) filtration to provide ISO7 or better air quality in the interior zone 204. The workcell 200 may also have an air filter on the air outlet to preserve the ISO rating of the room. As with the workcell described above, workcell 200 may further comprise, inside the interior zone 204, an instrument 211 (e.g., disposed in a universal instrument bay), a bioreactor instrument 214, a cell selection instrument 216 (e.g., magnetic separation instrument, cell selection system), a cell sorting instrument 218 (e.g., FACS), an electroporation instrument 220, a counterflow centrifugation elutriation (CCE) instrument 222, and a sterile liquid transfer instrument 224, alongside a reagent vault 226 and a sterilization system 260 comprising one or more of a sterilant source, fluid source, and a pump. As will be described below, the sterilization system 260 may be connectable to a fluid device for sterilization of a sterile liquid transfer port during an automated fluid transfer process. The reagent vault 226 may be accessible through a sample pickup port 228. A robot 230 (e.g., support arm, robotic arm) may be configured to move one or more cartridges 250 from any instrument to any other instrument, move one or more cartridges 250 to and from the reagent vault 226, and/or move one or more fluid devices between the reagent vault 226 and the sterile liquid transfer instrument 224.

In some variations, a human operator may load one or more cartridges 250 into the feedthrough 206. The cartridges 250 may be pre-sterilized, or the feedthrough 206 may sterilize the cartridge 250 using ultraviolet radiation (UV) or chemical sterilizing agents provided as a spray or wash. The feedthrough 206 chamber may optionally be configured to automatically spray, wash, irradiate, or otherwise treat cartridges (e.g., with ethanol and/or isopropyl alcohol solutions) to maintain sterility of the interior zone 204 (e.g., ISO 7 or better) or the biosafety cabinet 208 (e.g., ISO 5 or better). The cartridge 250 may be passed to the biosafety cabinet 208, where input cell product is provided and loaded to the cartridge 250. The user may then move the cartridge 250 back to the feedthrough 206 and initiate automated cell processing using a computer processor in the computer server rack 210 (e.g., controller 120). The robot 230 may be configured to move the cartridge 250 in a predefined sequence to a plurality of instruments and stations, with the components of the workcell 200 being controlled by the computer processor of the computer server rack 210.

Figure 2E:
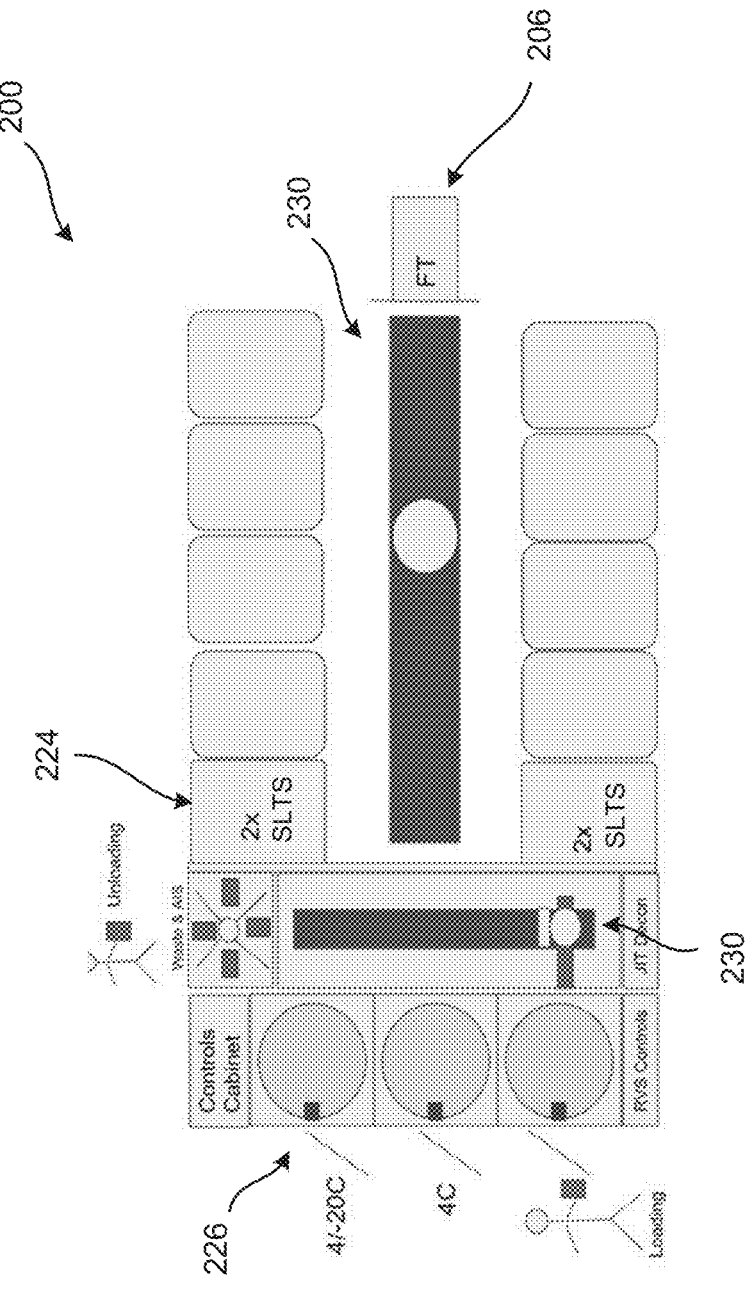
FIG. 2E is a block diagram of an illustrative variation of a cell processing system, comprising an arrangement of sterile liquid transfer systems, or sterile liquid transfer instruments (SLTIs).

FIG. 2E shows an illustrative cell processing system for use with the devices, systems, and methods described herein. In some variations, a workcell 200 includes robot(s) 230 of a material handling system of the workcell 200. In some variations, a human operator may load one or more cartridges into the feedthrough 206. The workcell 200 may be divided into an interior zone with a feedthrough 206 access, a controls cabinet, reagent vault system (RVS) controls, just in time (JIT) decontamination, and a waste and analytical instrument system (AIS). As with the workcell described above, workcell 200 may further comprise a plurality of instruments 211 (e.g., disposed in a universal instrument bay), such as a bioreactor instrument, a cell selection instrument (e.g., magnetic separation instrument, cell selection system), a cell sorting instrument (e.g., FACS), an electroporation instrument, a counterflow centrifugation elutriation (CCE) instrument, and a sterile liquid transfer instrument, alongside a reagent vault 226 and a sterilization system 260, which may include JIT contamination, comprising one or more of a sterilant source, fluid source, and a pump. As will be described below, the sterilization system 260 may be connectable to a fluid device for sterilization of a sterile liquid transfer port during an automated fluid transfer process. The reagent vault 226 may be accessible through a sample pickup port during loading and/or unloading. A robot 230 (e.g., support arm, robotic arm) may be configured to move one or more cartridges from any instrument to any other instrument, move one or more cartridges to and from the reagent vault 226, move one or more cartridges to and from a sterile liquid transfer instrument 224, and/or move one or more fluid devices between the reagent vault 226 and the sterile liquid transfer system 224. The sterile liquid transfer instrument 224 will be described in more detail below.

Figure 2F:
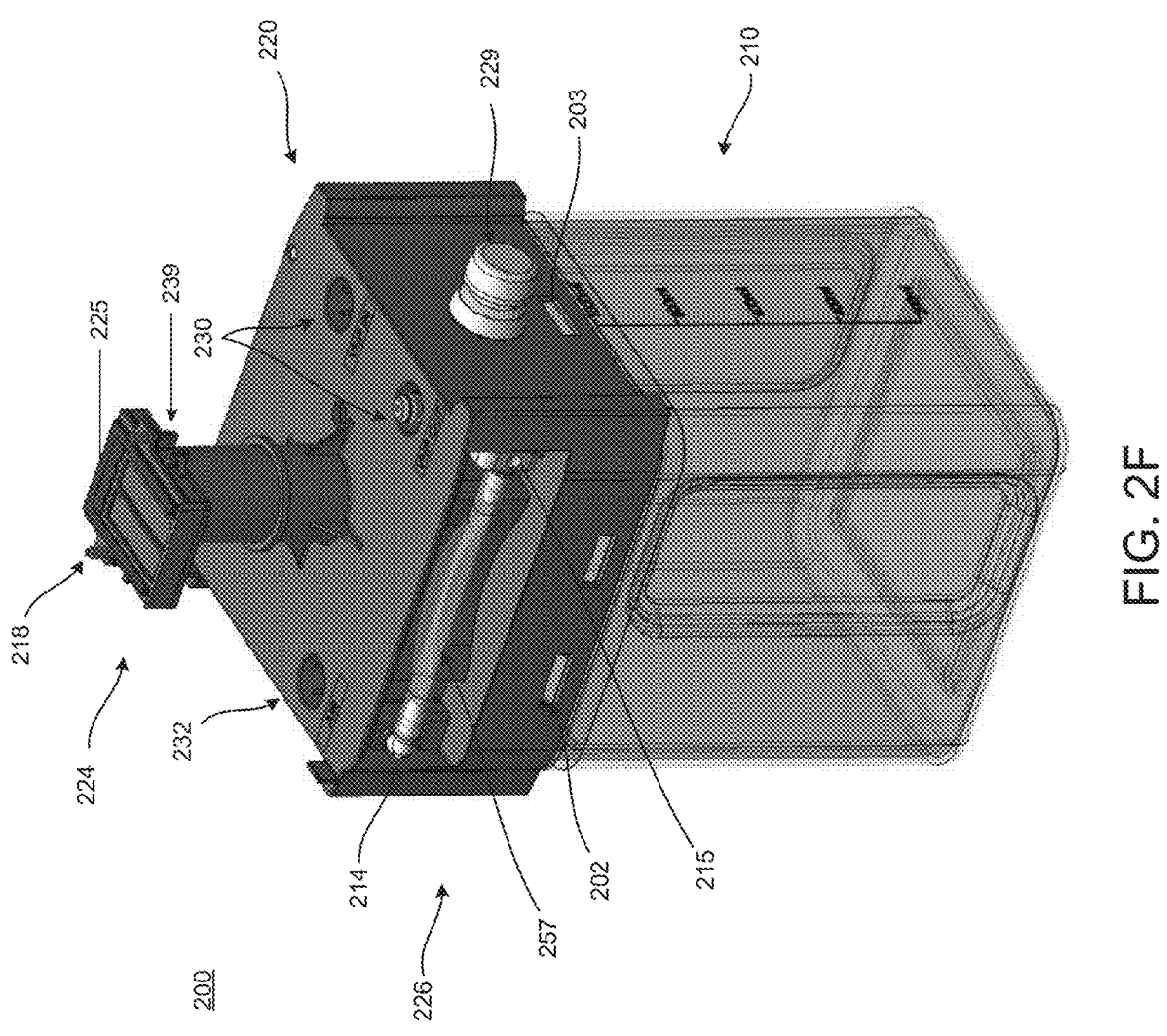
FIG. 2F is a rendering of an illustrative variation of a fluid device.
Figure 2G:
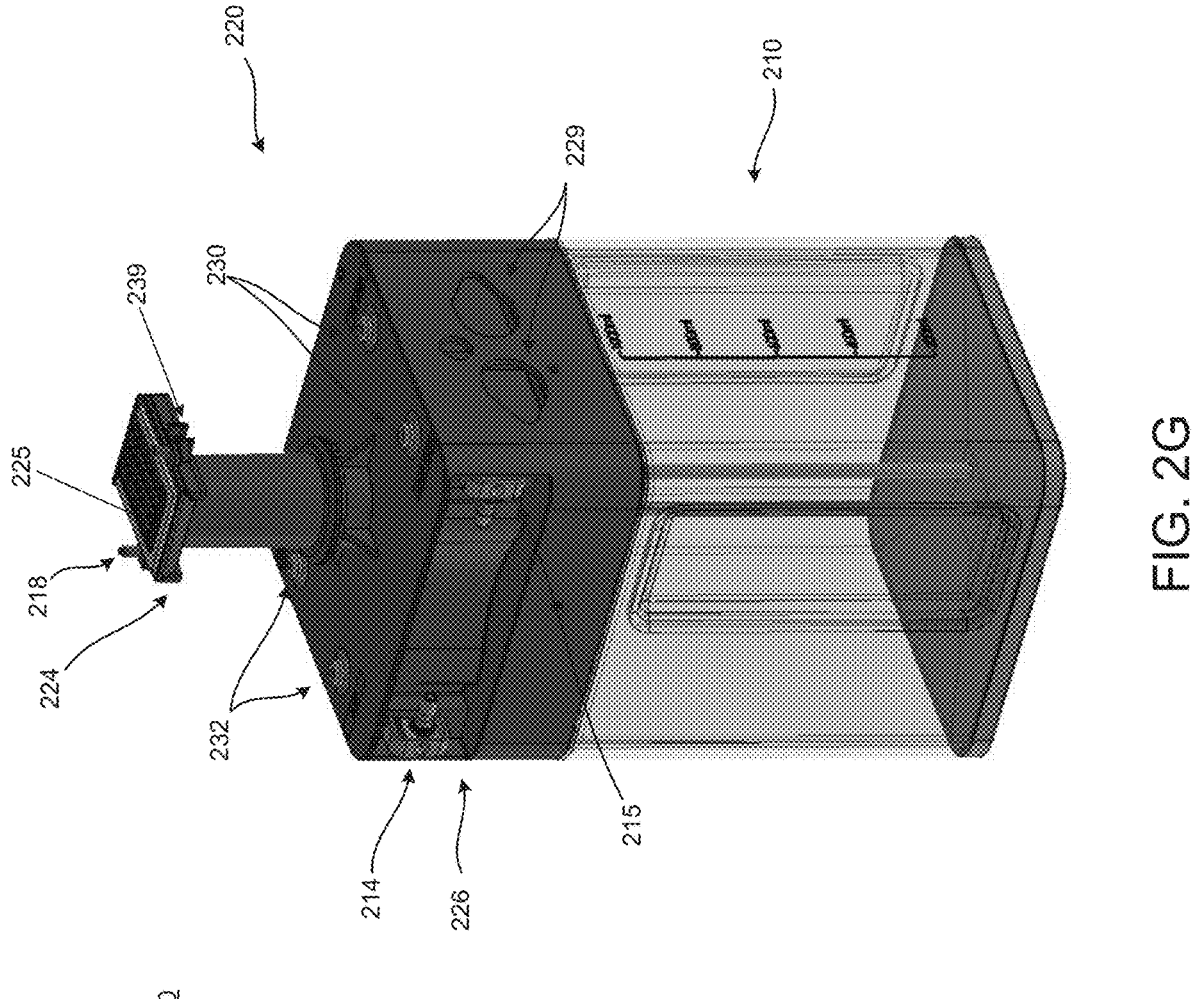
FIG. 2G is a rendering of an illustrative variation of a fluid device.

Turning now to FIG. 2F and FIG. 2G, renderings illustrative fluid devices for automated fluid transfer are provided.

In some embodiments, and as shown in FIG. 2F, a fluid device 200 comprises a container 210 and a collar 220. The collar 220 may comprise one or more robot engagement features such as protrusion 229, as well as fluid conduits, a sterile liquid transfer port 224 having a mechanical seal 225, at least one container coupling feature 202 couplable to a corresponding one of the at least one collar coupling feature 203 of the container 210, at least one viewing window, a fluid pump module 226 having compressible fluidic tubing 267, a plurality of ports including sterilization process port(s) 230 and at least one air process port 232, and a fluid access port.

In some variations, the compressible fluidic tubing 257 may be coupled between an outlet port 215 of the collar 220 which delivers fluid to the compressible fluidic tubing 257 and an inlet port 214 of the collar 220 which returns the fluid to the fluid conduits of the collar 220. The compressible fluidic tubing 257 may be proximate an external surface of the collar 220 so that an end effector of the workcell may interact with the compressible fluidic tubing 257 to move fluid therein. For example, the external surface of the collar 220 may be curved proximate the compressible fluidic tubing 257 so that a cam of the workcell may compress the compressible fluidic tubing 257. The cam may be a rotor and bearings of a peristaltic pump and the curved external surface of the collar 220 may be a track such that bearings of the peristaltic pump engage the compressible fluidic tubing within the track.

In some variations, the sterile liquid transfer port 224 of the collar 220 may comprise at least one of a port and a valve and may form one part of a sterile fluid pathway between the fluid device 200 and a cartridge to enable sterile, automated, and precisely metered (e.g., precise control of a transferred fluid volume) fluid transfer. The sterile liquid transfer port 224 may comprise a mechanical seal 225. The mechanical seal 225 helps provide sterility of a fluid transfer pathway between the fluid device 200 and the cartridge. In some variations, as will be described herein, a robot of a sterile liquid transfer instrument may be configured to manipulate the fluid device 200 via protrusion(s) and alignment features 218 of the sterile liquid transfer port 224 to couple the fluid device 200 to the cartridge. Further, the robot may be configured to operate the sterile liquid transfer port 224 to open and close a set of ports and valves thereof, including the at least one of the port, to permit fluid flow between the fluid device 200 and the cartridge.

In some variations, the sterile liquid transfer port 224 comprises a detent engagement feature 239 configured to be engaged by a corresponding detent of a sterile liquid transfer port cap actuator end effector, as will be described later with reference to FIG. 6A through FIG. 6D.

In some variations, the sterilization process ports 230 may be configured to deliver sterilant (e.g., vaporized hydrogen peroxide ("VHP")) from a sterilant source within the workcell to the fluid conduits and the sterile liquid transfer port 224 of the collar 220. In some variations, the at least one air process port 232 may provide a pathway for air to enter or leave the fluid device 200 during filling of the container 210 and/or depleting of the container 210. In some variations, the at least one air process port 232 may be connected to an air source (e.g., atmospheric air). In some variations, the air source may comprise compressed air, which can be used to purge the fluid conduits 222 of the collar 220 before and/or after fluid transfer therethrough.

In some variations, and as in FIG. 2G, a fluid device 200 comprises a container 210 and a collar 220. The collar 220 may comprise one or more robot engagement features such as depression(s) 229, as well as fluid conduits, a sterile liquid transfer port 224 having a mechanical seal 225, a fluid transport feature couplable to an opening of the container 210, at least one container coupling feature couplable to a corresponding one of the at least one collar coupling feature of the container 210, at least one viewing window, a fluid pump module 226 having compressible fluidic tubing, a plurality of ports including sterilization process port(s) 230 and at least one air process port 232, and a fluid access port.

In some variations, the compressible fluidic tubing (not shown) may be coupled between an outlet port 215 of the collar 220 which delivers fluid to the compressible fluidic tubing and an inlet port 214 of the collar 220 which returns the fluid to the fluid conduits of the collar 220.

In some variations, the sterile liquid transfer port 224 of the collar 220 may comprise at least one of a port and a valve (not shown) and may form one part of a sterile fluid pathway between the fluid device 200 and a cartridge to enable sterile, fully automated, and precisely metered (e.g., precise control of a transferred fluid volume) fluid transfer. The sterile liquid transfer port 224 may comprise a mechanical seal 225. The mechanical seal 225 may help provide sterility of a fluid transfer pathway between the fluid device 200 and the cartridge. In some variations, a robot of a sterile liquid transfer instrument may be configured to manipulate the fluid device 200 via the depression(s) 229 and alignment features 218 of the sterile liquid transfer port 224 to couple the fluid device 200 to the cartridge. Further, the robot may be configured to operate the sterile liquid transfer port 224 to open and close a set of ports and valves thereof, including the at least one of the port, to permit fluid flow between the fluid device 200 and the cartridge.

In some variations, the sterile liquid transfer port 224 comprises a detent engagement feature 239 configured to be engaged by a corresponding detent of a sterile liquid transfer port cap actuator end effector, as will be described later with reference to FIG. 6A through FIG. 6D.

In some variations, the sterilization process ports 230 may be configured to deliver sterilant (e.g., vaporized hydrogen peroxide ("VHP")) from a sterilant source within the workcell to the fluid conduits and the sterile liquid transfer port 224 of the collar 220. In some variations, the at least one air process port 232 may provide a pathway for air to enter or leave the fluid device 200 during filling of the container 210 and/or depleting of the container 210. In some variations, the at least one air process port 232 may be connected to an air source (e.g., atmospheric air). In some variations, the air source may comprise compressed air, which can be used to purge the fluid conduits 222 of the collar 220 before and/or after fluid transfer therethrough.

Other suitable cell processing systems and aspects thereof, including fluid transfer via sterile liquid transfer ports, are provided e.g., in U.S. patent application Ser. No. 17/198,134, published as U.S. Patent Publication No. 2021/0283565, entitled "Systems and Methods for Cell Processing", and e.g., in U.S. patent application Ser. No. 18/620,826, entitled "Systems, Devices, and Methods for Fluid Transfer Within an Automated Cell Processing System", which are incorporated by reference herein.

A. Workcell i. Robot

Generally, a robot of the workcell may comprise any mechanical device capable of moving a cartridge and/or a fluid device from one location to another location within the workcell. For example, the robot may comprise a mechanical manipulator (e.g., an arm) in a fixed location, or attached to a linear rail, or a 2- or 3-dimensional rail system. While shown in some of the Figures as being fixed in place or with respect to a rail system, the robot need not be so. For example, in some variations, the robot comprises a wheeled device. Any number of robots may be used within the workcell, as described herein. For example, In some variations, the workcell comprises two or more robots of the same or different type (e.g., two robotic arms each independently configured for moving cartridges between instruments). The robot may also comprise an end effector for precise handling of different cartridges or fluid devices or for barcode scanning or radio-frequency identification tag (RFID) reading.

The robots for use with the cell processing systems described herein are capable of moving cartridges between slots or bays in the workcell so that the modules within the cartridge can couple to corresponding instruments within the workcell to perform different cell processing steps. Further, the robots for use with the cell processing systems described herein are capable of moving and manipulating fluid devices within the workcell. For instance, the robot may be capable of moving a reagent storing fluid device from a reagent vault of the workcell to a sterile liquid transfer instrument of the workcell so that automated fluid transfer between the reagent storing fluid device and a cartridge can be performed.

ii. Controller

In embodiments, a cell processing system 100 may comprise a controller 120 (e.g., computing device) comprising one or more of a processor 122, memory 124, communication device, 126, input device 128, and display 130. The controller 120 may be configured to control (e.g., operate) the workcell 110. The controller 120 may comprise a plurality of devices. For example, the workcell 110 may enclose one or more components of the controller 120 (e.g., processor 122, memory 124, communication device 126) while one or more components of the controller 120 may be provided remotely to the workcell 110 (e.g., input device 128, display 130).

iii. Processor

The processor (e.g., processor 122) described here may process data and/or other signals to control one or more components of the system. The processor may be configured to receive, process, compile, compute, store, access, read, write, and/or transmit data and/or other signals. Additionally, or alternatively, the processor may be configured to control one or more components of a device (e.g., console, touchscreen, personal computer, laptop, tablet, server).

In some variations, the processor may be configured to access or receive data and/or other signals from one or more of workcell 110, server, controller 120, and a storage medium (e.g., memory, flash drive, memory card, database). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including structured text, typescript, C, C++, C#, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

iv. Memory

The cell processing systems and devices described here may include a memory (e.g., memory 124) configured to store data and/or information. In some variations, the memory may include one or more of a random-access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with the device, such as image processing, image display, sensor data, data and/or signal transmission, data and/or signal reception, and/or communication. Some embodiments described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The computer code (also may be referred to as code or algorithm) may be those designed and constructed for the specific purpose or purposes. In some variations, the memory may be configured to store any received data and/or data generated by the controller and/or workcell. In some variations, the memory may be configured to store data temporarily or permanently.

v. Input Device

In some variations, the input device, for example, input device 128 may comprise or be coupled to a display. Input device may be any suitable device that is capable of receiving input from a user, for example, a keyboard, buttons, touch screen, etc. The input device may include at least one switch configured to generate a user input. For example, an input device may include a touch surface for a user to provide input (e.g., finger contact to the touch surface) corresponding to a user input. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In embodiments of an input device including at least one switch, a switch may have, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a user input. A microphone may receive audio data and recognize a user voice as a user input.

In some variations, the cell processing system may optionally include one or more output devices in addition to the display, such as, for example, an audio device and haptic device. An audio device may audibly output any system data, alarms, and/or notifications. For example, the audio device may output an audible alarm when a malfunction is detected. In some variations, an audio device may include at least one of a speaker, a piezoelectric audio device, a magnetostrictive speaker, and/or a digital speaker. In some variations, a user may communicate with other users using the audio device and a communication channel. For example, a user may form an audio communication channel (e.g., VoIP call).

vi. Communication Device

In some variations, the controller may include a communication device (e.g., communication device 126) configured to communicate with another controller and one or more databases. The communication device may be configured to connect the controller to another system (e.g., Internet, remote server, database, workcell) by wired or wireless connection. In some variations, the system may be in communication with other devices via one or more wired and/or wireless networks. In some variations, the communication device may include a radiofrequency receiver, transmitter, and/or optical (e.g., infrared) receiver and transmitter configured to communicate with one or more devices and/or networks. The communication device may communicate by wires and/or wirelessly.

vii. Display

Image data may be output on a display e.g., display 130) of a cell processing system. In some variations, a display may include at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

viii. Graphical User Interface

In some variations, as indicated above, a GUI may be configured for designing a process and monitoring a product. For example, the GUI may be a process design home page. The GUI may indicate that no processes have been selected or loaded. A create icon (e.g., "Create a Process") may be selectable for a user to begin a process design process. In some variations, one or more of the GUIs described herein may include a search bar.

B. Cartridge

The cell processing systems described herein may comprise one or more cartridges having one or more modules configured to interface with one or more instruments within the workcell. An exemplary cartridge was described with reference to FIG. 1B.

Various materials may be used to construct the cartridge and the cartridge housing, including metal, plastic, rubber, and/or glass, or combinations thereof. The cartridge, its components, and its housing may be molded, machined, extruded, 3D printed, or any combination thereof. The cartridge may contain components that are commercially available (e.g., tubing, valves, fittings)—these components may be attached or integrated with custom components or devices. The housing of the cartridge may constitute an additional layer of enclosure that further protects the sterility of the cell product.

In some variations, the cartridge modules may be comprised of distinct sections that are integrated in a fixed configuration within the cartridge. Additionally, or alternatively, the modules may be configurable or moveable within the cartridge, permitting various formats of cartridges to be assembled. For example, the cartridge can be a single, closed unit with fixed components for each module, or the cartridge may contain configurable modules coupled by configurable fluidic, mechanical, optical, and electrical connections. In some variations, one or more sub-cartridges, each containing a set of modules, may be used to perform various cell processing workflows. The modules may each be provided in a distinct housing or may be integrated into a cartridge or sub-cartridge with other modules. The disclosure generally shows modules as distinct groups of components for the sake of simplicity, but it should be noted that these modules may be arranged in any suitable configuration. For example, the components for different modules may be interspersed with each other such that each module is defined by the set of connected components that collectively perform a predetermined function. However, the components of each module may or may not be physically grouped within the cartridge. In some variations, multiple cartridges may be used to process a single cell product through transfer of the cell product from one cartridge to another cartridge of the same or different type and/or by splitting cell product into more cartridges and/or pooling multiple cell products into fewer cartridges.

Generally, each of the instruments within the workcell interfaces with its respective module or modules on the cartridge. For example, when a cartridge has an electroporation module, it is moved by the robot to the electroporation instrument within the workcell to perform electroporation on the cells within the cartridge. One advantage of such split module/instrument designs is that expensive components (e.g., motors, sensors, heaters, lasers, etc.) may be retained in the instruments of the system while less expensive components reside in the cartridge, which can be configured for single-use. The use of disposable cartridges may eliminate the need to sterilize cartridges between use. Furthermore, having multiple instruments within the workcell further helps allow for the parallel utilization of those instruments when multiple cartridges are used within the workcell. In contrast, most conventional semi-automated instruments have instrument components that sit idle and are incapable of simultaneous parallel use.

In some variations, the cartridge comprises a sterile liquid transfer port for fluid transfer into and out of the cartridge. In some variations, the cartridge comprises any number of sterile liquid transfer ports and any number or position of fluid paths between modules and the sterile liquid transfer ports.

The sterile liquid transfer ports described herein may form a sterile fluid pathway between a fluid device and a cartridge and/or a first cartridge and a second cartridge to enable fluid transfer that may be sterile, fully automated, and precisely metered (e.g., precise control of a transferred fluid volume). In some variations, the robot may be configured to operate the sterile liquid transfer port to open and close a set of ports and valves thereof to permit fluid flow between a fluid device and a cartridge and/or a first cartridge and a second cartridge. The use of a robot and controller to operate the sterile liquid transfer port may facilitate automation and sterility of a cell processing system.

Additional aspects of suitable cartridges are provided e.g., in U.S. patent application Ser. No. 17/198,134, published as U.S. Patent Publication No. 2021/0283565, entitled "Systems and Methods for Cell Processing", which was previously incorporated by reference herein.

C. Sterile Liquid Transfer System for Automated Fluid Transfer

Generally, the sterile liquid transfer systems described herein may be configured for the automated transfer of fluid between a fluid device and a cartridge, such as fluid devices described above and with reference to FIG. 2F and FIG. 2G. In a workcell, a sterile liquid transfer system may be one of a plurality of instruments and a robot of a material handling system of the workcell can move cartridges between the sterile liquid transfer system and other ones of the plurality of instruments within the workcell. Cartridges may be moved to the sterile liquid transfer system, and fluid devices may be separately moved to the sterile liquid transfer system, as will be described herein, in order to allow for addition of reagents, biological materials, and the like to the cartridge as well as the removal of reagents, waste, biological materials (e.g., samples), and the like from the cartridge.

Figure 3A:
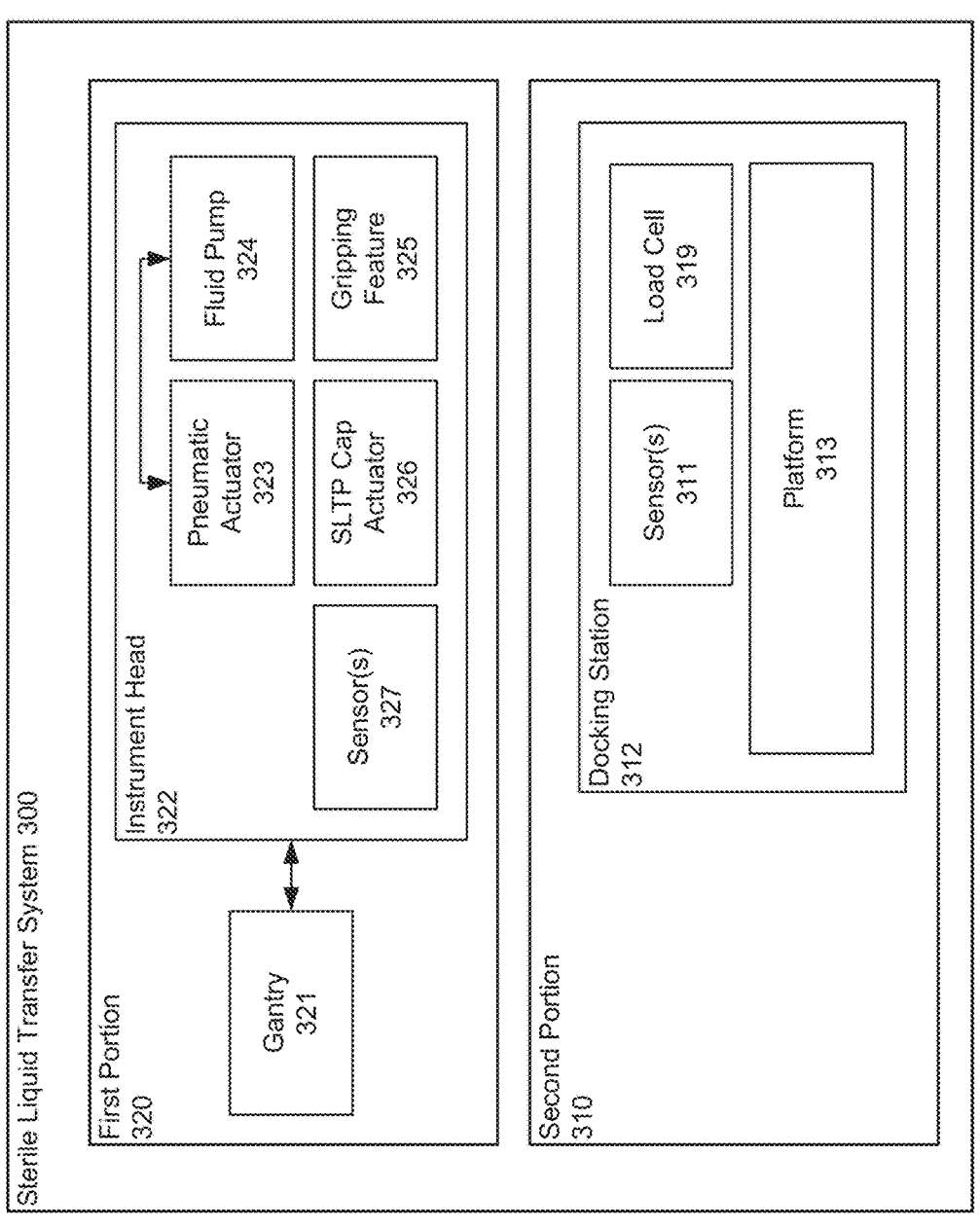
FIG. 3A is a schematic diagram of an illustrative variation of a sterile liquid transfer system.

Turning now to FIG. 3A, a schematic diagram of an illustrative variation of a sterile liquid transfer system 300, referred to above in certain instances as a sterile liquid transfer instrument, is shown.

In some variations, the sterile liquid transfer system 300 may comprise a first portion 320 and a second portion 310. As will be described with reference to FIG. 3B, the first portion 320 may be configured to receive a fluid device from a reagent vault system and the second portion 310 may be configured to receive a cartridge from the workcell via one or more robots of a material handling system of the workcell. In some variations, the first portion 320 of the sterile liquid transfer system 300 may comprise a gantry 321 and an instrument head 322 operatively coupled thereto. The instrument head 322 may comprise a pneumatic actuator(s) 323, a peristaltic pump(s) 324, a sensor(s) 327, a sterile liquid transfer device cap actuator 326, a gripping feature 325, and the like. In some variations, the second portion 310 of the sterile liquid transfer system 300 may comprise a docking station 312 including a platform 313 within the docking station, sensor(s) 311, and a load cell 319 configured to determine a weight of a cartridge placed on the platform 313.

In some variations, the gantry 321 may be a multi axis system capable of moving the instrument head 322 coupled thereto in the x-, y-, and z-axis directions. In the context of the fluid device and the cartridge of the present disclosure, the gantry 321 is capable of moving the fluid device in the x-axis and y-axis relative to an array of sterile liquid transfer ports of the cartridge to align a sterile liquid transfer port of the fluid device with a corresponding sterile liquid transfer port of the cartridge and, subsequently, moving the fluid device in the z-axis to connect the sterile liquid transfer port of the fluid device with the corresponding sterile liquid transfer port of the cartridge.

In some variations, the instrument head 322 is configured to, among other things, secure a fluid device, manipulate a cap of a sterile liquid transfer port of the fluid device, and control fluid transfer from between the fluid device and the cartridge via a pneumatic actuator(s) 323 and a fluid pump 324.

In some variations, the pneumatic actuator(s) 323 of the instrument head 322 may be a linear actuator and the linear actuator may be coupled to the fluid pump 324. The pneumatic actuator(s) 323 may be configured to translate in order to adjust a position of the fluid pump 324 relative to the fluid device. In some variations, when the fluid pump 324 is a peristaltic pump, translation of the pneumatic actuator(s) 323 may adjust a position of a central axis of a rotor of the peristaltic pump so that bearings thereof achieve a predetermined occlusion of a corresponding compressible fluidic tubing of the fluid device (such as the compressible fluidic tubing of FIG. 2F and FIG. 2G). In some variations, the pneumatic actuator(s) 323 may be configured to permit peristaltic pump operating pressures of at least about 2 bar, at least about 3 bar, at least about 4 bar, at least about 5 bar, at least about 6 bar, at least about 7 bar, at least about 8 bar, at least about 9 bar, and/or at least about 10 bar. That is, when the pneumatic actuator(s) 323 is translated and bearings of the peristaltic pump are engaged with the compressible fluidic tubing of the fluid device, rotation of the rotor can be maintained at pressures of at least 10 bar. Operating pressure can be determined based on data from a sensor disposed within the rotor and/or bearings of the fluid pump and configured to sense a pressure applied to the roto and/or bearings when the fluid pump 324 engages the fluid pump module of the fluid device.

In some variations, the fluid pump 324 may be a centrifugal pump or a positive-displacement pump. In some variations, the compressible fluidic tubing of the fluid device may be exposed to an external environment of the fluid device. In particular, the compressible fluidic tubing may be proximate an external surface so that the fluid pump 324 may interact with the compressible fluidic tubing to move fluid therein. For example, when the fluid pump 324 is a peristaltic pump, bearings of the peristaltic pump can be iteratively contacted against the compressible fluidic tubing within the track. Iterative contact between the bearings and the compressible fluidic tubing results in iterative, controllable compression of the compressible fluidic tubing. Based on a direction of movement of a rotor of the peristaltic pump, this iterative compression results in the transfer of fluid between the fluid device and the cartridge. This bidirectional movement of fluids allows for the possibility of flowing fluids out of the fluid device and into the cartridge, such as for culture medium replenishment, and also flowing fluids out of the cartridge and into the fluid device, such as for sample collection.

In some variations, the predetermined occlusion of the compressible fluidic tubing may be based on a dimension of the compressible fluidic tubing (e.g., a tubing diameter, a distance between bearings of the peristaltic pump and a track of the fluid device) or may be based on a pressure generated within the compressible fluidic tubing and applied to/sensed by the peristaltic pump. The occlusion of the compressible fluidic tubing, along with a rate of rotation/revolution of the rotor of the peristaltic pump, as will be described below, controls a rate of fluid transfer. In some variations, the predetermined occlusion can be achieved during a fluid transfer operation using a feedback loop and based on information (e.g., linear translation, pressure) provided by or sensed by the pneumatic actuator(s) 323 and the peristaltic pump. For example, when linear translation is used to determine the predetermined occlusion, initially, a relative position of the track, a size of the compressible fluidic tubing within the track, and a relative position of the rotor/bearings of the peristaltic pump can be known. The predetermined occlusion may be a distance between the track and the rotor/bearings of the peristaltic pump, a dimension of the size of the compressible fluidic tubing within the track, or a linear translation distance of the rotor/bearings. As the pneumatic actuator(s) 323 is actuated, a distance between the rotor/bearings and the track can decrease until it is determined that the predetermined occlusion (e.g., a distance between the rotor/bearings and the track) is achieved. In another example, when pressure is used to determine the predetermined occlusion, initially, a pressure applied to the peristaltic pump and pneumatic actuator can be known. The predetermined occlusion may be a pressure calculated based on particular dimensions and characteristics of the compressible fluidic tubing and based on a desired fluid transfer rate. For instance, the pressure for the predetermined occlusion may be about 2 bar.

In some variations, controlling the occlusion of the compressible fluidic tubing is one component of controlling a rate of fluid flow into or out of the fluid device. Another component, when the fluid pump 324 is a peristaltic pump, is a rate of rotation/revolution of the rotor. Together, a rate of fluid flow into or out of the fluid device can be controlled such that controlled volumes of fluid are dispensed and/or obtained.

In some variations, the sensor(s) 327 of the instrument head 322 may comprise optical sensors, electromechanical sensors, proximity sensors, pressure sensors, capacitive sensors, accelerometers, gyroscopes, temperature sensors, and the like. For example, the sensor(s) 327 may include electromechanical sensors and/or optical sensors (e.g., photo sensors) configured as limit switches to determine a position and/or proximity of a fluid device relative to the instrument head 322. The electromechanical sensors can be used to confirm a position of the fluid device within the instrument head 322. In another example, the sensor(s) 327 may include optical sensors for determining a presence or absence of fluid, a distance between a sterile liquid transfer port of the fluid device and a corresponding sterile liquid transfer port of the cartridge, and the like.

In some variations, the sensor(s) 317 of the instrument head 322 may comprise electromechanical sensors and/or optical sensors configured to determine and/or confirm a position of the fluid device within the instrument head 322. For example, when the fluid device is initially loaded into the instrument head 322, a position of the fluid device can be confirmed prior to engagement by the gripping feature 325, the sterile liquid transfer device cap actuator 326, the fluid pump 324, and the like.

In some variations, the sensor(s) 317 of the instrument head 322 may comprise at least one optical sensor configured to evaluate fluid movement within fluid conduits of the fluid device and, thus, between the fluid device and the cartridge. In some variations, the evaluation may be an optical evaluation of the fluid movement within the fluid conduits via at least one viewing window of the fluid device that provides a vantage to at least a segment of the fluid conduits of the fluid device. For example, the at least one optical sensor may be aligned with the at least one viewing window and may detect a transition from air to liquid within the fluid conduits, thereby indicating the beginning of metered fluid transfer, or may detect a transition from liquid to air within the fluid conduits, thereby indicating an emptying of the fluid device. In some variations, the detection of the liquid to air, and vice versa, may also be used for determining a fluid flow rate estimation.

In some variations, the instrument head 322 may comprise at least one optical sensor configured to determine a distance between a sterile liquid transfer port of the fluid device and a corresponding sterile liquid transfer port of the cartridge. For example, the at least one optical sensor may be used as part of an alignment method to detect aspects of the corresponding sterile liquid transfer port and ensure precision in the connection between the sterile liquid transfer port of the fluid device and the corresponding sterile liquid transfer port of the cartridge. The at least one optical sensor may utilize any light from the electromagnetic spectrum and/or image sensors (e.g., cameras) to provide data related to the alignment method.

In some variations, the sterile liquid transfer device cap actuator 326 of the instrument head 322 may comprise an end effector configured to manipulate a cap of the sterile liquid transfer port of the fluid device after the sterile liquid transfer port of the fluid device is in aligned contact with a corresponding sterile liquid transfer port of the cartridge. For example, after aligned contact, the sterile liquid transfer ports are temporarily coupled via alignment features thereon. The sterile liquid transfer device cap actuator 326 can manipulate the caps of the sterile liquid transfer ports together to enable further processing and fluid transfer. Corresponding features on the cap of the sterile liquid transfer port of the fluid device and/or the corresponding sterile liquid transfer port of the cartridge can be engaged by the sterile liquid transfer device cap actuator 326 to slide each cap and permit sterilization of the connected sterile liquid transfer ports and, ultimately, fluid transfer therethrough. In some variations, the sterile liquid transfer device cap actuator 326 comprises a linear actuator configured to slide the end effector to actuate the caps of the connected sterile liquid transfer ports.

In some variations, the gripping feature 325 of the instrument head 322 comprises an end effector configured to grip the fluid device (e.g., via a shaft of the sterile liquid transfer port of the fluid device). The end effector may comprise two parallel jaws configured to open and close in order to grip the fluid device. In some variations, the end effector is configured to grip the fluid device after the sensor(s) 317 of the instrument head confirms the positioning of the fluid device within the instrument head.

In some variations, the platform 313 of the docking station 312 comprises a planar surface with recesses, apertures, and the like for engagement with a cartridge. For example, the platform 313 may comprise a cartridge loading bracket configured to receive the cartridge. In some variations, the platform 313 may be outfitted with sensor(s) 311 configured to determine a presence of the cartridge within the cartridge loading bracket. In some variations, the platform 313 may be outfitted with a load cell(s) 319. Instead of or in addition to relying on sensor(s) 327 of the instrument head 322 to determine fluid flow rate (e.g., volumetric flow rate) into and out of the fluid device and the cartridge, the load cell(s) 319 can be used to determine a mass of fluid transferred into or out of the cartridge and, thus, control of fluid transfer via the fluid pump 324 can be based on the mass of transferred fluid.

In some variations, the platform 313 may be a floating platform and may be engageable by actuators within the docking station 312 to lift the floating platform toward the first portion 320 of the sterile liquid transfer system 300. The floating platform allows a cartridge positioned thereon to be secured within the docking station 312 and engageable by an instrument head of the first portion 320 of the sterile liquid transfer system 300. Securing the cartridge within the docking station 312 may be confirmed by a sensor(s) 311, which determines whether the cartridge is "clamped" within the docking station 312. In some variations, clamping may be confirmed by contact between a top surface of the cartridge and a clamping surface of the docking station 312. For example, actuators, which may be disposed toward a base wall of the docking station 312, can lift the floating platform, and the cartridge thereon, toward a clamping surface of a top wall of the docking station 312. Contact between the cartridge and the clamping surface can be confirmed by e.g., sensor(s) 311.

In some variations, the platform 313 may be outfitted with connectors, ports, tubing, and the like that permits interfacing with the plurality of modules of the cartridge. For instance, the platform 313 may include impellers, impeller actuators, magnets, rotors, heating elements, gas lines, gas ports, and the like in order to maintain bioreactor like conditions of cellular products inside the cartridge while the cartridge is within the docking station 312.

Figure 3B:
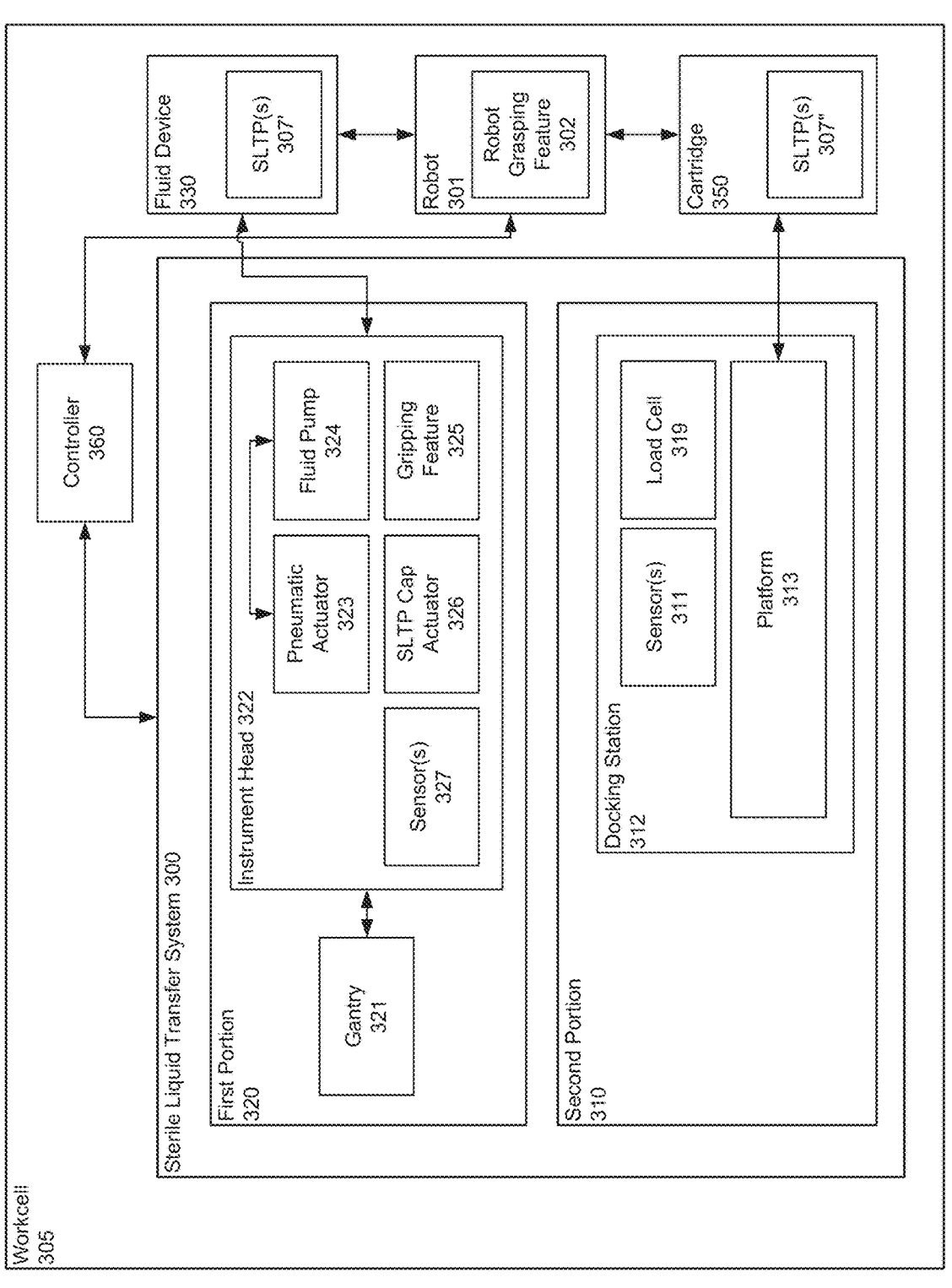
FIG. 3B is a schematic diagram of an illustrative system for automated fluid transfer by a sterile liquid transfer system within a cell process system.

Turning now to FIG. 3B, a schematic diagram of an illustrative system for automated fluid transfer, including a fluid device, a cartridge, and a workcell, is provided.

In some variations, the sterile liquid transfer system 300 may be an instrument within a workcell 305, such as the workcell of FIG. 2A through FIG. 2E. The sterile liquid transfer system 300 may be configured to receive, at a first portion 320 of the sterile liquid transfer system 300, a fluid device 330. The fluid device 330 may be provided to an instrument head 322 of the first portion 320 of the sterile liquid transfer system 300 by a robot(s) 301 of a material handling system of the workcell 305. The robot(s) 301 may comprise a robot grasping feature 302 configured to engage robot engagement feature(s) of the fluid device 330 (see FIG. 2F and FIG. 2G). The sterile liquid transfer system 300 may be configured to receive, at a second portion 310 of the sterile liquid transfer system 300, a cartridge 350. The cartridge 350 may be provided to a platform 313 of a docking station 312 of the second portion 310 of the sterile liquid transfer system 300 by the robot(s) 301 of the material handling system of the workcell 305. In some variations, the material handling system of the workcell 305 may comprise a single robot 301 configured to manipulate and move each of the fluid device 330 and the cartridge 350. In some variations, the material handling system of the workcell 305 comprises at least two robots 301, each configured to move one of the fluid device 330 and the cartridge 350. For example, a first robot may be configured with a first end effector to move fluid devices between the first portion 320 of the sterile liquid transfer system 300 and the reagent vault system and a second robot may be configured with a second end effector to move cartridges between instruments of the workcell 305 and second portion 310 of the sterile liquid transfer system 300.

In some variations, the fluid device 330 may comprise at least one sterile liquid transfer port 307'. In some variations, the cartridge 350 may comprise at least one sterile liquid transfer port 307". In some variations, the cartridge 350 may comprise a plurality of sterile liquid transfer ports" arranged in an array and each fluidically coupled to a reservoir, module, or the like within the cartridge 350.

In some variations, the workcell 305 may comprise therein at least one sterile liquid transfer system 300, a robot(s) 301, at least one fluid device 330, at least one cartridge 350, and a controller 360. It should be appreciated that the at least one sterile liquid transfer system 300, the at least one fluid device 300, and the at least one cartridge 350 are configured to be portable, disposable, and/or otherwise not be a permanent component of the workcell 305.

In some variations, and as noted above, the fluid device 330 may be moved or otherwise manipulated by the robot(s) 301 of the workcell 305 under the control of the controller 360. In some variations, the controller 360 sends signals to the robot(s) 301 to move and/or manipulate the fluid device 330 via the one or more robot engagement features of the fluid device 330. Movement and manipulation can include moving the fluid device 330 within the workcell 305, such as between the reagent vault system of the workcell 305 and the sterile liquid transfer system 300 of the workcell 305, and/or controlling an orientation of the fluid device 330.

In some variations, as noted above, the cartridge 350 may be moved or otherwise manipulated by the robot(s) 301 of the workcell 305 under the control of the controller 360. In some variations, the controller 360 sends signals to the robot(s) 301 to move and/or manipulate the cartridge 350. Movement and manipulation of the cartridge 350 can include moving the cartridge 350 between instruments within the workcell 305, such as between a bioreactor instrument, an electroporation instrument, a counterflow centrifugal elutriation instrument, and/or the like, and the sterile liquid transfer system 300.

In some variations, the sterile liquid transfer system 300 can be operatively connected to the controller 360 such that data from the gantry 321 and the instrument head 322 of the first portion 320 can be provided to the controller 360 and such that the instrument head 322, and components thereof, can be controlled during a method of automated fluid transfer. In some variations, the controller 360 may receive data from the instrument head 312 that may include data corresponding to activity of the fluid pump 324, data from sensor(s) 327 corresponding to fluid flow within fluid conduits of the fluid device 330, the sterile liquid transfer port cap actuator 326, sterilization process ports of the fluid device 330, and/or at least one air process port of the fluid device 330. Data received by the controller 360 from the fluid pump 324 may include rotations/revolutions per minute, a direction of rotation, fault detection data, and the like. Data received by the controller 360 from the pneumatic actuator 323 may include positional data related to a rotor of the fluid pump 324. Such data can be used in conjunction with known characteristics such as a length and a diameter of the compressible fluidic tubing of the fluid pump 324, and with data from the sensor(s) 327 corresponding to fluid flow (e.g., liquid to air transition) within the fluid device 330, as alluded to earlier, to determine or estimate a flow rate into and/or out of the fluid device 330. This data may include properties (e.g., viscosity) of the fluid to be transferred. To this end, data received by the controller 360 from the sensor(s) 327 may include optical data obtained such as absorbance, reflectance, and/or fluorescence data of a fluid within fluid conduits of the fluid device 330. In some variations, the data received by the controller 360 from the sensor(s) 327 includes electromechanical data related to limit switches indicated a position of the fluid device 330 and or the cartridge 350, and the like. In some variations, the controller 360 may receive data from the gantry 321, including positional data of the instrument head 312 and a fluid device 330 hereon.

In some variations, data from each of the components of the workcell 305 described above can be integrated to perform automated fluid transfer. For example, the controller 360 may generate and/or send a signal to the robot(s) 301 to move, invert, and/or couple the fluid device 330 with the instrument head 322 of the sterile liquid transfer system 300 via the one or more robot engagement features of the fluid device 330.

In some variations, the controller 360 may generate signals to the pneumatic actuator 323 and the fluid pump 324 to control a position of the fluid pump 324 and to control fluid transfer between the fluid device 330 and the cartridge 350. In some variations, a rotational velocity and a direction of rotation of a rotor of a peristaltic pump of the fluid pump 324 can be controlled in order to control bidirectional flow and flow rate of a fluid. In some variations, a predetermined occlusion of a compressible fluidic tubing of a fluid pump module of the fluid device 330 can be obtained by sending signals, from the controller 360, to the pneumatic actuator 323 to control movement of the pneumatic actuator 323 and the fluid pump 324 coupled thereto based on a linear translation of the pneumatic actuator 323 and/or based on a pressure sensed at the fluid pump 324.

In some variations, the controller 360 generates and/or sends further signals to the gantry 321 and to the sterile liquid transfer port cap actuator 326 to manipulate a sterile liquid transfer port 307 of the fluid device 330 and a corresponding sterile liquid transfer port 307 of the cartridge 350 to allow sterile, automated, and precisely metered (e.g., precise control of a transferred fluid volume) fluid transfer. For example, the signals to the gantry 321 may include x-, y-, and z-axis coordinates for positioning the instrument head 312. In another example, the signals to the sterile liquid transfer port cap actuator 326 may include signals to control a configuration of the at least one port and valve of the sterile liquid transfer ports 307. In some variations, and as it relates to opening a flow path between the sterile liquid transfer port 324 of the fluid device 300 and a sterile liquid transfer port of another fluid device, the controller 360 may first be configured to generate a signal to the gantry 321 and a port signal to the sterile liquid transfer port cap actuator 326 to adjust a z-height of the instrument head 322 and couple the at least one port of the fluid device 330 to a corresponding port of the sterile liquid transfer port 307 of the cartridge 350. Coupling the at least one port 307 of the fluid device 330 to the corresponding port may comprise transitioning the ports to at least a partially open position. Next, the controller 360 may generate a valve signal to the gantry 321 to translate the instrument head 322 relative to the cartridge 350 to bring a valve of the sterile liquid transfer port 307' of the fluid device 330 into contact with a corresponding valve of the sterile liquid transfer port 307" of the cartridge 350. This can include adjusting a z-height of the instrument head to push the valves into a coupling arrangement. To finally open the fluid pathway, the controller 360 may then generate another valve signal to transition the valve and the corresponding valve to the open configuration. For example, the valves may operate on a push to connect principle. After fluid transfer, similar controlling signals can be generated to transition the sterile liquid transfer port 307 of the fluid device 330 and the corresponding sterile liquid transfer port 307 of the cartridge 350 to a closed configuration.

Turning now to FIG. 4A through FIG. 4D, renderings of views of an illustrative sterile liquid transfer system for automated fluid transfer are provided. Like reference numerals will be used with reference to FIG. 4A through FIG. 4D, though, not all features will be called out in each figure.

Figures 4A, 4B:
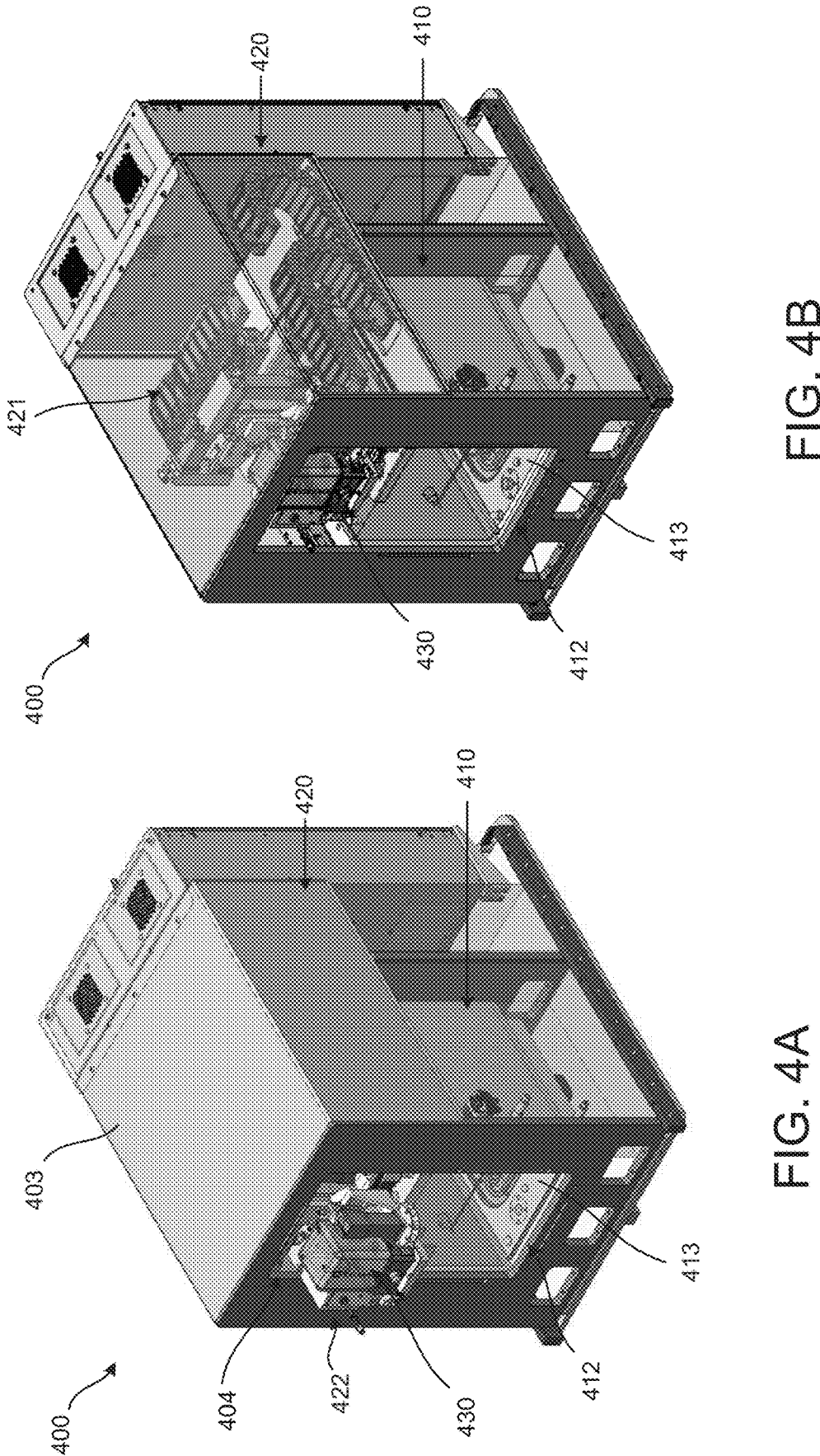
FIG. 4A is a rendering of an illustrative variation of a sterile liquid transfer system.
FIG. 4B is a transparent rendering of an illustrative variation of a sterile liquid transfer system.
Figures 4C, 4D:
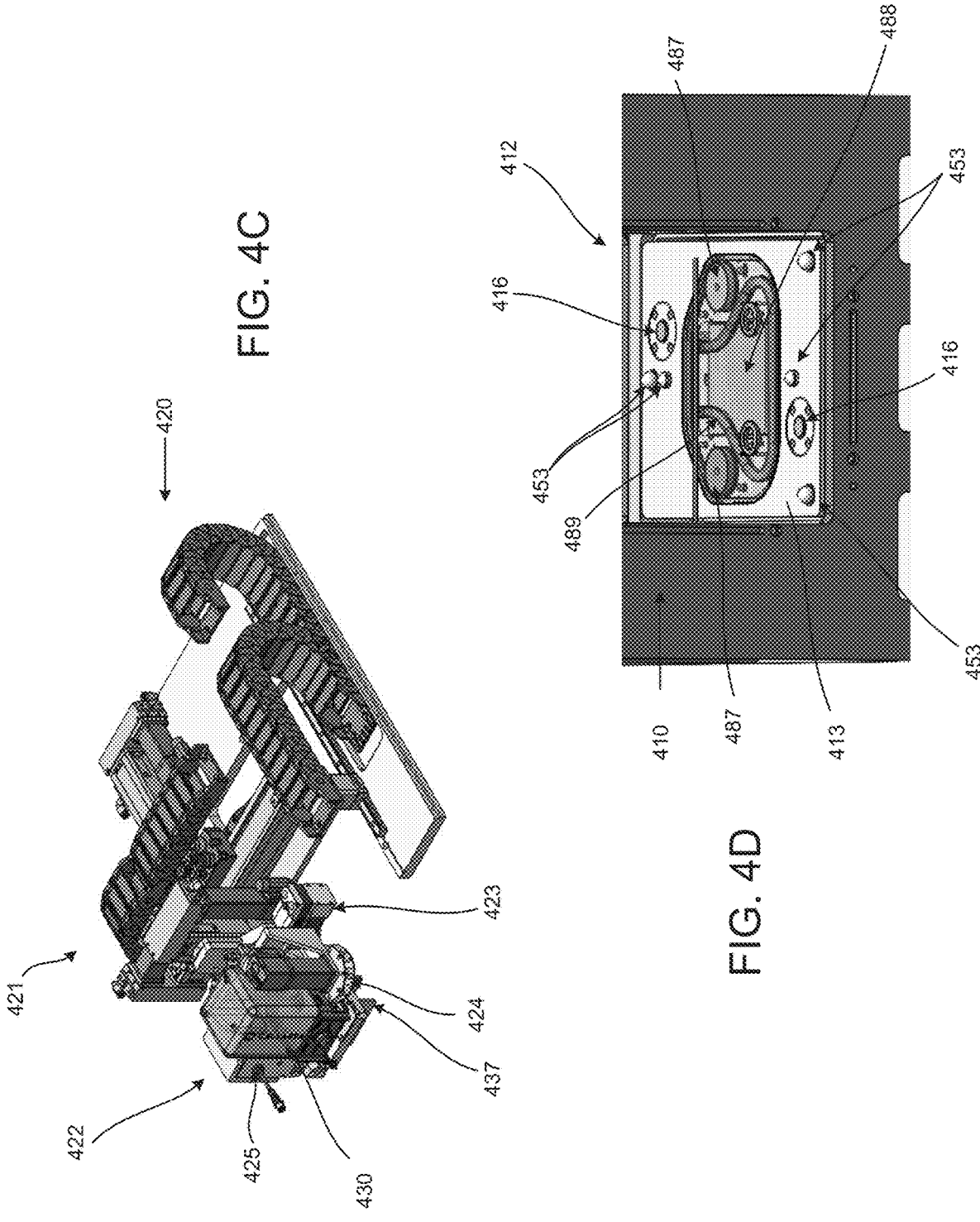
FIG. 4C is a rendering of an illustrative variation of a first portion of a sterile liquid transfer system.
FIG. 4D is a rendering of an illustrative variation of a second portion of a sterile liquid transfer system.

In some variations, the sterile liquid transfer system 400 comprises a housing 403 and a first portion 420 and a second portion 410 therein. As shown in FIG. 4A, the first portion 420 comprises an instrument head 422 configured to receive a fluid device 430 via a window 404. The instrument head 422 may be coupled to and positionable by a gantry 421 within the first portion 420, as shown in FIG. 4B. The second portion 410 of the sterile liquid transfer system 400 comprises a docking station 412 and a platform 413 therein. The first portion 420 of the sterile liquid transfer system 400 is detailed further with reference to FIG. 4C. As shown in FIG. 4C, the gantry 421 may be coupled to the instrument head 422 and configured to position the instrument head 422 and a fluid device 430 coupled thereon. The instrument head 422 may comprise a fluid pump 424, a pneumatic actuator 423, a sterile liquid transfer device cap actuator end effector 437, and a gripping feature 425. As shown in FIG. 4C, the gantry 421 includes linear actuators configured to permit the instrument head 422 to be moved in the x-, y-, and z-axis directions relative to a cartridge within the second portion 410 of the sterile liquid transfer system 400. As shown in FIG. 4D, the second portion 410 comprises the docking station 412 and the platform 413. The platform 413 may be a floating platform configured to be lifted to engage a cartridge with a clamping surface of the docking station 412 and to secure the cartridge in position for engagement with the instrument head 422. In some variations, the platform 413 may include cartridge alignment pins 453, which provide an initial registration of the cartridge with the platform 413, motor(s) 487, which provide stirring functionality to one or more modules of the cartridge, a heating element 488 and a cooling element 489, which provide temperature control to fluids and cells within the one or more modules of the cartridge, and lifting guides 416, which engage and support the platform 413 while the floating platform is being lifted to engage the cartridge with the clamping surface of the docking station 412. In some variations, the lifting guides 416 may be guide rods that engage corresponding apertures of the floating platform to provide additional rigidity to and prevent deflection of the floating platform during lifting.

Turning now to FIG. 5A through FIG. 5F, renderings of views of an illustrative sterile liquid transfer system for automated fluid transfer are provided. Like reference numerals will be used with reference to FIG. 5A through FIG. 5F, though, not all features will be called out in each figure.

Figure 5B:
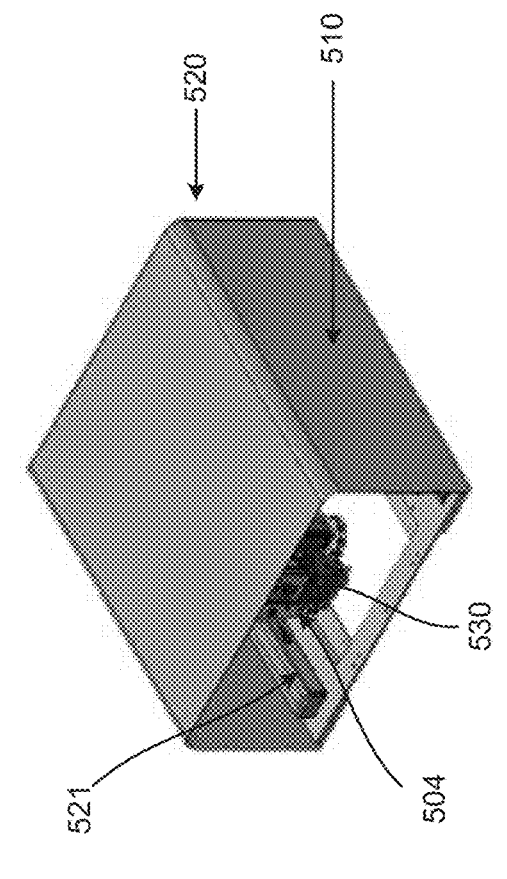
FIG. 5B is a rendering of an illustrative variation of a first portion of a sterile liquid transfer system.
Figure 5A:
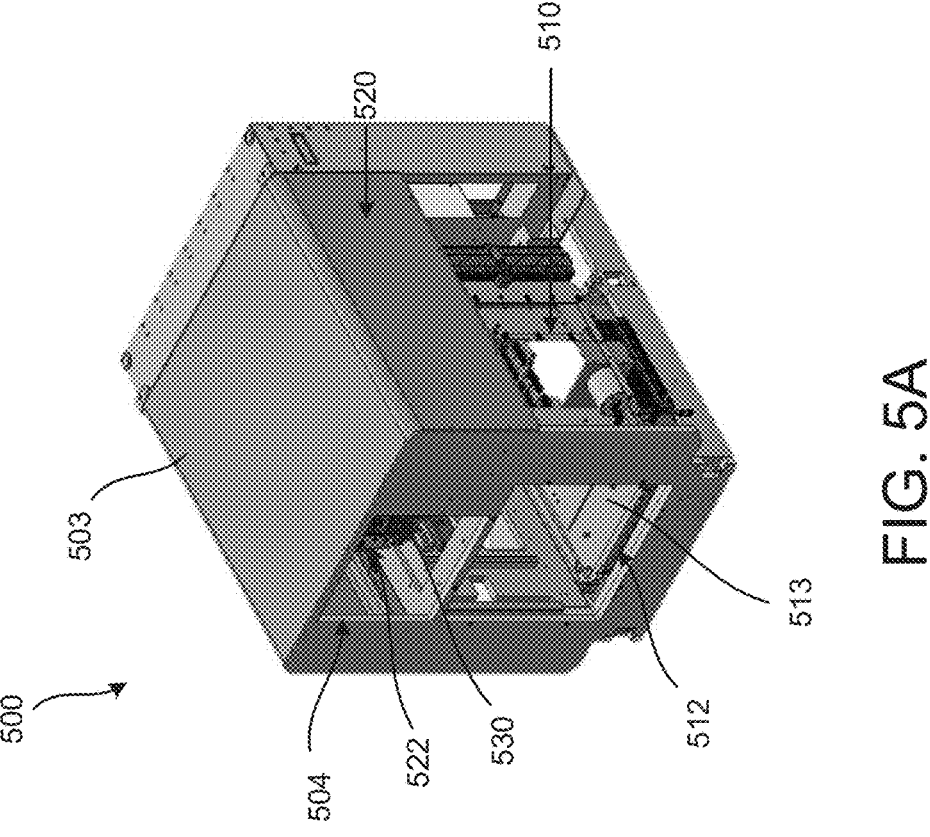
FIG. 5A is a rendering of an illustrative variation of a sterile liquid transfer system.

In some variations, the sterile liquid transfer system 500 comprises a housing 503 and a first portion 520 and a second portion 510 therein. As shown in FIG. 5A, the first portion 520 comprises an instrument head 522 configured to receive a fluid device 530. The instrument head 522 may be coupled to and positionable by a gantry 521 within the first portion 520, as shown in FIG. 5B. Though not shown in detail with reference to FIG. 5A through FIG. 5F, the instrument head 522 is substantially similar to the instrument head described in detail previously and with reference to the instrument head 422 of FIG. 4A through FIG. 4D. As shown in FIG. 5C through FIG. 5F, the second portion 510 of the sterile liquid transfer system 500 comprises a docking station 512 and a platform 513 therein. The platform 513 comprises a recess 514 configured to receive a cartridge. In some variations, the platform 513 may be a floating platform 517 configured to be lifted by one or more actuators 515, with support by one or more lifting guides 516 which engage and support the floating platform 517 during movement, to bring the cartridge into contact with and secure the cartridge against a clamping surface of the docking station 512. In some variations, the one or more lifting guides 516 may be guide rods that engage corresponding apertures of the floating platform 517 to provide additional rigidity to and prevent deflection of the floating platform 517 during lifting. The floating platform 517 may comprise at least one interface 518. The at least one interface 518 may provide temperature control, gas control, and the like to cellular products within a cartridge. In some variations, the at least one interface 518 may also include an actuator for generating flow within a bioreactor module of the cartridge. In some variations, the at least one interface 518 may comprise a bioreactor module engagement feature. The bioreactor module engagement feature may comprise, for example, an impeller actuator that provides a stirring functionality in a bioreactor module of the cartridge to allow mixing of the cellular product prior to sampling via fluid transfer.

Figure 5F:
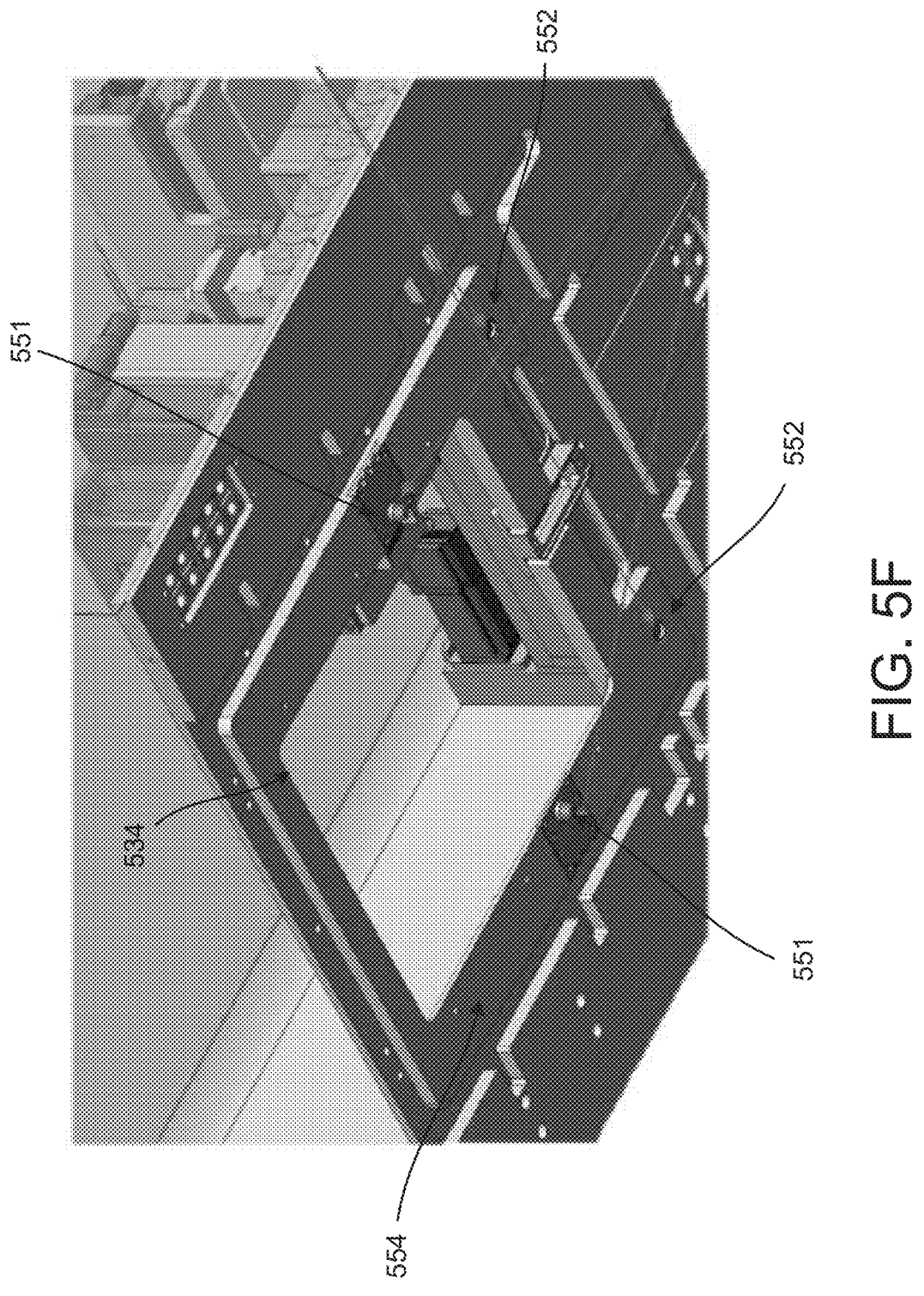
FIG. 5F is a rendering of an illustrative variation of an aspect of a second portion of a sterile liquid transfer system.

In some variations, the clamping surface of the docking station may be the clamping surface 554 shown in FIG. 5F. When the floating platform lifts the cartridge toward the clamping surface 554, corresponding features of the cartridge may engage clamping surface alignment pins 551 on the clamping surface 554 of the docking station, which help to align the cartridge relative to access window 534. This alignment acts as a registration step by which a location of sterile liquid access ports on the cartridge relative to the instrument head is known. Successful clamping between the cartridge and the clamping surface 554 can be confirmed by at least one sensor 552 configured to determine when the cartridge is secured within the docking station.

Turning now to FIG. 6A through FIG. 7B, renderings of views of an illustrative instrument head are provided. Like reference numerals will be used with reference to FIG. 6A through FIG. 6D, though, not all features will be called out in each figure.

In some variations, an instrument head 622 comprises a pneumatic actuator 623 mounted to a bracket 629 and operatively coupled to a fluid pump 624. The instrument head 622 may further comprise a gripping feature 625 having a gripper feature end effector 632 configured to grip a fluid device 630 received within the instrument head 622. In some variations, the instrument head 622 further comprises an instrument head sensor 627, which may be a proximity sensor 635, configured to determine when the fluid device 630 is seated within the instrument head 622 and can be engaged by the gripping feature end effector 632 of the gripping feature 625. As shown in previous figures, the instrument head 622 may be mounted to a gantry of the first portion of the sterile liquid transfer system and moved thereby.

Figure 6B:
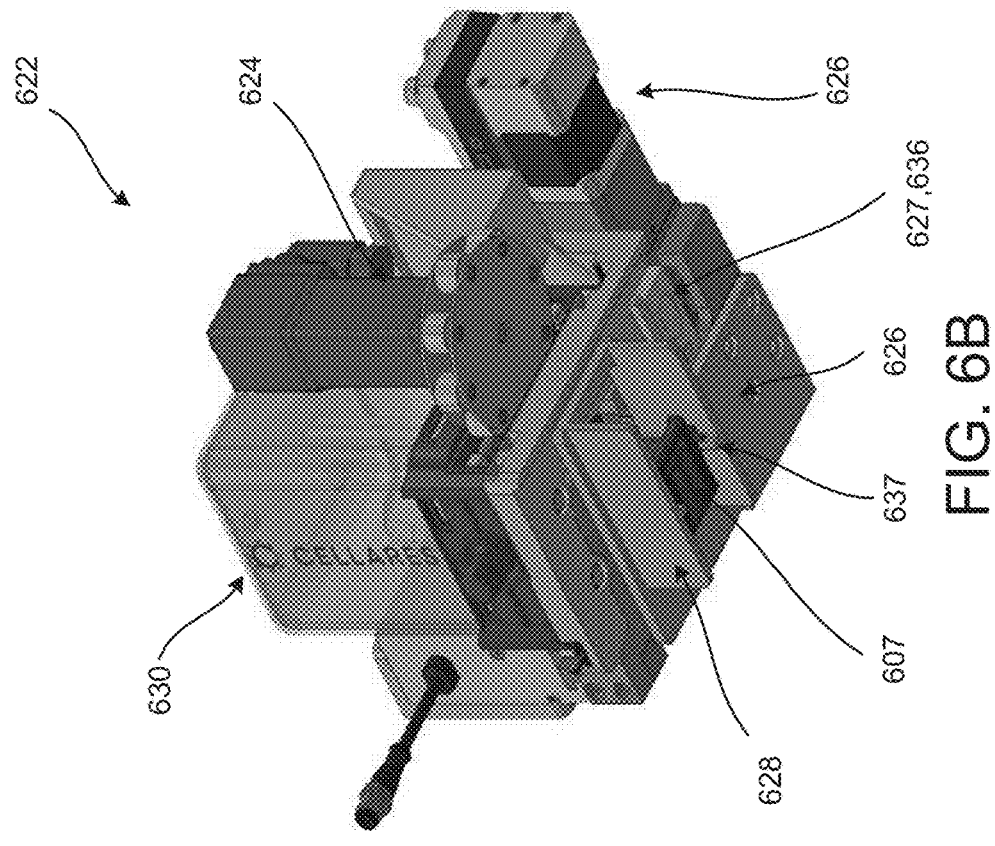
FIGS. 6A-6D are renderings of an illustrative variation of an instrument head of a first portion of a sterile liquid transfer system, the instrument head being coupled to a fluid device.
Figure 6A:
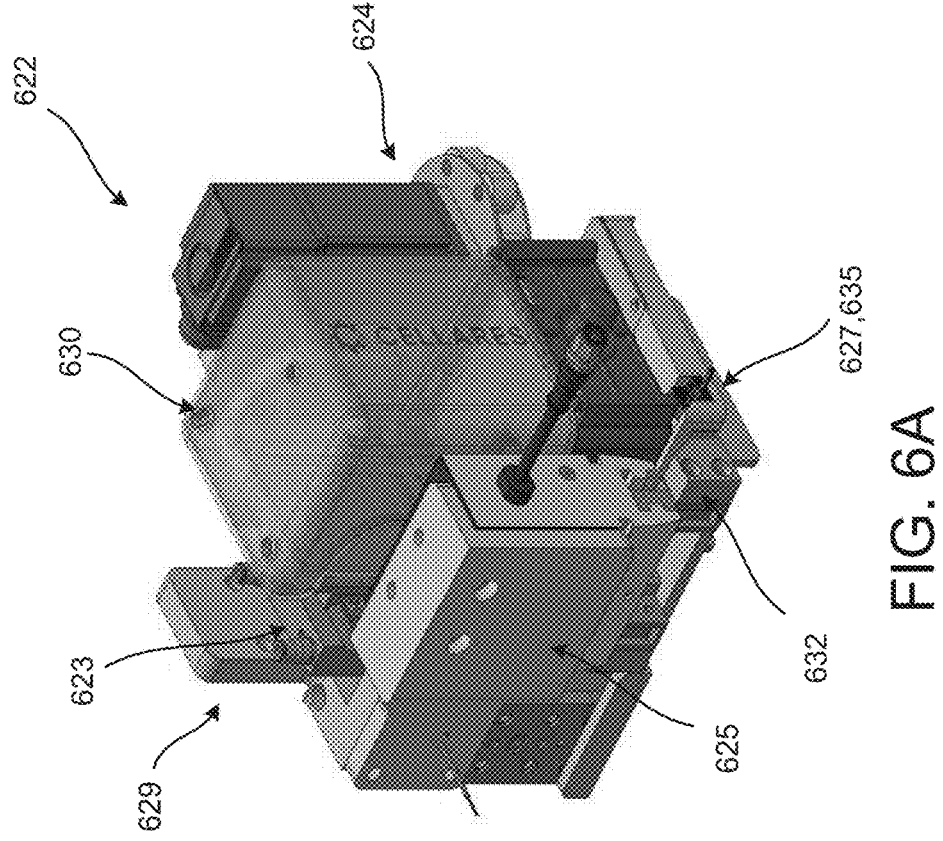

In some variations, and as shown in FIG. 6B, the instrument head 622 may comprise a sterile liquid transfer device (SLTD) cap actuator 626 having a SLTD cap actuator end effector 628. In some variations, the SLTD cap actuator end effector 628 may comprise a detent 637. The detent 637 may be configured to engage a corresponding feature or features (see 639 in FIG. 6D) of a cap of a sterile liquid transfer port 607 of the fluid device 630 such that, when the SLTD cap actuator end effector 628 slides, the cap of the sterile liquid transfer port 607 is moved via engagement with the detent 637. In some variations, the instrument head 622 may comprise an instrument head sensor 627, which may be a distance sensor 636. The distance sensor 636 may be used, as will be described with reference to the flow diagram of FIG. 8 and FIG. 13B, to perform aspects of alignment of the sterile liquid transfer port 607 of the fluid device 630 with a corresponding sterile liquid transfer port of the cartridge.

Figures 6C, 6D:
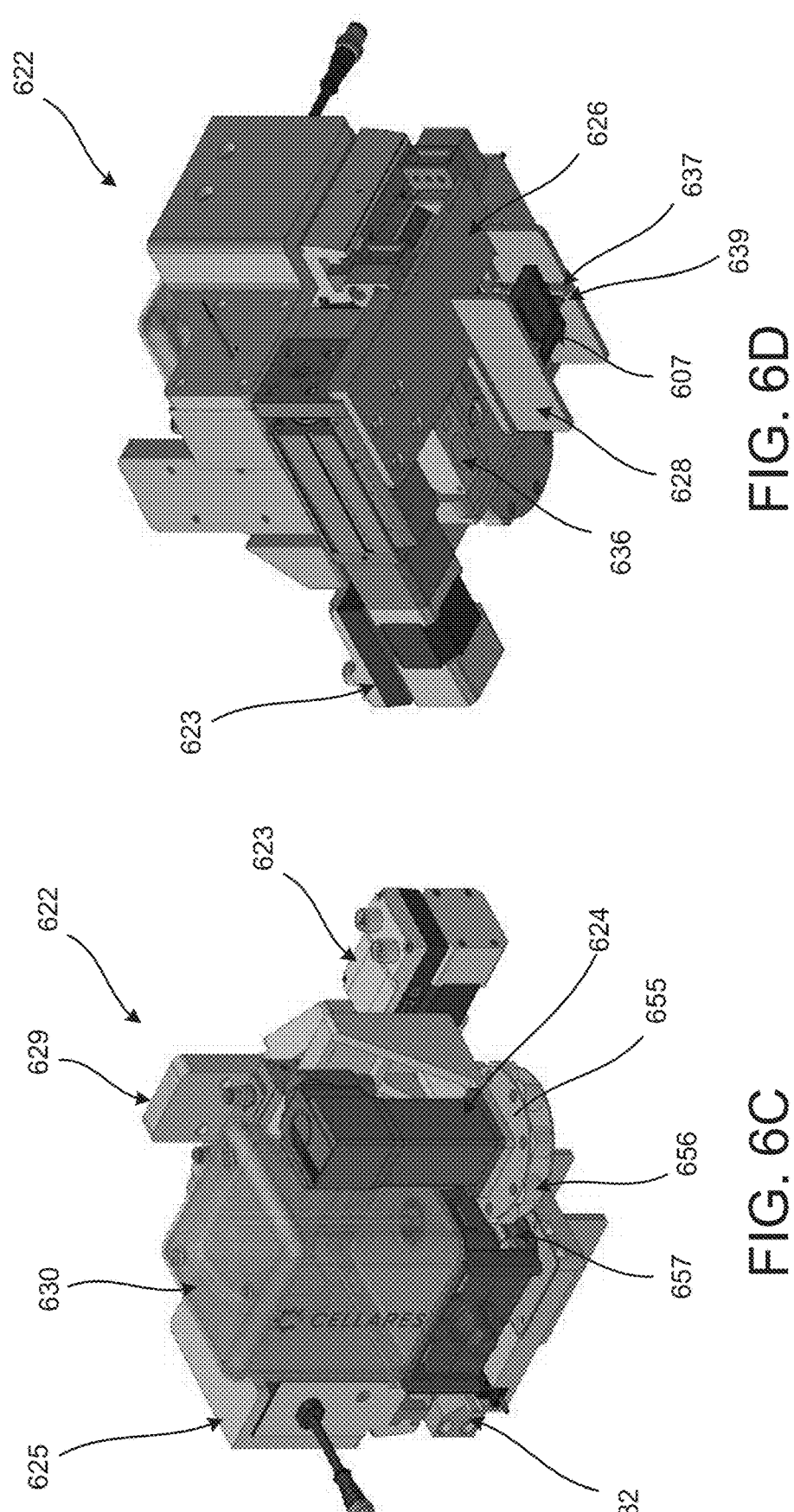

In some variations, and as shown in FIG. 6C, the fluid pump 624 of the instrument head 622 may comprise a peristaltic pump including a rotor 655 and bearings 656. The bearings 656 of the peristaltic pump may be configured to engage a compressible fluidic tubing 657 of the fluid device 630 during fluid transfer between the fluid device 630 and a cartridge. Such fluid transfer is described previously herein.

FIG. 6D provides an additional view of the instrument head 622 and, in particular, the distance sensor 636, the SLTD cap actuator end effector 628, the SLTD cap actuator 626, a detent engagement feature 639, and the detent 637.

Figure 7A:
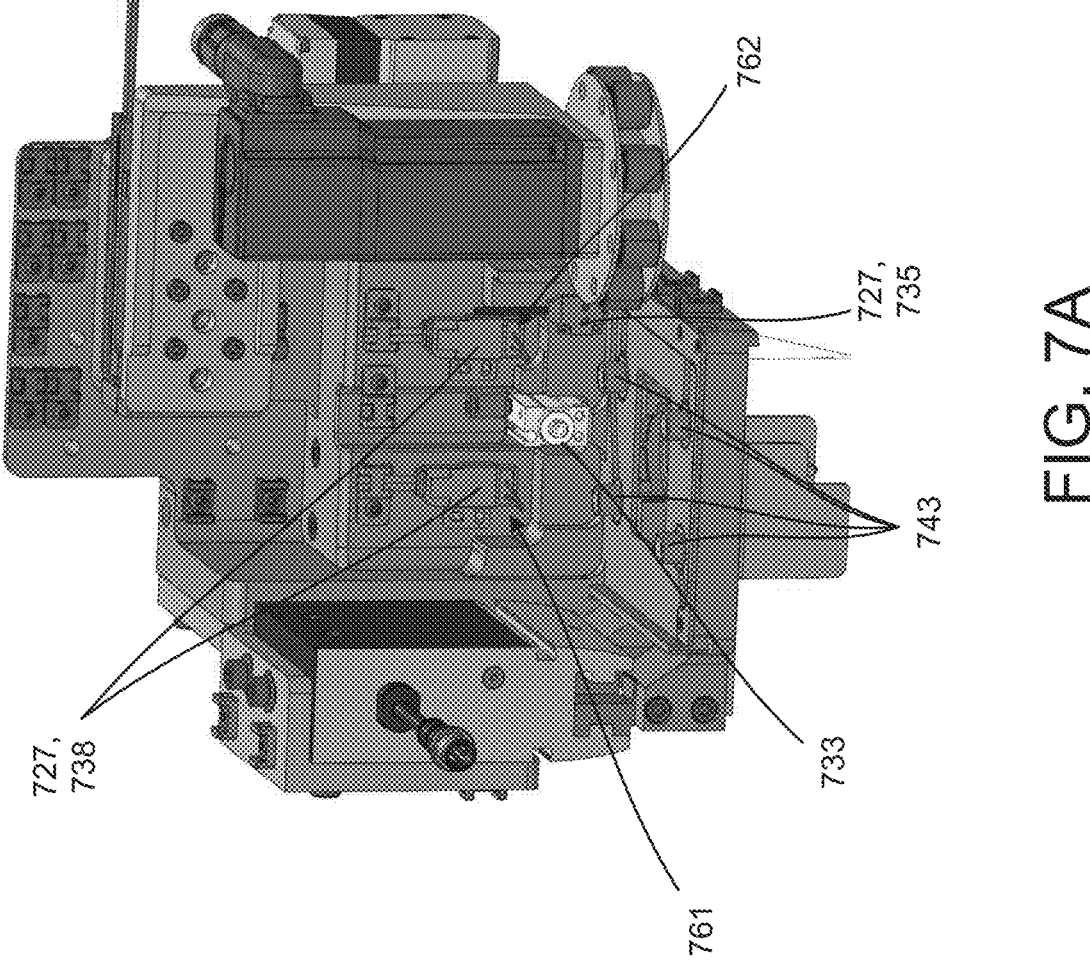
FIG. 7A and FIG. 7C are renderings of an illustrative variation of an instrument head of a first portion of a sterile liquid transfer system, the instrument head being decoupled from a fluid device.
Figure 7C:
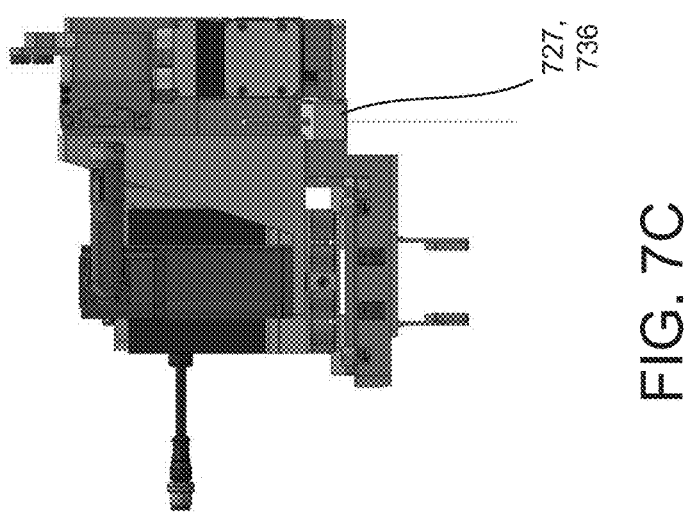

Turning now to FIG. 7A and FIG. 7C, renderings of views of an illustrative instrument head are provided. In FIG. 7A and FIG. 7C, instrument head 722 is displayed without a fluid device in order to view the sensors, actuators, and ports therein.

In some variations, the instrument head 722 may comprise sensor(s) 727, actuator 733, and sterilization port(s) 743. Each of the sensor(s) 727, actuator 733, and sterilization port(s) 743 may be configured to engage a fluid device. In an example, the sensor(s) 727, which may include optical sensors 738, can be used to determine the presence of liquid or air within fluid conduit of the fluid device, thereby aiding in the control of fluid transfer between the fluid device and a cartridge. The optical sensors 738 may have a vantage into the fluid device via e.g., one or more viewing windows of the fluid device. In another example, the sensor(s) 727, which may include proximity sensor 735, can be used to confirm the presence of the fluid device within the instrument head 722. In some variations, the sterilization port(s) 743 may be configured to provide sterilant (e.g., vaporized hydrogen peroxide) from a sterilant source within the workcell to the fluid conduits and the sterile liquid transfer port of the fluid device. In some variations, the actuator 733 can be configured to actuate pinch valves on the fluid device to prevent air from entering fluids within the fluid device during fluid transfer. In some variations, the sensor(s) 727 is a distance sensor 736. The distance sensor 736 may be used, as will be described with reference to the flow diagram of FIG. 8, to perform aspects of alignment of the sterile liquid transfer port of a fluid device with a corresponding sterile liquid transfer port of a cartridge.

II. Automated Fluid Transfer Methods

Described herein are also methods for fluid transfer, for example, automated fluid transfer within a cell processing system.

Initially, a framework for automated fluid transfer within a sterile liquid transfer system will be described with reference to method 800 of FIG. 8. Method 800 will be described with reference also to FIG. 9A through FIG. 14B. Reference to steps and subprocesses of method 800 will be made clearer in view of each of FIG. 9A through FIG. 14B. It should be appreciated that method 800 can be performed according to instructions executed by a controller operatively connected to each component within the workcell, including the sterile liquid transfer system, the cartridge, the fluid device, and the robots. The controller may be similar to controller 120 and/or controller 360, each described previously herein.

Figure 9B:
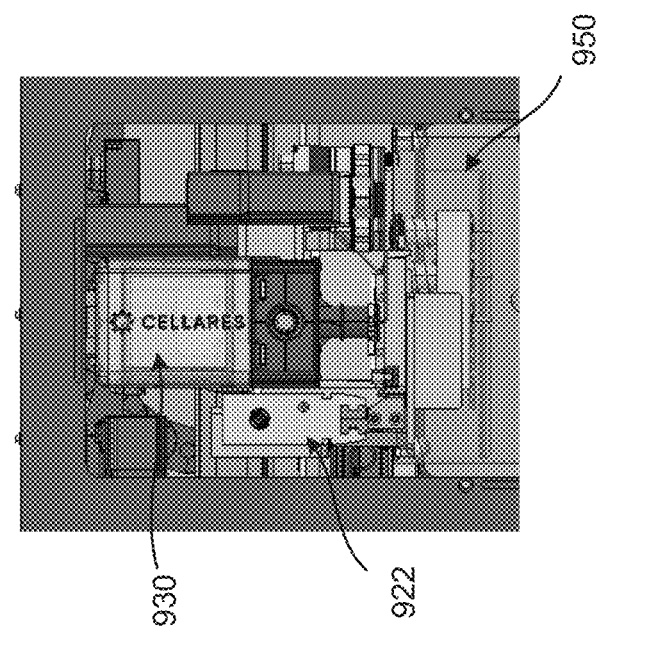
FIG. 9B is a rendering of a front view of an illustrative variation of a sterile liquid transfer system during a step of an illustrative method for automated fluid transfer.
Figure 9A:
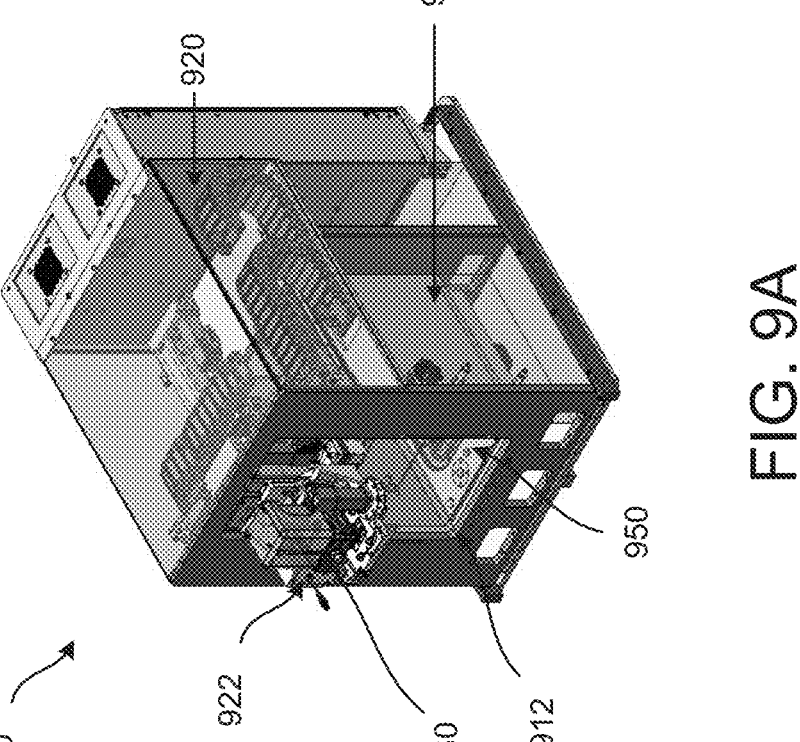
FIG. 9A is a rendering of a perspective view of an illustrative variation of a sterile liquid transfer system during a step of an illustrative method for automated fluid transfer.

Method 800 initially comprises, at step 802, transferring a fluid device and a cartridge to the sterile liquid transfer system. The fluid device can be transferred by a robot of a material handling system of a workcell from a reagent vault system of the workcell to a first portion of the sterile liquid transfer system. The cartridge can be transferred by the same robot or a different robot of the material handling system of the workcell from an instrument of the workcell, such as a bioreactor instrument, an electroporation instrument, and the like, to a second portion of the sterile liquid transfer device. As shown in FIG. 9A and FIG. 9B, the fluid device 930 can be loaded into an instrument head 922 of the first section 920 of the sterile liquid transfer system 900 (at a pick-up/drop off or loading/unloading location) and the cartridge 950 can be loaded into a docking station 912 of the second portion 910 of the sterile liquid transfer system 900. In some variations, the fluid device 930 is inverted prior to loading into the instrument head 922 of the first portion 920 of the sterile liquid transfer system 900.

In some variations, and as shown in FIG. 10A through FIG. 10F, which are illustrative variations of a robot end effector of the material handling system of the workcell, the fluid device can be lifted, rotated, inverted, and the like by the robot of the material handling system to prepare the fluid device for loading into the sterile liquid transfer system.

In some variations, one or more robot engagement features 1031 of the fluid device 1030 may be engageable by a robot of a workcell to move and otherwise manipulate the fluid device 1030. This allows for automated pick and place of the fluid device 1030 within the workcell. In some variations, the one or more robot engagement features 1031 may be at least one depression and/or protrusion within or on a surface of the fluid device 1030. In some variations, the one or more robot engagement features 1031 of the fluid device 1030 may also be configured or configurable to permit different storage orientations with a reagent vault system of the workcell. For instance, the one or more robot engagement features 1031 of the fluid device 1030 may be configured to allow for hanging the fluid device 1030 in e.g., an inverted orientation with the reagent vault system.

Figure 10A:
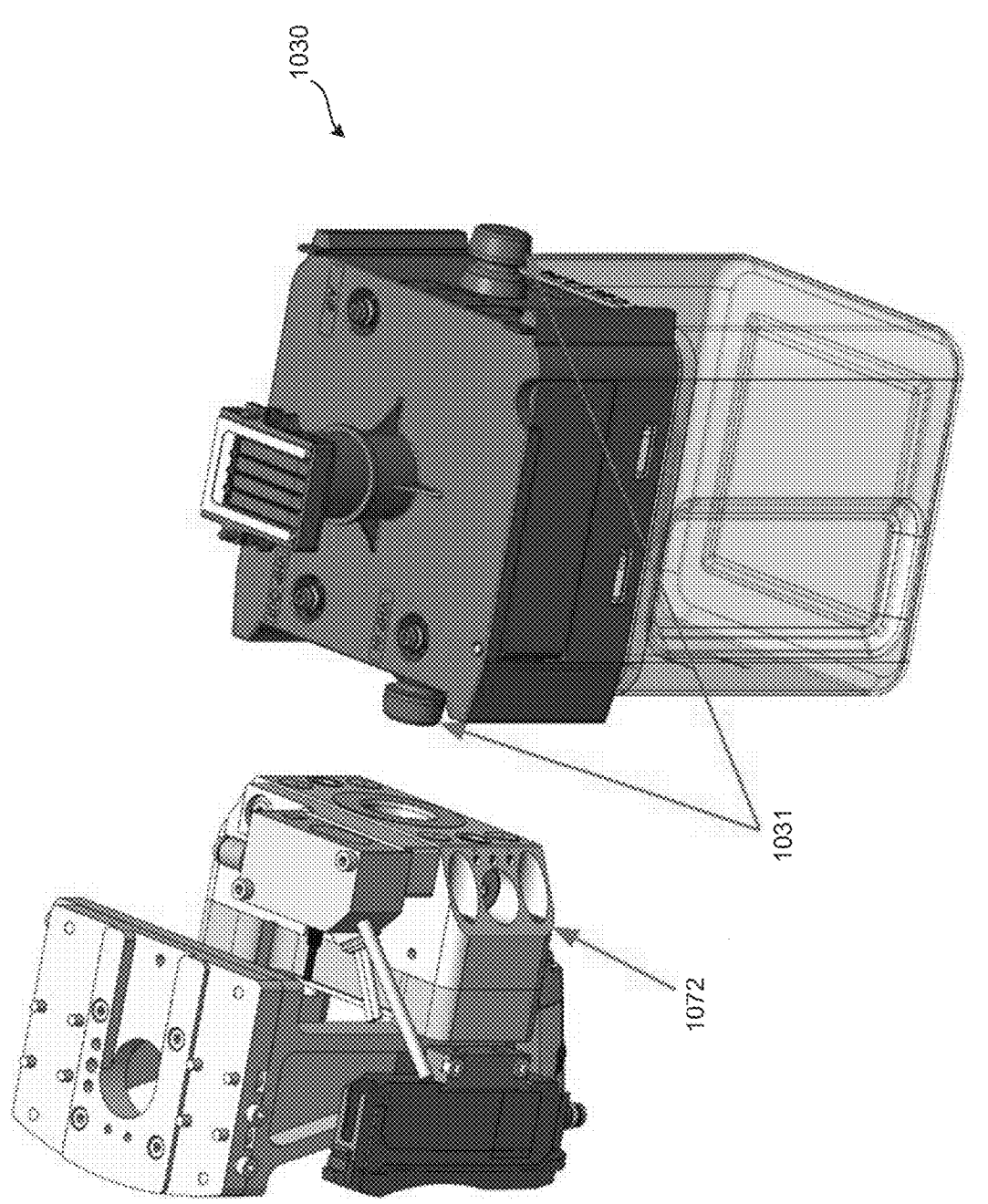
FIG. 10A is a rendering of an illustrative variation of a robot grasping feature of a material handling system of a workcell and robot engagement features of a fluid device.
Figure 10C:
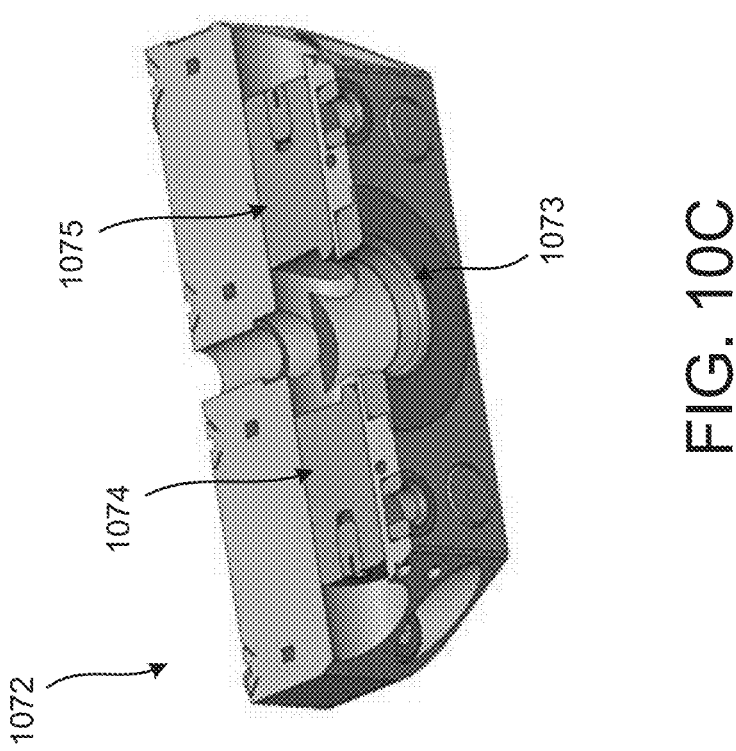
FIG. 10B and FIG. 10C are renderings of an illustrative variation of a robot grasping feature of a material handling system of a workcell.
Figure 10B:
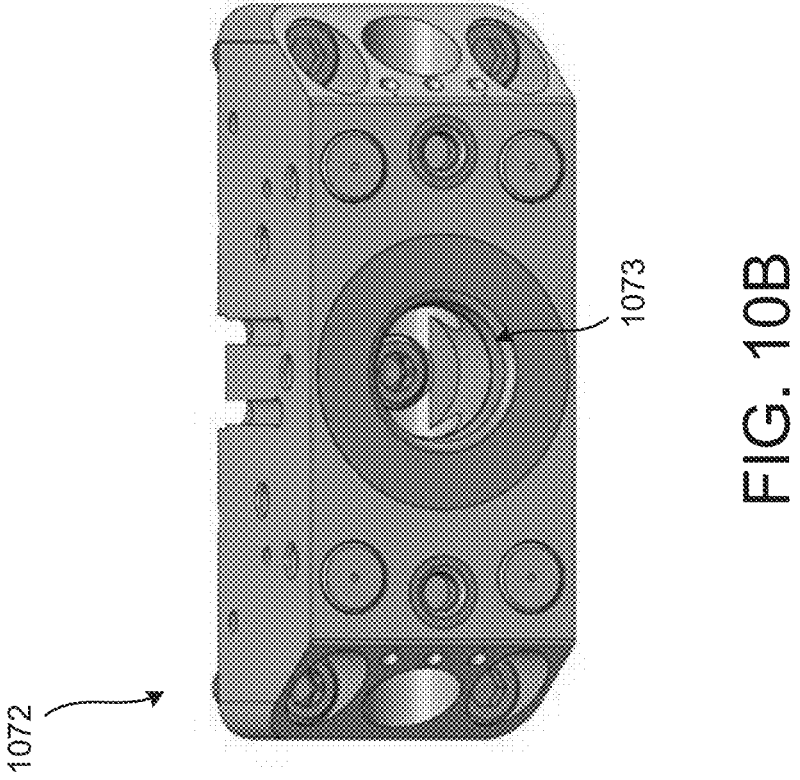

With reference first to FIG. 10A through FIG. 10C, engagement, or grasping, between a robot of a workcell and a fluid device 1030 includes coupling between a robot grasping feature 1072 of the robot and at least one of the robot engagement features 1031 of the fluid device 1030. In some variations, the coupling between the robot and the fluid device 1030 comprises receiving the at least one robot engagement feature 1031 within an aperture of the robot grasping feature 1072. As partially shown in FIG. 10B, the at least one robot engagement feature 1031 may be received within an opening 1073 of the robot grasping feature 1072. FIG. 10C is a cross-sectional view of an illustrative rendering of the robot grasping feature 1072, showing a first clamp 1074 and a second clamp 1075 configured to be translated relative to the opening 1073. Specifically, after the at least one robot engagement feature 1031 of the fluid device 1030 is received within the opening 1073 of the robot grasping feature 1072, the first clamp 1074 and the second clamp 1075 may be translated toward the opening 1073 to grasp the at least one robot engagement feature 1031 and, therefore, the fluid device 1030. After the clamps 1074, 1075 are engaged with the fluid device 1030 via the at least one robot engagement feature 1031, the robot may manipulate (e.g., rotate, translate, invert) the fluid device 1030 as required by the methods described herein.

Figure 10D:
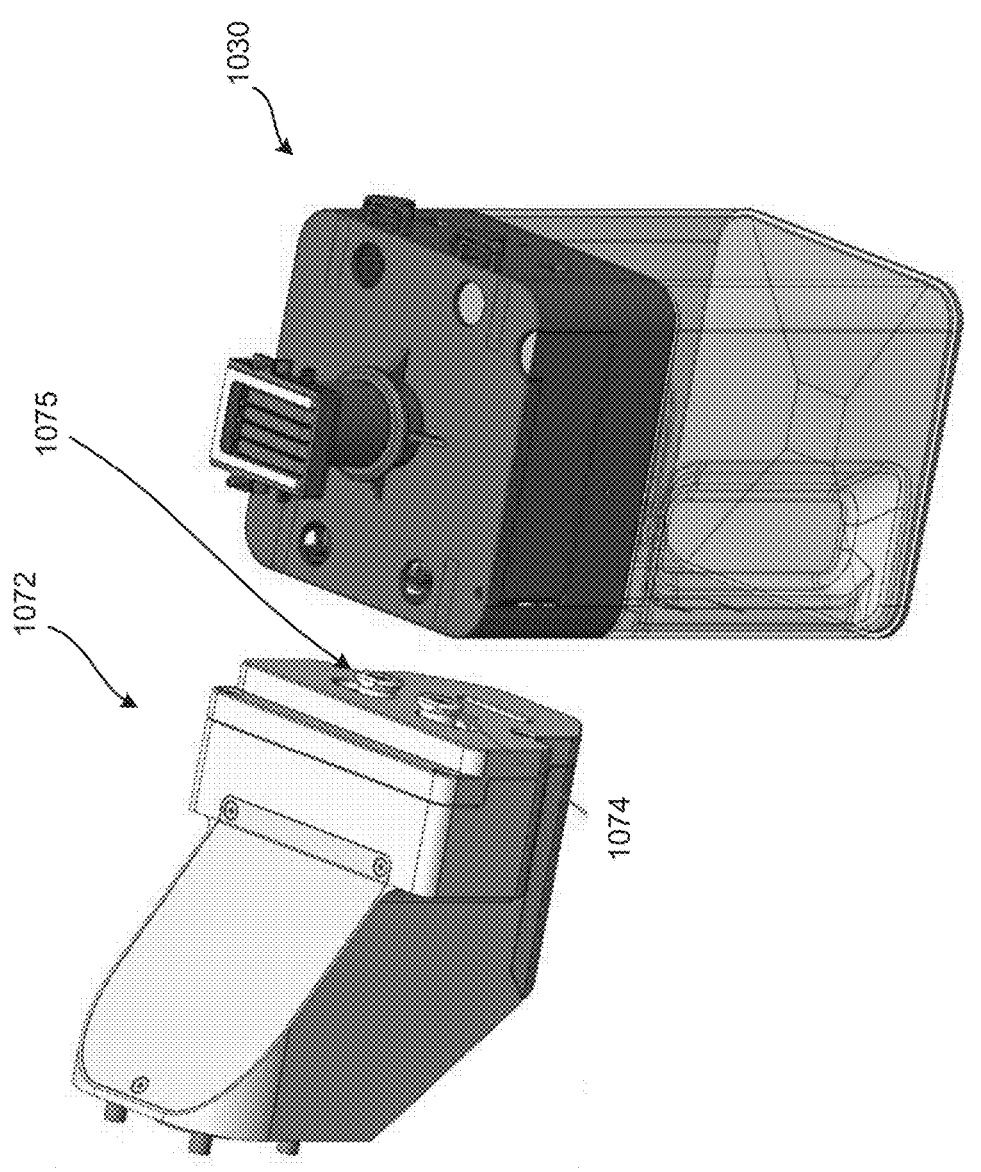
FIG. 10D is a rendering of an illustrative variation of a robot grasping feature of a material handling system of a workcell and robot engagement features of a fluid device.
Figures 10E, 10F:
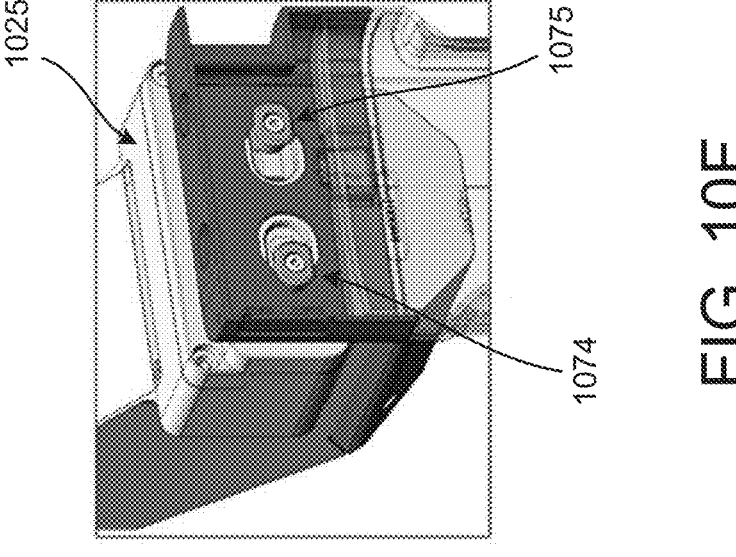
FIG. 10E is a rendering of a first connection position of robot engagement features of a fluid device and clamps of a robot grasping feature of a material handling system of a workcell.
FIG. 10F is a rendering of a second connection position of robot engagement features of a fluid device and clamps of a robot grasping feature of a material handling system of a workcell.

With reference now to FIG. 10D through FIG. 10F, illustrative variations of a robot end effector of the material handling system of the workcell is shown. The robot end effector, which may be robot grasping feature 1072, can be configured to life, rotate, invert, and the like, the fluid device to prepare the fluid device for loading into the sterile liquid transfer system.

As shown in FIG. 10D, engagement, or grasping, between a robot of a workcell and a fluid device 1030 includes coupling between a robot grasping feature 1072 of the robot and at least one of the robot engagement features (indicated by reference numeral 1031 in FIG. 10E) of the fluid device 1030, the robot engagement features 1073 being depressions, openings, and the like. In some variations, the coupling between the robot and the fluid device 1030 comprises sliding contact between a first clamp 1074 and a second clamp 1075 of the robot grasping feature 1072 within respective ones of the robot engagement features, as better shown in FIG. 10E and FIG. 10F. In particular, as shown in FIG. 1-F, a first coupling position of the clamps 1074, 1075 and respective robot engagement features 1031 is shown. In the first coupling position, the first clamp 1074 and the second clamp 1075 are passed into an opening defined by the respective robot engagement features 1031. After being inserted into the respective openings, the first clamp 1074 and the second clamp 1075 may be translated in opposite directions toward a second coupling position, thereby engaging the clamps 1074, 1075 with surfaces of the respective robot engagement features 1031 and grasping the fluid device 1030. After the clamps 1074, 1075 are engaged with the fluid device 1030 via the at least one robot engagement feature 1031, as shown in FIG. 10F, the robot may manipulate (e.g., rotate, translate, invert) the fluid device 1030 as required by the methods described herein.

Returning to method 800 of FIG. 8, the instrument head can be moved within the sterile liquid transfer system and the fluid device, and the cartridge can be engaged with the sterile liquid transfer system at subprocess 804.

Figure 11:
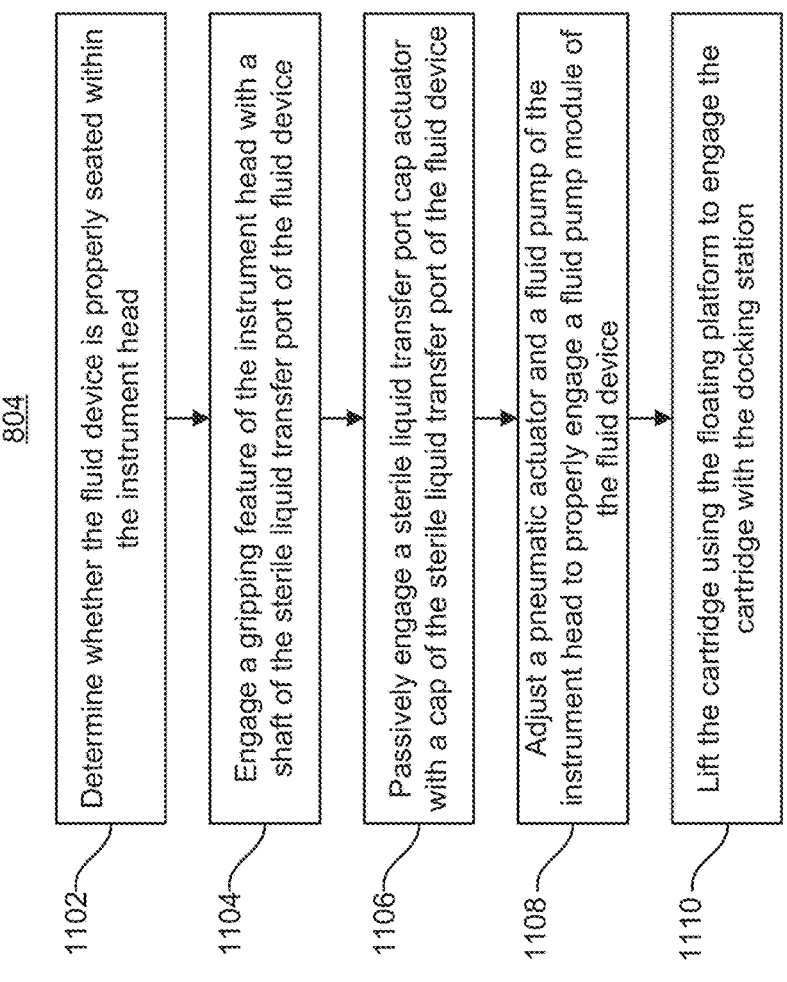
FIG. 11 is a flow diagram of engagement between the fluid device and the instrument head of the sterile liquid transfer system.

In some variations, and as shown in FIG. 11, subprocess 804 may comprise determining whether the fluid device is properly seated within the instrument head, engaging a shaft of the sterile liquid transfer port of the fluid device to secure the fluid device, passively engaging a sterile liquid transfer port cap actuator with a cap of the sterile liquid transfer port of the fluid device, adjusting a pneumatic actuator and fluid pump of the instrument head to properly engage a fluid pump module of the fluid device, and lifting the cartridge using the floating platform to engage the cartridge with the docking station.

After the fluid device is positioned within the instrument head of the sterile liquid transfer system at step 802 of method 800, a position of the fluid device within the instrument head is evaluated at step 1102 of subprocess 804. For example, data from instrument head sensors can be received by the controller and evaluated to determine whether the fluid device is correctly positioned within the instrument head. With reference to FIG. 12A through FIG. 12C, the instrument head sensors can include electromechanical sensors configured to detect a presence of the fluid device. As shown in FIG. 12A and FIG. 12B, step 1102 of subprocess 804 can include receiving data from a first limit switch 1241 and a second limit switch 1242, respectively, and evaluating the data to determine whether fluid device 1230 is properly positioned within instrument head 1222. If it is determined the fluid device 1230 is not properly seated within the instrument head 1222, the robot of the material handling system can be instructed to adjust a position of the fluid device 1230 within the instrument head 1222 and the evaluation can be performed again. As shown in FIG. 12C, upon proper positioning of the fluid device 1230 relative to the instrument head 1222, a first connector 1266 of the fluid device 1230 can be coupled to a second connector 1267 of the instrument head 1222. One or both of the first connector 1266 and the second connector 1267 may be non-valved. In some variations, the second connector 1267 of the instrument head 1222 can be coupled to a spring so that it can float in both a linear and rotational direction to allow for some misalignment and self-correction during connection between the fluid device 1230 and the instrument head 1222.

Figure 12E:
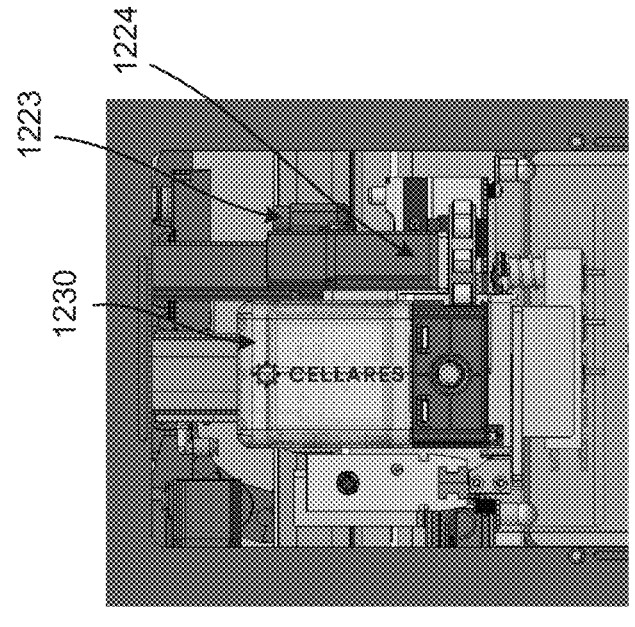
FIG. 12E is a rendering of a peristaltic pump of an instrument head engaging with a fluid device during a step of an illustrative method for automated fluid transfer within a sterile liquid transfer system.
Figure 12D:
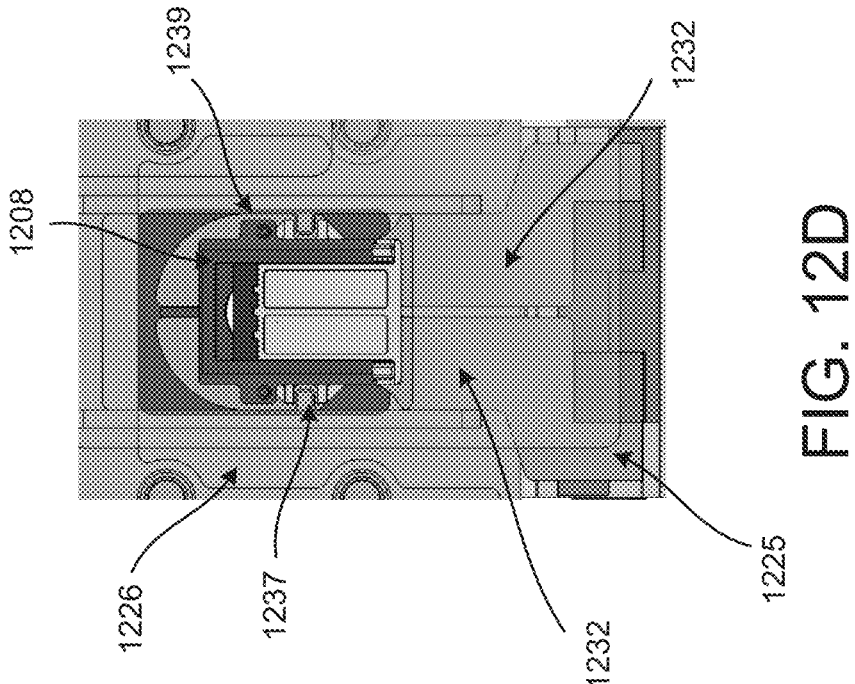
FIG. 12D is a rendering of a gripping feature of an instrument head engaging with a fluid device during a step of an illustrative method for automated fluid transfer within a sterile liquid transfer system.

In some variations, when the fluid device is determined to be properly seated, a gripping feature 1225 of the instrument head can engage a shaft of a sterile liquid transfer port of the fluid device at step 1104 of subprocess 804, as shown in FIG. 12D. In some variations, the gripping feature 1225 may include a gripping feature end effector 1232 comprising two parallel jaws configured to grip a shaft of the sterile liquid transfer port of the fluid device after the fluid device is properly seated within the instrument head.

Figure 12F:
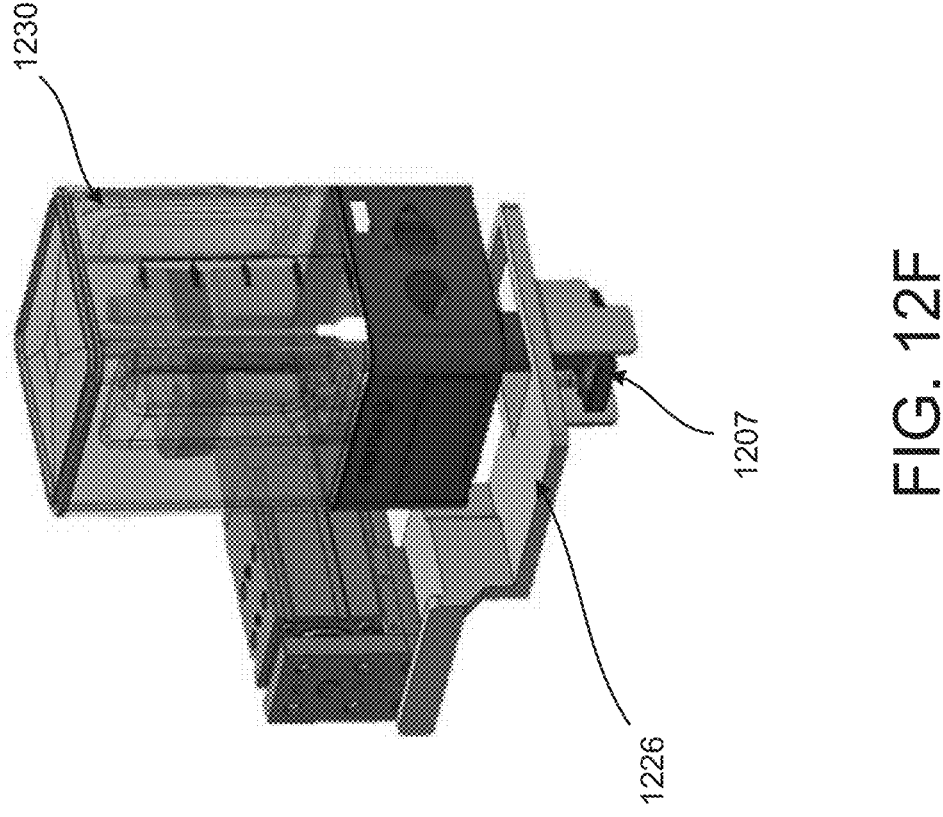
FIG. 12F is a rendering of a sterile liquid transfer port cap actuator of an instrument head of a sterile liquid transfer system and a sterile liquid transfer port of a fluid device.

In some variations, a sterile liquid transfer port cap actuator 1226 can be passively engaged with a cap 1208 of a sterile liquid transfer port of the instrument head at step 1106 of subprocess 804. For example, detent engagement features 1239 of the sterile liquid transfer port cap 1208 of the sterile liquid transfer port can be operatively positioned with respect to a detent 1237 of the sterile liquid transfer port cap actuator 1226, as shown in FIG. 12B. A structural arrangement of the sterile liquid transfer port cap actuator 1226 of the instrument head and the sterile liquid transfer port 1207 of the fluid device 1230 during passive engagement is shown in FIG. 12F. In this position, when the sterile liquid transfer port cap actuator 1226 is actuated, the operatively positioned detent 1237 of the sterile liquid transfer port cap actuator 1226 can engage and move the cap 1208 of the sterile liquid transfer port.

In some variations, a fluid pump 1224 can be positioned at step 1108 of subprocess 804 via a pneumatic actuator 1223 to properly engage a fluid pump module (including compressible fluidic tubing) of a fluid device 1230, as shown in FIG. 12E. In some variations, and as described previously with reference to FIG. 3A, engagement of the fluid pump 1224 and the fluid pump module of the fluid device 1230 may comprise adjusting a position of e.g., bearings of a rotor of a peristaltic pump so that a predetermined occlusion of a compressible fluidic tubing of the fluid pump module is achieved. For example, when the fluid pump 1224 is a peristaltic pump, translation of the pneumatic actuator(s) 1223 may adjust a position of a central axis of a rotor of the peristaltic pump so that bearings thereof achieve a predetermined occlusion of a corresponding compressible fluidic tubing of the fluid device. The predetermined occlusion can be determined according to a desired flow rate and may be based on a dimension of the compressible fluidic tubing, dimensions of a track of the fluid pump module of the fluid device, a viscosity of the fluid being transferred, and the like. In some variations, the predetermined occlusion can be achieved during a fluid transfer operation using a feedback loop and based on information (e.g., linear translation, pressure) provided by or sensed by the pneumatic actuator(s) 1223 and the peristaltic pump. For example, when linear translation is used to determine the predetermined occlusion, initially, a relative position of the track, a size of the compressible fluidic tubing within the track, and a relative position of the rotor/bearings of the peristaltic pump can be known. The predetermined occlusion may be a distance between the track and the rotor/bearings of the peristaltic pump, a dimension of the size of the compressible fluidic tubing within the track, or a linear translation distance of the rotor/bearings. As the pneumatic actuator(s) 1223 is actuated, a e.g., distance between the rotor/bearings and the track can decrease until it is determined that the predetermined occlusion (i.e., a distance between the rotor/bearings and the track) is achieved. In another example, when pressure is used to determine the predetermined occlusion, initially, a pressure sensed by the peristaltic pump and pneumatic actuator 1223 can be known. The predetermined occlusion may be a desired pressure calculated based on particular dimensions and characteristics of the compressible fluidic tubing and, when the desired pressure is sensed by the peristaltic pump and pneumatic actuator 1223 upon engagement of the peristaltic pump and the compressible fluidic tubing, further translation of the pneumatic actuator 1223 can be halted.

In some variations, the cartridge can be secured within the docking station of the second portion of the sterile liquid transfer station by lifting the floating platform so that the cartridge is engaged with the docking station at step 1110 of subprocess 804. As previously shown in FIG. 5F, the platform of the docking station can include a cartridge loading bracket 551 adjacent a floating platform recess 514 and sensor(s) 552 configured to determine when the cartridge is "clamped" to the platform. If the cartridge is misaligned, a portion of the sensor(s) 522 may be configured to determine this such that the cartridge can be repositioned by a robot of the material handling system of the workcell. If the cartridge is properly aligned, a portion of the sensor(s) 522 will be active, indicating that the cartridge is "clamped" to the platform.

In some variations, securing the fluid device within the instrument head can include performing flow fidelity testing, such as on-board leak and flow check functionality, prior to initializing fluid transfer. For example, the leak and flow check can comprise a flow or pressure decay test. The pressure decay test may include pressurizing an area of the fluid device and monitoring the area over time to determine whether the intended pressure changes.

Returning to method 800 of FIG. 8, and with the fluid device and the cartridge both secured within the sterile liquid transfer system, subprocess 806 of method 800, which will be described with reference to FIG. 13A through FIG. 13E, can be performed to align and connect the sterile liquid transfer port of the fluid device and a corresponding sterile liquid transfer port of the cartridge. Generally, at subprocess 806 of method 800, the instrument head is moved by the gantry to an expected location of the corresponding sterile liquid transfer port of the cartridge, at which point an instrument head sensor (e.g., a distance sensor) detects edges of the corresponding sterile liquid transfer port and confirms the real location of the detected edges relative to a predicted location thereof. The edges can be detected based on changes in distance data obtained by the instrument head sensor in view of expected changes in the distance data when an edge is present. In this way, as the gantry moves the instrument head, distance data from the instrument head sensor can be used in combination with X and Y positions of the gantry to detect and map edges of the corresponding sterile liquid transfer port based on a position of the gantry. Subprocess 806 of method 800 will be described in more detail below.

Figure 13A:
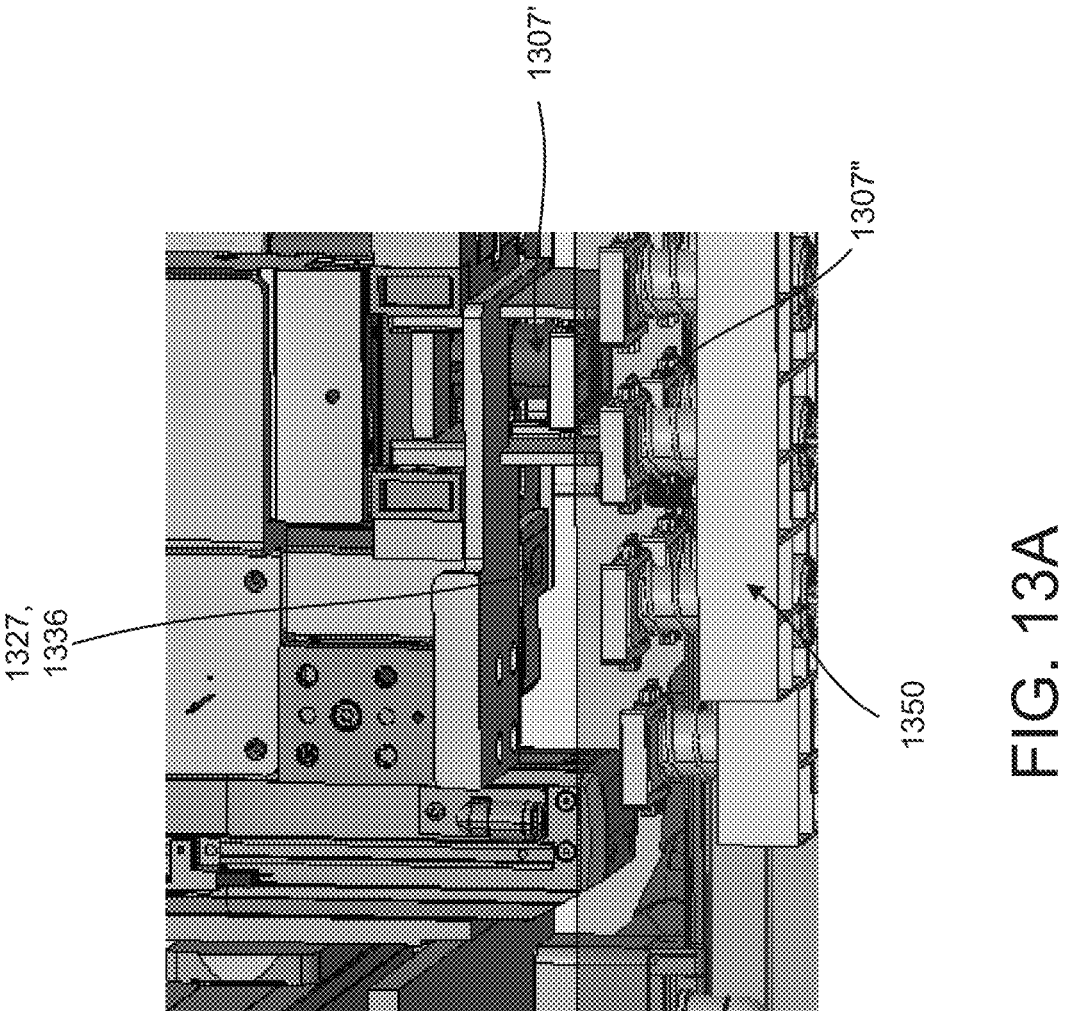
FIG. 13A is a rendering of a positioning of a fluid device and a cartridge during a step of an illustrative method for automated fluid transfer within a sterile liquid transfer system.
Figure 13B:
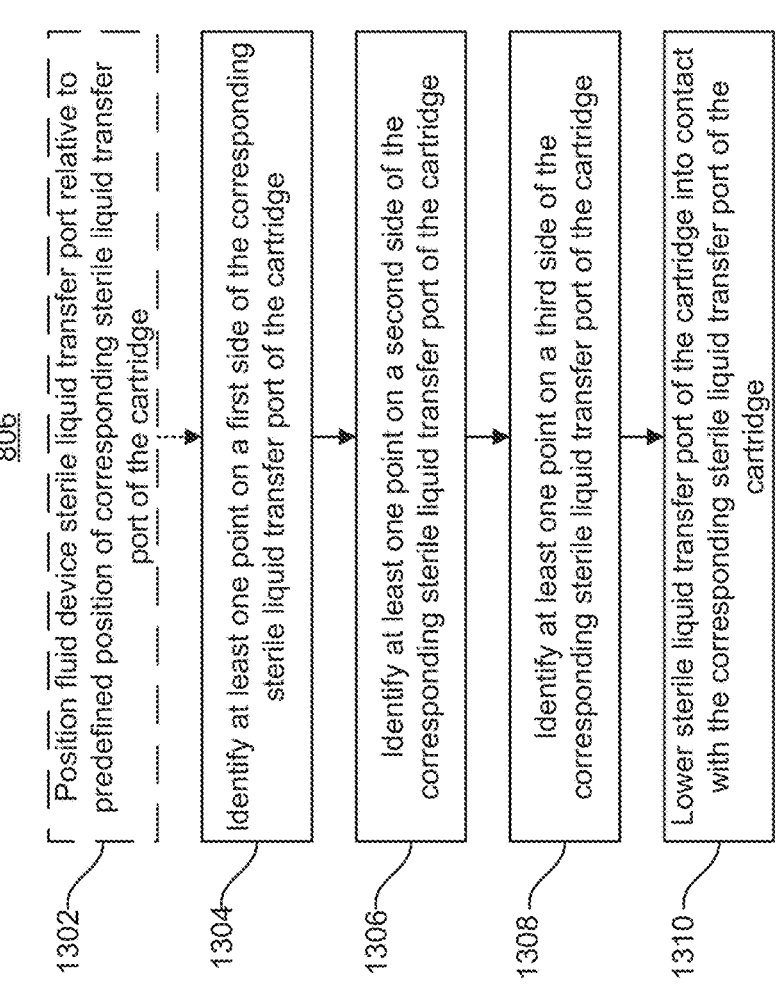
FIG. 13B is a flow diagram of an alignment step of an illustrative method for automated fluid transfer within a sterile liquid transfer system.
Figure 13D:
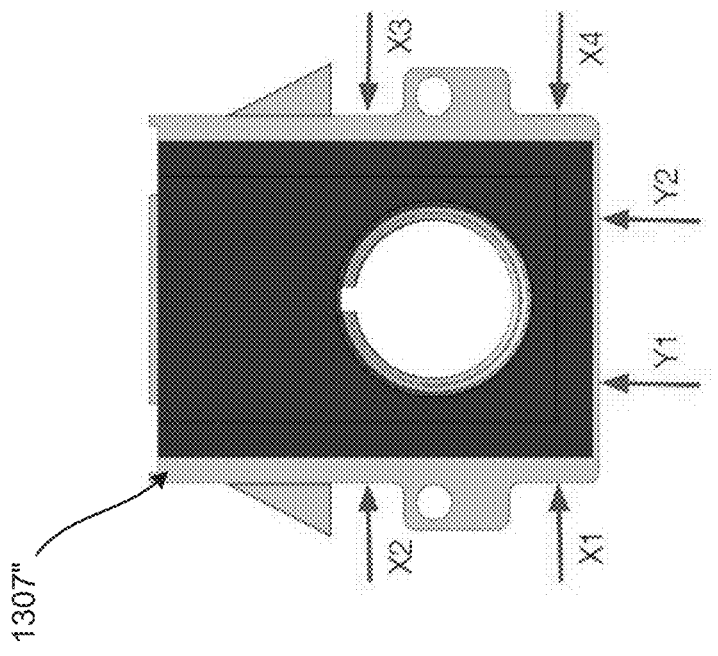
FIG. 13D is a rendering of a sterile liquid transfer port of a cartridge and edge measurements used during an alignment step of an illustrative method for automated fluid transfer within a sterile liquid transfer system.
Figure 13C:
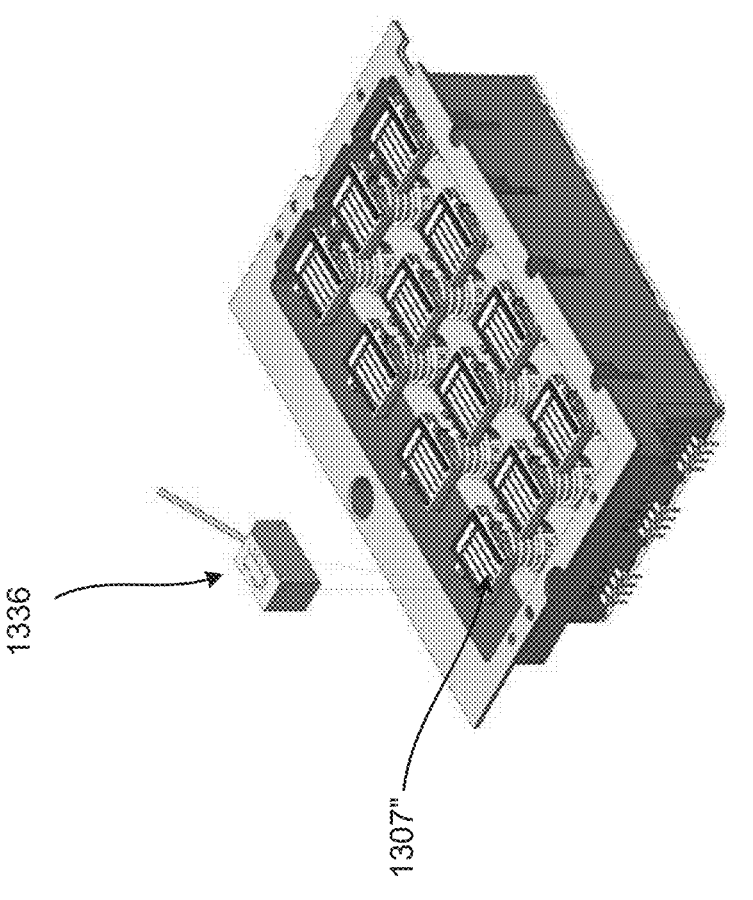
FIG. 13C is a rendering of a distancing sensor used during an alignment step of an illustrative method for automated fluid transfer within a sterile liquid transfer system.
Figure 13E:
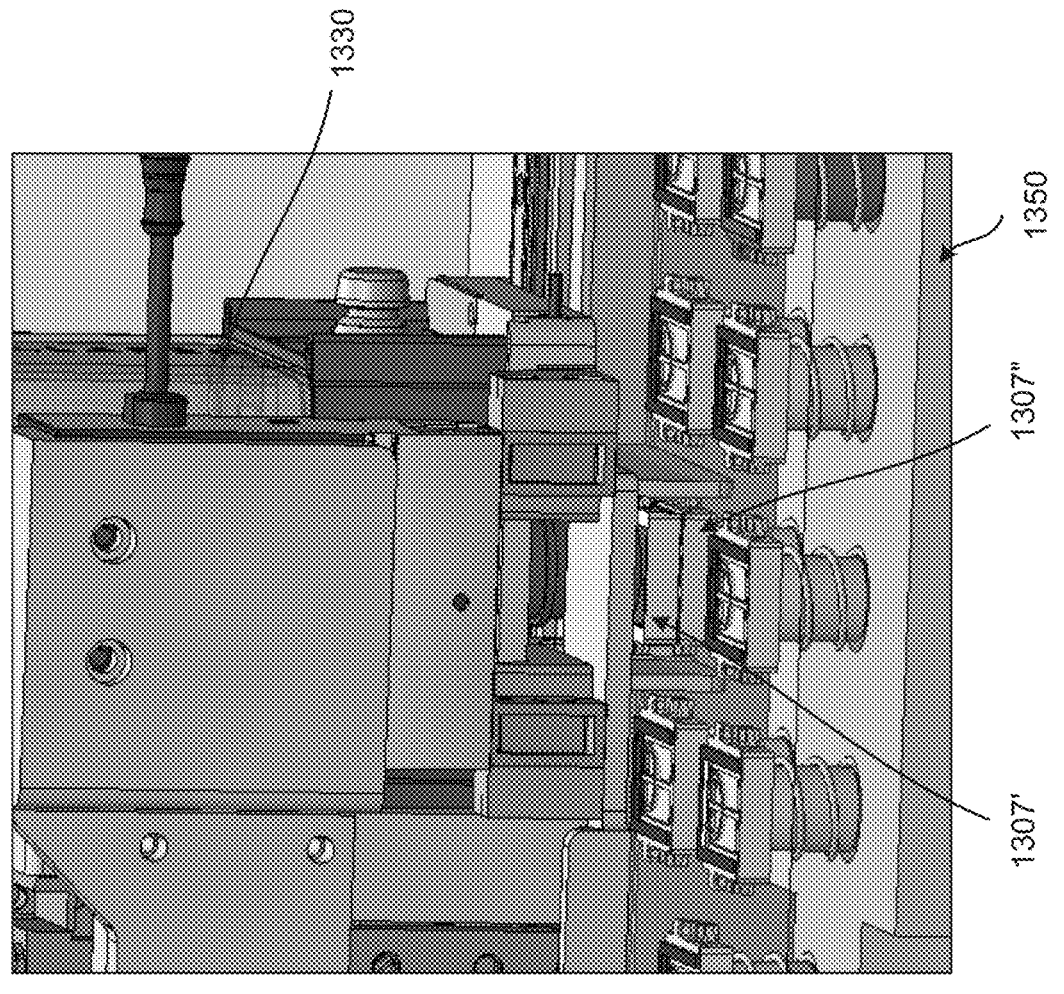
FIG. 13E is a rendering of a top view of a sterile liquid transfer port of a fluid device within an instrument head during an alignment step of an illustrative method for automated fluid transfer within a sterile liquid transfer system.

Initially, as shown in FIG. 13A, alignment may include movement of the instrument head by the gantry to roughly position the sterile liquid transfer port of the fluid device proximate a corresponding sterile liquid transfer port of the cartridge. The initial positioning can be based on expected coordinates of the corresponding sterile liquid transfer port of the cartridge, which may include a plurality of sterile liquid transfer ports arranged in an array or the like. For example, the sterile liquid transfer port 1307' of the fluid device can be positioned proximate a corresponding sterile liquid transfer port 1307" of a cartridge 1350. An instrument head sensor 1327, such as distance sensor 1336, may be used for the initial positioning. Subsequently, a final position of the sterile liquid transfer port of the fluid device can be obtained. With reference to FIG. 13B, subprocess 806 will be described. Step 1302 of subprocess 806 includes the initial positioning of the sterile liquid transfer port of the fluid device, which was described with reference to FIG. 13A. Steps 1304 through 1308 include alignment of the sterile liquid transfer port of the fluid device with the corresponding sterile liquid transfer port of the cartridge using the distance sensor 1336 of the instrument head. FIG. 13C shows a distance sensor 1336 of an instrument head, in isolation, and a corresponding sterile liquid transfer port 1307" of a sterile liquid transfer port array of a cartridge, in isolation, to illustrate the alignment process. FIG. 13D illustrates an exemplary subprocess 806 wherein two points are acquired for each of a first side, a second side, and a third side of the corresponding sterile liquid transfer port 1307" of the cartridge, corresponding to each of steps 1304, 1306, and 1308. For example, X1 and X2 may be points acquired on the first side of the sterile liquid transfer port 1307", Y1 and Y2 may be points acquired on the second side of the sterile liquid transfer port 1307", and X3 and X4 may be points acquired on the third side of the sterile liquid transfer port 1307". In some variations, the points acquired at each of steps 1304, 1306, and 1308 may include x-coordinates, y-coordinates, or a combination thereof. In some variations, the points acquired at each of steps 1304, 1306, and 1308 may be acquired based on data received from the distancing sensor 1336 of the instrument head and an understanding of the relative position of the sterile liquid transfer port of the instrument head and the corresponding sterile liquid transfer port of the cartridge. For example, data from the distance sensor 1336 can indicate a distance to a surface the cartridge on which the sterile liquid transfer port array is disposed. As the instrument head is translated via the gantry and toward the predicted coordinates of the corresponding sterile liquid transfer port, a first point may be acquired on a first side of the corresponding sterile liquid transfer port when a distance measurement from the distance sensor 1336 jumps from a baseline distance (which may correspond to a distance from the instrument head to the surface of the cartridge) to a shortened distance, reflecting the presence of the corresponding sterile liquid transfer port. Movement of the instrument head by the gantry may be continuously performed until a desired number of points for each side has been obtained. In some variations, the points acquired at steps 1304, 1306, and 1308 can be used in conjunction with a known geometry of the sterile liquid transfer port to ensure precise alignment of the sterile liquid transfer port of the fluid device and the corresponding sterile liquid transfer port of the cartridge at step 1310 of sub process 806. For example, at step 1310, the sterile liquid transfer port 1307' of the fluid device 1330 can be lowered into contact with the corresponding sterile liquid transfer port 1307" of the cartridge 1350, as shown in FIG. 13E. In some variations, bringing the sterile liquid transfer port 1307' and the corresponding sterile liquid transfer port 1307" includes coupling alignment features (e.g., alignment features 218 of sterile liquid transfer port 224 of FIG. 2F and FIG. 2G) of the sterile liquid transfer port 1307' with corresponding features of the corresponding sterile liquid transfer port 1307". After lowering the sterile liquid transfer port, a detent engagement feature of the sterile liquid transfer port is engaged with a detent of the sterile liquid transfer port cap actuator. The engagement between the detent and the detent engagement feature permits the cap to be actuated at step 808 of method 800.

Returning to method 800, the connected sterile liquid transfer ports can, at step 808, be prepared for fluid transfer. The preparation can include opening fluid communication between the fluid device and the cartridge and performing sterilization of the connected sterile liquid transfer ports. For example, caps of the connected sterile liquid transfer ports may first be actuated by a sterile liquid transfer port cap actuator to translate the caps to an open position. During the actuation, and with the caps in a partially open position, sterilization of the connected sterile liquid transfer ports can be performed. As described herein, a sterilant can be flowed throughout fluid conduit of the fluid device and into the connection between the sterile liquid transfer port of the fluid device and the corresponding sterile liquid transfer port of the cartridge. With the sterilization complete, the caps can be actuated to a fully open position and corresponding valves of the connected sterile liquid transfer ports can be actuated in order to open fluid communication between the fluid device and the cartridge.

At step 810 of method 800, fluid may be transferred between the fluid device and the cartridge. The transferred fluid may include reagents, biological materials, waste, biological samples for analysis, and the like. In some variations, the fluid transfer may be controlled by the controller and based on data acquired from sensor(s) 727 of FIG. 7A. The sensor(s) 727 may be optical sensors 738 and can be used to determine the presence of liquid or air within fluid conduit of the fluid device, thereby aiding in the control of fluid transfer between the fluid device and a cartridge. The optical sensors 738 may have a vantage to fluid conduit of the fluid device via e.g., one or more viewing windows of the fluid device. For example, with reference to FIG. 7B, the optical sensors 738 can be used to identify a liquid to air transition and/or an air to liquid transition by processing data received from the optical sensors 728 to identify rising edges and falling edges of the data. This data can be used to estimate a fluid flow rate and to modify fluid pump parameters, accordingly, to achieve a desired fluid flow rate.

In some variations, the data from the optical sensors 738 can be used in combination with timing data to estimate fluid flow within the fluid conduits of the fluid device and to control the pneumatic actuator and fluid pump of the instrument head based on the fluid flow estimation and in view of a desired fluid flow rate. For example, a rate of the fluid flow can be estimated by timing how long it takes a fluid to travel from a first sensor 761 to a second sensor 762, or vice versa, at a set fluid pump speed and knowing parameters of the fluid conduit. For example, an internal diameter of the fluid conduit and/or a distance between the first sensor 761 and the second sensor 762 within the fluid conduit may be known.

In some variations, the fluid flow rate can be estimated as a volume of fluid between the first sensor 761 and the second sensor 762 divided by a time required for a leading edge of the fluid volume to travel between the first sensor 761 and the second sensor 762. The volume of fluid can be determined based on known dimensions of the fluid conduit and a fluid path distance between the first sensor 761 and the second sensor 762. The leading edge of the fluid volume may be tracked based on air to liquid transitions detected by the first sensor 761 and the second sensor 762.

Figure 7B:
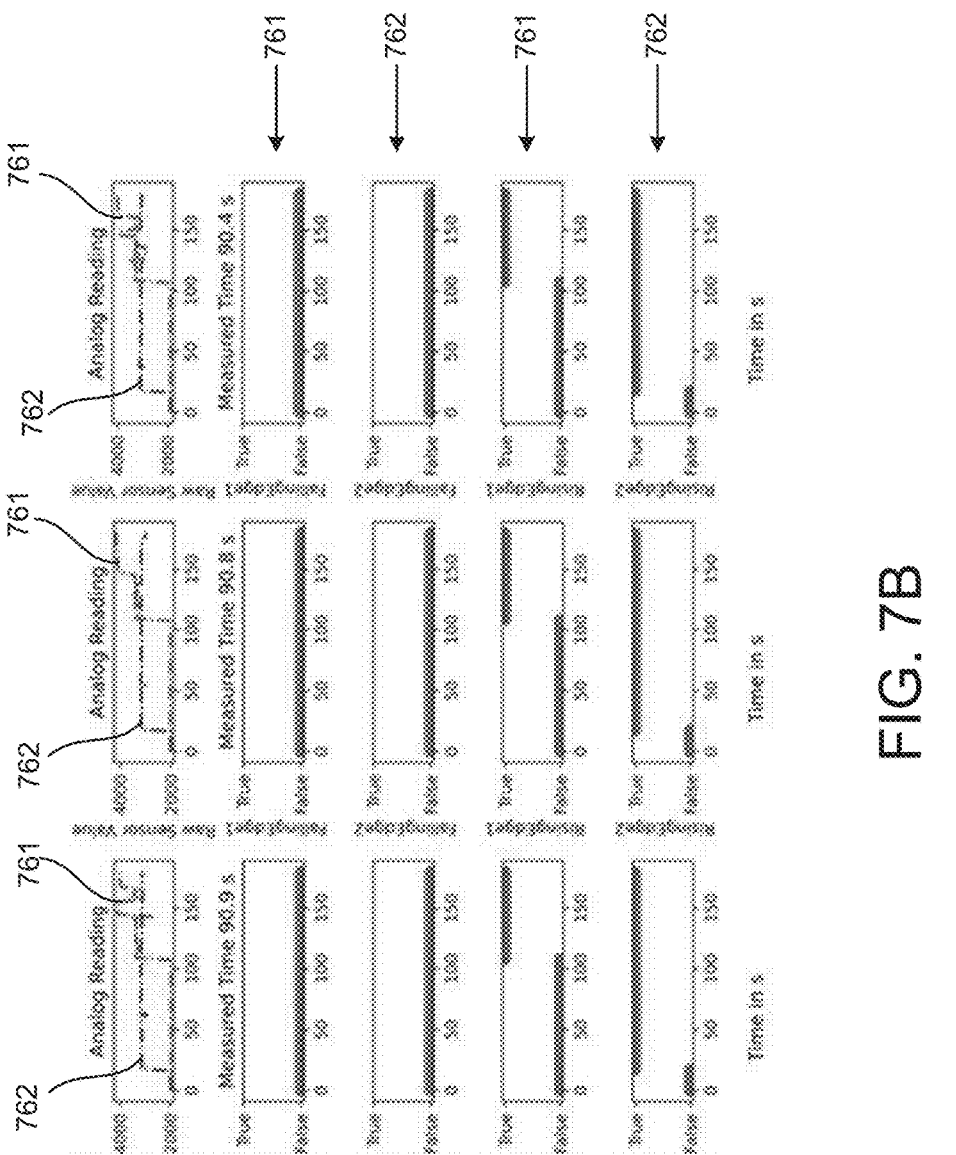
FIG. 7B is a graphical illustration of fluid flow control using sensors of an instrument head of a first portion of a sterile liquid transfer system.

Aspects of the fluid flow rate estimation are shown in FIG. 7B. Each column of the graphical illustrations of FIG. 7B reflect a unique experiment used during the calibration. The "Raw Sensor Value" graph for each column depicts analog readings from each of the first sensor 761 and the second sensor 762. The below rows reflect, for each of the first sensor 761 and the second sensor 762, a detected falling edge or a detected rising edge. The "falling edge" corresponds to an air to liquid transition while the "rising edge" corresponds to a liquid to air transition. For example, the "RisingEdge1" graph and the "RisingEdge2" graph for each column depict the time when corresponding sensors are triggered, indicating a liquid to air transition. That is, a "false" measurement indicates the presence of a liquid, and a "true" measurement indicates the presence of air.

In some variations, and with particular reference to "RisingEdge1" in the first column, data from the first sensor 761 show the time it takes to detect a transition state from liquid to air (e.g., slightly over 100 seconds). Similarly, with reference to "RisingEdge2" in the first column, data from the second sensor 762 shows the time it takes to detect a transition state from liquid to air (e.g., around 25 seconds). By having two optical sensors with two data points, the controller can determine the fluid flow rate based on the volume therebetween and measured travel time.

In some variations, a flow rate estimation can be used in real time to adjust e.g., a peristaltic pump to ensure a consistent fluid flow rate during fluid transfer. The adjustment may be a change in rotational speed of the rotor, a change in the predetermined occlusion, and the like.

In some variations, a flow rate estimation can be used to calibrate e.g., a peristaltic pump to ensure a consistent fluid flow rate during fluid transfer (e.g., transfer of reagents, waste, and cellular samples). For example, a linear position of the fluid pump, a rotational speed of the rotor, and the like can be adjusted based on the time measured during the calibration to ensure a desired fluid flow rate is achieved.

Figures 14A, 14B:
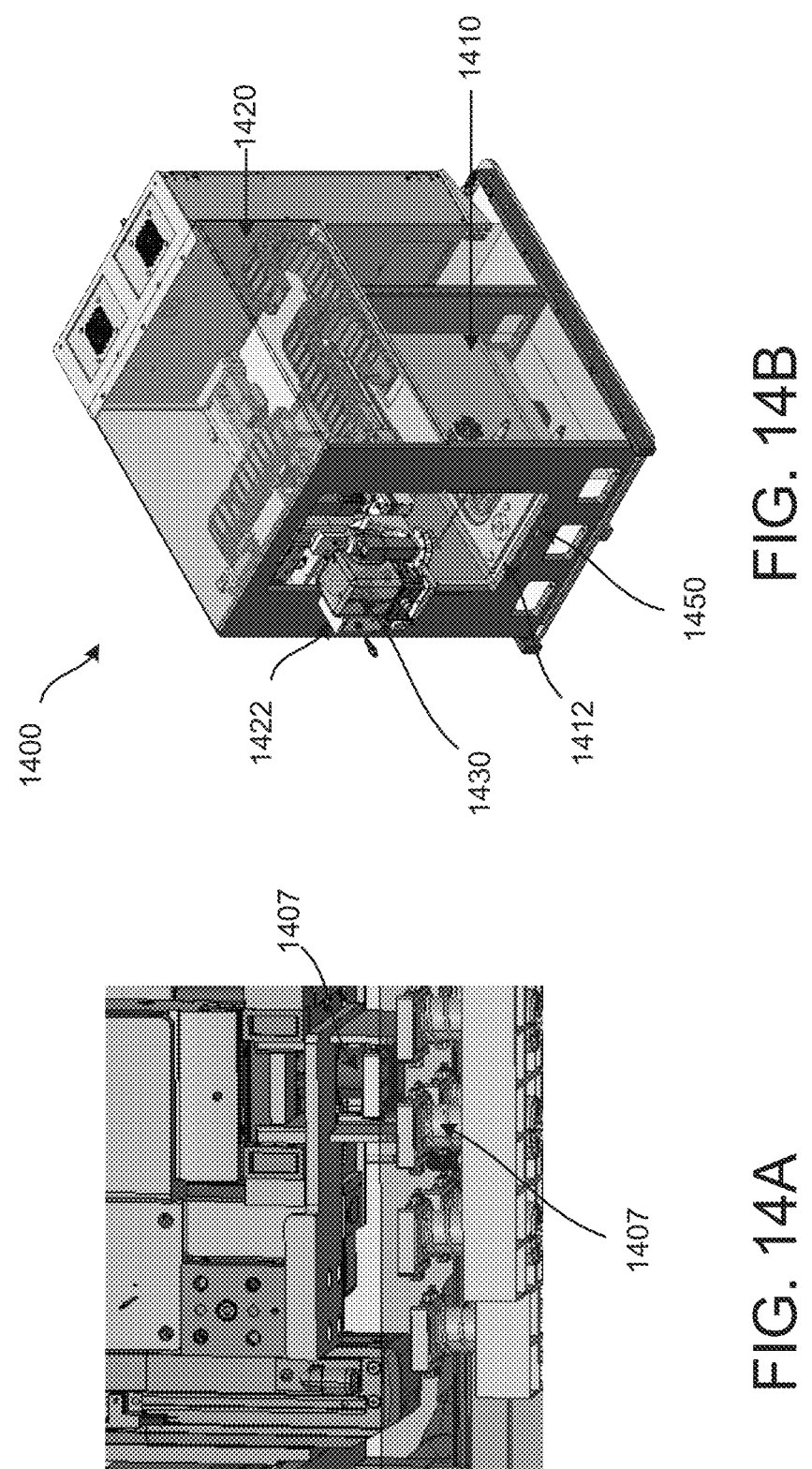
FIG. 14A is a rendering of disengagement of a fluid device and a cartridge during an illustrative method for automated fluid transfer within a sterile liquid transfer system.
FIG. 14B is a rendering of positioning of a fluid device for pick up by a material handling system of a cell processing system during an illustrative method for automated fluid transfer within a sterile liquid transfer system.

After fluid transfer is complete at step 810 of method 800, the connected sterile liquid transfer ports can be disconnected, as shown in FIG. 14A, at step 812 of method 800. The disconnection can include performing, in reverse, all or a portion of the processes of step 808 to prepare the connected sterile liquid transfer ports for fluid transfer. The fluid device can then be moved to a drop-off/pick up (or loading/unloading) position at step 814 of method 800, as shown in FIG. 14B.

Additional detail regarding sterile liquid transfer ports and aspects thereof are provided e.g., in U.S. patent application Ser. No. 17/331,556, issued as U.S. Pat. No. 11,376,587, entitled "Fluid Connector", which is incorporated by reference herein.

Figure 15A:
FIGS. 15A-15C are renderings of positions of a cap of a sterile liquid transfer port during an illustrative method of automated fluid transfer within a sterile liquid transfer system.
Figure 15B:
Figure 15C:
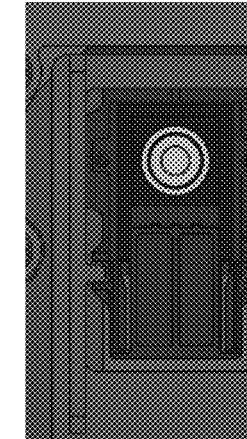

Turning now to FIG. 15A through FIG. 15C, a variety of positions of the cap of the sterile liquid transfer ports described herein is shown. For instance, as in FIG. 15A, a closed position suitable for loading and unloading of the fluid device within the sterile liquid transfer system is shown. During sterilization, the caps of the sterile liquid transfer ports can be in a partially open position, as shown in FIG. 15B. After sterilization, and to perform fluid transfer, the caps of the connected sterile liquid transfer ports can be actuated to a fully open position to permit actuation of corresponding valves within the connected sterile liquid transfer ports and fluid transfer.

Figure 16:
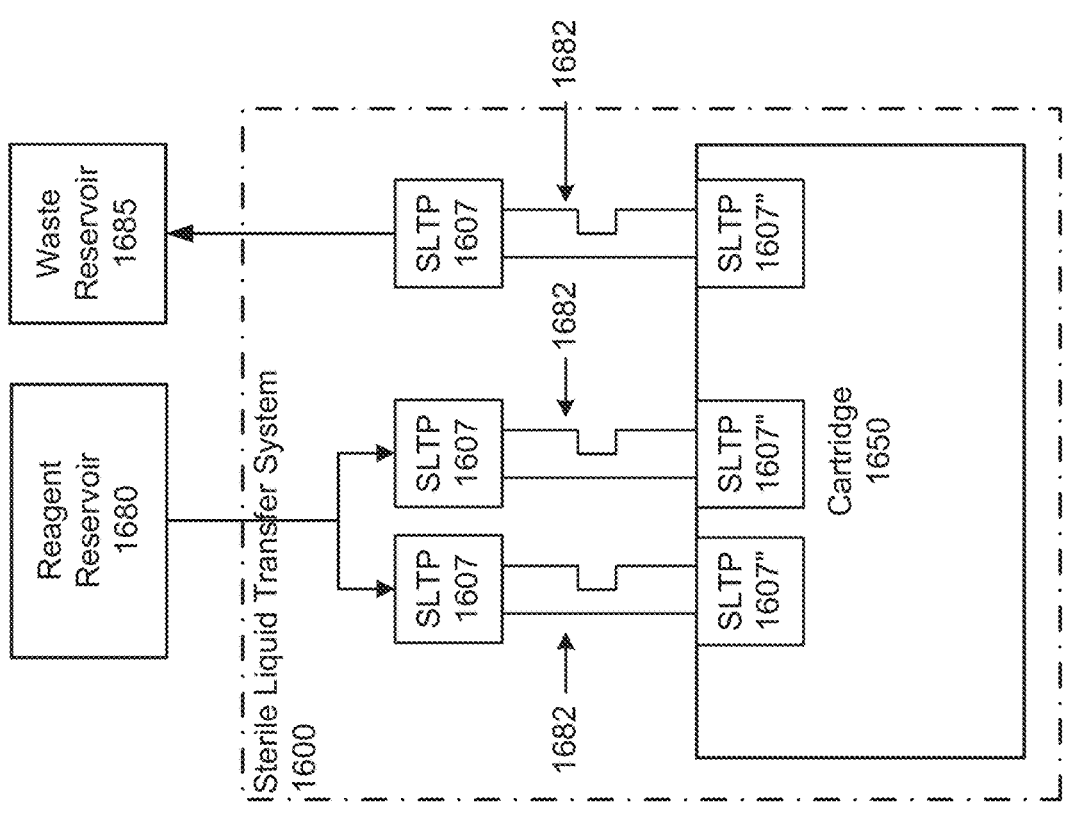
FIG. 16 is a schematic of an illustrative disposable sterile liquid transfer port tip used during fluid transfer within a workcell.

Turning now to FIG. 16, an illustrative schematic of a fluid connector between the workcell and the cartridge is shown.

The illustrative schematic of FIG. 16 contemplates a sterile liquid transfer system without a sterile liquid transfer device. As shown in FIG. 16, the sterile liquid transfer system 1600 may be configured to receive a cartridge 1650 comprising a plurality of sterile liquid transfer ports (SLTP) 1607″. Instead of using a fluid device to transfer fluid (e.g., reagents, culture medium, cells, waste, etc.) into and out of the cartridge 1650, sterile liquid transfer system-based and/or workcell-based infrastructure can be used as reservoirs for the fluids. This eliminates the limitations of fluid device-based fluid replenishment and/or removal, making effectively limitless volumes of fluids available for transfer to the cartridge 1650. Also, the use of infrastructure-based fluid transfer permits the simultaneous transfer of fluids, thus expediting the fluid transfer process.

In some variations, a reagent reservoir 1680 and a waste reservoir 1685, among other fluid reservoirs, may be coupled to the sterile liquid transfer system 1600 or may otherwise be within the workcell and fluidically coupled to the sterile liquid transfer system 1600. Permanent sterile liquid transfer ports 1607 may be disposed in the sterile liquid transfer system 1600 and permit fluidic coupling between the reagent reservoir 1680, the waste reservoir 1685, and the sterile liquid transfer system 1600.

In some variations, when the cartridge 1650 is positioned within e.g., a docking station of the sterile liquid transfer system 1600, a fluidic connection can be made between the permanent sterile liquid transfer ports 1607 of the sterile liquid transfer system 1600 and corresponding sterile liquid transfer ports 1607″ on the cartridge 1650. To minimize the risk of contamination of either the permanent sterile liquid transfer ports 1607 or the sterile liquid transfer ports 1607, the fluidic connection can be formed via a disposable connector 1682. The disposable connector 1682 may be, in an example, a double sided sterile liquid transfer port similar to those described previously herein. The disposable connector 1682 may be retrieved and properly positioned between corresponding sterile liquid transfer ports by a robot of the material handling system of the workcell, or by a gantry of the sterile liquid transfer system. Moreover, the robot or the gantry may be configured to actuate the disposable connector 1682 in a similar manner to that which is described previously herein with reference to fluid devices. After each fluid transfer, the disposable connector 1682 can be disposed of.

In some variations, the permanent sterile liquid transfer ports 1607 and sterile liquid transfer ports 1607″ of the cartridge 1650 can be sterilized according to the processes described herein prior to retrieval and positioning of the disposable connector 1682.

All references cited are herein incorporated by reference in their entirety.

Throughout this application, the term "about" is used to indicate that a value includes the inherent variation of error for the device, or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for sterile fluid transfer between a fluid device and a cartridge for cell processing, the method comprising:

receiving, by an instrument head of a system, the fluid device comprising a sterile liquid transfer port;

aligning the sterile liquid transfer port with one of a plurality of sterile liquid transfer ports of the cartridge using one or more distance sensors of the instrument head to obtain a position of the one of the plurality of sterile liquid transfer ports of the cartridge relative to the instrument head;

connecting the sterile liquid transfer port to the one of the plurality of sterile liquid transfer ports of the cartridge;

engaging a peristaltic pump with a compressible fluidic tubing of a fluid pump module of the fluid device, wherein engaging comprises moving a pneumatic actuator to translate the peristaltic pump relative to the compressible fluidic tubing of the fluid pump module, thereby adjusting an amount of occlusion of the compressible fluidic tubing; and transferring, via the connected sterile liquid transfer ports, fluid between the fluid device and the cartridge.

2. The method of claim 1, further comprising sterilizing internal surfaces of the connected sterile liquid transfer ports prior to transferring the fluid.

3. The method of claim 1, further comprising actuating a cap actuator configured to translate caps of each of the connected sterile liquid transfer ports to open a flow path at an interface of the connected sterile liquid transfer ports.

4. The method of claim 1, wherein moving the pneumatic actuator is performed until a predetermined pressure of fluid within the compressible fluidic tubing or a predetermined amount of occlusion of the compressible fluidic tubing is achieved.

5. The method of claim 1, wherein the aligning is based on data acquired by the one or more distance sensors of the instrument head.

6. The method of claim 5, wherein the aligning comprises detecting at least one edge of the one of the plurality of sterile liquid transfer ports of the cartridge using data acquired by the one or more distance sensors.

7. The method of claim 6, wherein the detecting the at least one edge comprises detecting a plurality of points on the one of the plurality of sterile liquid transfer ports of the cartridge.

8. The method of claim 7, wherein the plurality of points comprises two locations each along three edges of the one of the plurality of sterile liquid transfer ports of the cartridge.

9. The method of claim 1, further comprising receiving a cartridge into a docking station of a second portion of the system.

10. The method of claim 9, further comprising securing a position of the cartridge within the docking station.

11. The method of claim 10, wherein securing the position of the cartridge within the docking station comprises raising a floating platform on which the cartridge is seated to bring the cartridge into contact with a clamping surface of the docking station.

12. The method of claim 1, further comprising performing flow fidelity testing prior to transferring the fluid.

13. The method of claim 1, further comprising estimating, based on data acquired by one or more sensors of the instrument head, a flow rate of fluid transfer.

14. The method of claim 13, wherein the estimating the flow rate of fluid transfer is used to calibrate a volumetric flow rate based on a revolution of a peristaltic pump of the system.

15. The method of claim 1, wherein aligning comprises moving the instrument head from an initial position to a final position using data provided by the distance sensor.

16. A method for fluid transfer between a fluid device and a cartridge for cell processing, the method comprising:

receiving, by an instrument head of a first portion of a system, the fluid device comprising a sterile liquid transfer port;

receiving, by a second portion of the system, the cartridge within a docking station, the cartridge comprising a plurality of sterile liquid transfer ports;

aligning the sterile liquid transfer port with one of a plurality of sterile liquid transfer ports of the cartridge using one or more distance sensors of the instrument head to obtain a position of the one of the plurality of sterile liquid transfer ports of the cartridge relative to the instrument head;

connecting the sterile liquid transfer port of the fluid device to the one of the plurality of sterile liquid transfer ports of the cartridge;

adjusting a position of a pneumatic actuator of the instrument head relative to a fluid pump module of the fluid device, thereby modifying a distance between a peristaltic pump of the instrument head and compressible fluidic tubing of the fluid pump module; and transferring, via the connected sterile liquid transfer ports and after a predetermined fluid pressure is achieved within the compressible fluidic tubing, fluid between the fluid device and the cartridge.

17. The method of claim 16, wherein aligning comprises moving the instrument head from an initial position to a final position using data provided by the distance sensor.

18. The method of claim 16, further comprising sterilizing internal surfaces of the connected sterile liquid transfer ports prior to transferring the fluid.

19. The method of claim 16, further comprising actuating a cap actuator configured to translate caps of each of the connected sterile liquid transfer ports to open a flow path at an interface of the connected sterile liquid transfer ports.

20. The method of claim 16, further comprising securing a position of the cartridge within the docking station, wherein securing the position of the cartridge within the docking station comprises raising a floating platform on which the cartridge is seated to bring the cartridge into contact with a clamping surface of the docking station.

* * * * *